United States Patent
Vendeville et al.

(10) Patent No.: US 12,384,779 B2
(45) Date of Patent: *Aug. 12, 2025

(54) BICYCLIC COMPOUNDS

(71) Applicant: Aligos Therapeutics, Inc., South San Francisco, CA (US)

(72) Inventors: Sandrine Vendeville, Brussels (BE); David McGowan, Brussels (BE); Yannick Debing, Bilzen (BE); Pierre Jean-Marie Bernard Raboisson, Wavre (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 18/302,554

(22) Filed: Apr. 18, 2023

(65) Prior Publication Data

US 2023/0374008 A1    Nov. 23, 2023

Related U.S. Application Data

(60) Provisional application No. 63/484,141, filed on Feb. 9, 2023, provisional application No. 63/363,302, filed on Apr. 20, 2022.

(51) Int. Cl.
| | |
|---|---|
| *C07D 471/04* | (2006.01) |
| *A61K 45/06* | (2006.01) |
| *A61P 31/20* | (2006.01) |
| *C07D 519/00* | (2006.01) |
| *A61P 31/14* | (2006.01) |

(52) U.S. Cl.
CPC ............ *C07D 471/04* (2013.01); *A61K 45/06* (2013.01); *A61P 31/20* (2018.01); *C07D 519/00* (2013.01)

(58) Field of Classification Search
CPC .... C07D 471/04; C07D 519/00; A61K 45/06; A61P 31/20; A61P 31/14
See application file for complete search history.

(56) References Cited

U.S. PATENT DOCUMENTS

| | | |
|---|---|---|
| 6,414,157 B1 | 7/2002 | Lubisch et al. |
| 6,657,063 B1 | 12/2003 | Dow |
| 11,591,341 B2 | 2/2023 | Vendeville et al. |
| 11,952,374 B2 | 4/2024 | Vendeville et al. |
| 11,957,683 B2 | 4/2024 | Vendeville et al. |
| 2005/0054645 A1 | 3/2005 | Miyazaki et al. |
| 2005/0165025 A1 | 7/2005 | Leonardi et al. |
| 2010/0093771 A1 | 4/2010 | Nakamura et al. |
| 2020/0147124 A1 | 5/2020 | Beigelman et al. |
| 2020/0361947 A1 | 11/2020 | Vendeville et al. |
| 2021/0403461 A1 | 12/2021 | Iwata et al. |
| 2022/0119385 A1 | 4/2022 | Vendeville et al. |
| 2022/0169650 A1 | 6/2022 | Vendeville et al. |
| 2023/0051483 A1 | 2/2023 | Vendeville et al. |
| 2023/0091047 A1* | 3/2023 | Grosse ................... A61P 31/12 514/264.1 |
| 2023/0382909 A1 | 11/2023 | Vendeville et al. |
| 2024/0150351 A1 | 5/2024 | Vendeville et al. |

FOREIGN PATENT DOCUMENTS

| | | |
|---|---|---|
| CN | 109956930 | 7/2019 |
| CN | 111039942 | 4/2020 |
| DE | 19747063 | 4/1999 |
| WO | WO 99/02990 | 1/1999 |
| WO | WO 2001/089570 | 11/2001 |
| WO | WO 2005/016927 | 2/2005 |
| WO | WO 2008/038768 | 4/2008 |
| WO | WO 2008/130581 | 10/2008 |
| WO | WO 2019/022061 | 1/2019 |
| WO | WO 2020/182990 | 9/2020 |
| WO | WO 2020/214728 | 10/2020 |
| WO | WO 2022/053010 | 3/2022 |
| WO | WO 2022/087011 | 4/2022 |
| WO | WO 2022/266193 | 12/2022 |
| WO | WO 2023/205653 | 10/2023 |
| WO | WO 2024/073559 | 4/2024 |

OTHER PUBLICATIONS

Koh C, Da BL, Glenn JS. HBV/HDV Coinfection: A Challenge for Therapeutics. Clin Liver Dis. Aug. 2019;23(3):557-572. doi: 10.1016/j.cld.2019.04.005. Epub May 24, 2019. PMID: 31266627; PMCID: PMC6659751. (Year: 2019).*

Fan, et al., "Assembly of Primary (Hetero)Arylamines via CuI/Oxalic Diamide-Catalyzed Coupling of Aryl Chlorides and Ammonia" Org. Lett. (2015) 17(23):5934-5937.

Leermann et al., "Highly Efficient One-Pot Access to Functionalized Arylboronic Acids via Noncryogenic Bromine/Magnesium Exchanges" Org. Lett. (2011) 13(17):4479-4481.

Mfuh et al., "Scalable, Metal- and Additive-Free, Photoinduced Borylation of Haloarenes and Quaternary Arylammonium Salts" J. Am. Chem. Soc. (2016) 138(9):2985-2988.

Sheng et al. "[(CyPF-tBu)PdCl$_2$]: An Air-Stable, One-Component, Highly Efficient Catalyst for Amination of Heteroaryl and Aryl Halides" Org. Lett. (2008) 10(18):4109-4112.

Zhang et al., "Visible-Light-Induced Organocatalytic Borylation of Aryl Chlorides" J. Am. Chem. Soc. (2019) 141(23):9124-9128.

(Continued)

*Primary Examiner* — Jeffrey H Murray
*Assistant Examiner* — Kevin S Martin
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

18 Claims, No Drawings

Specification includes a Sequence Listing.

(56) References Cited

OTHER PUBLICATIONS

International Search Report and Written Opinion mailed Jul. 10, 2023 for PCT Application No. PCT/US2023/065899, filed Apr. 18, 2023.
"IUPAC-IUB Commission on Biochemical Nomenclature Abbreviated Nomenclature of Synthetic Polypeptides (Polymerized Amino Acids)* Revised Recommendations (1971)" *Biochemistry.* (1972) 11(5) :942-944.
Liang, "Hepatitis B: The Virus and Disease" Hepatology (2009) 49(S5):S13-S21.
Sweet, M. J., "The Patentability of Chiral Drugs Post-KSR: The More Things Change, the More They Stay the Same." Berkeley Technology Law Journal (2009) 24(1):129-47.

\* cited by examiner

SEQUENCE LISTING

```
Sequence total quantity: 3
SEQ ID NO: 1            moltype = DNA  length = 20
FEATURE                 Location/Qualifiers
misc_feature            1..20
                        note = Synthetic HBV-forward primer
source                  1..20
                        mol_type = other DNA
                        organism = synthetic construct
SEQUENCE: 1
gtgtctgcgg cgttttatca                                              20

SEQ ID NO: 2            moltype = DNA  length = 21
FEATURE                 Location/Qualifiers
misc_feature            1..21
                        note = Synthetic HBV-reverse primer
source                  1..21
                        mol_type = other DNA
                        organism = synthetic construct
SEQUENCE: 2
gacaaacggg caacatacct t                                            21

SEQ ID NO: 3            moltype = DNA  length = 28
FEATURE                 Location/Qualifiers
misc_feature            1..28
                        note = Synthetic HBV-probe
modified_base           1
                        mod_base = OTHER
                        note = n=Fluorescein-c
modified_base           9
                        mod_base = OTHER
                        note = n=t-ZEN quencher
modified_base           28
                        mod_base = OTHER
                        note = n=c-3' Iowa Black FQ
source                  1..28
                        mol_type = other DNA
                        organism = synthetic construct
SEQUENCE: 3
nctctkcanc ctgctgctat gcctcatn                                     28
```

BICYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application Nos. 63/363,302, filed Apr. 20, 2022, and 63/484,141, filed Feb. 9, 2023.

SEQUENCE STATEMENT

This application contains a Sequence Listing, which has been submitted electronically and is hereby incorporated by reference in its entirety. The sequence listing, was created on Apr. 18, 2023, is named ALIG_085.xml and is 12 kb in size, and further updated by a file entitled "2023-07-14-Sequence_Listing-ALIG085A.xml", which was created on Jul. 14, 2023, and is approximately 6,467 bytes in size.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroalkyl, hydroxy, alkoxyalkyl, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, C-amido(alkyl), isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amine, a di-substituted amine, an unsubstituted C-amido($C_{1-3}$ alkyl), —O-(an unsubstituted $C_{1-4}$ alkyl)-OH, —O-(an unsubstituted $C_{1-4}$ alkyl)-(an unsubstituted alkoxy), —O-(an unsubstituted $C_{1-4}$ alkyl)-(an unsubstituted C-carboxy), —O—($C_{1-3}$ alkyl)-O-(an unsubstituted C-amido), —O-(an unsubstituted $C_{1-4}$ alkyl)-$NH_2$, —O-(an unsubstituted $C_{1-4}$ alkyl)-NH(an unsubstituted $C_{1-4}$ alkyl), —O-(an unsubstituted $C_{1-4}$ alkyl)-N(an unsubstituted $C_{1-4}$ alkyl)$_2$ and an unsubstituted —O-(an unsubstituted $C_{1-4}$ alkyl)-CN.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2, 3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refers to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted." Further, when a lower alkylene group is substituted, the lower alkylene can be substituted by replacing both hydrogens on the same carbon with a cycloalkyl group

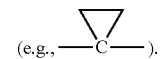

(e.g., —C—).

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR, wherein R is an unsubstituted C$_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by an alkoxy group. Exemplary alkoxyalkyl groups include but are not limited to, methoxymethyl, ethoxymethyl, methoxyethyl and ethoxyethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group and O-monocyclic cycloalkyl group in which one or more of the hydrogen atoms are replaced by a halogen (e.g., mono-haloalkoxy, di-haloalkoxy and tri-haloalkoxy). In some instances, a haloalkoxy can be —OR, wherein R is a C$_{1-4}$ alkyl substituted by 1, 2 or 3 halogens. Such groups include but are not limited to, chloromethoxy, fluoromethoxy, difluoromethoxy, trifluoro-2-ethoxy, trifluoromethoxy, 1-chloro-2-fluoromethoxy, 2-fluoroisobutoxy, chloro-substituted cyclopropyl, fluoro-substituted cyclopropyl, chloro-substituted cyclobutyl and fluoro-substituted cyclobutyl. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—SCN" group.

An "isothiocyanato" group refers to an "—NCS" group.

A "mercapto" group refers to an "—SH" group.

A "carbonyl" group refers to a —C(=O)— group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

A "mono-substituted amine" refers to a "—NHR$_A$" in which R$_A$ can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NHR$_A$, wherein R$_A$ can be an unsubstituted C$_{1-6}$ alkyl or an unsubstituted or a substituted benzyl.

A "di-substituted amine" refers to a "—NR$_A$R$_B$" in which R$_A$ and R$_B$ can be independently can be independently alkyl, alkenyl, alkynyl, cycloalkyl, cycloalkenyl, aryl, heteroaryl, heterocyclyl, aryl(alkyl), heteroaryl(alkyl) or heterocyclyl(alkyl). A mono-substituted amine may be substituted or unsubstituted. In some instances, a mono-substituted amine can be —NR$_A$R$_B$, wherein R$_A$ and R$_B$ can be independently an unsubstituted C$_{1-6}$ alkyl or an unsubstituted or a substituted benzyl.

The term "halogen atom" or "halogen" as used herein, means any one of the radio-stable atoms of column 7 of the Periodic Table of the Elements, such as, fluorine, chlorine, bromine and iodine.

Where the numbers of substituents are not specified (e.g., haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of I-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

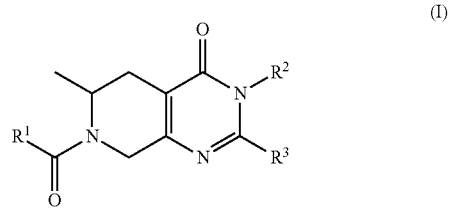

Wherein: $R^1$ can be a substituted phenyl; $R^2$ can be selected from

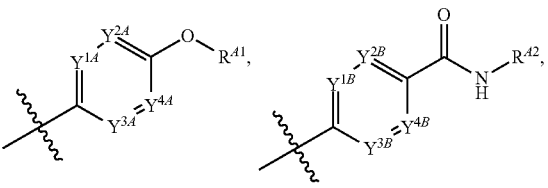

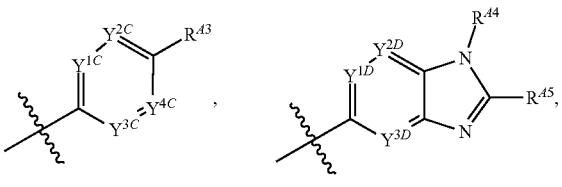

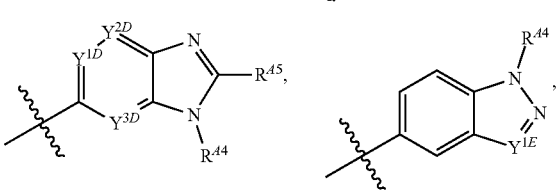

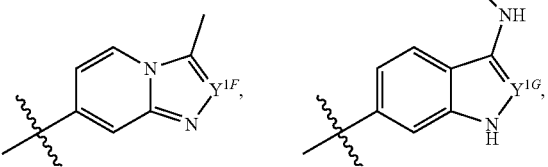

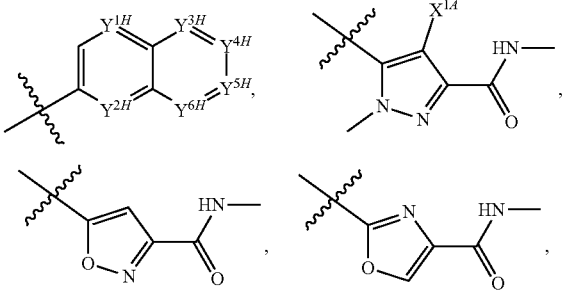

-continued

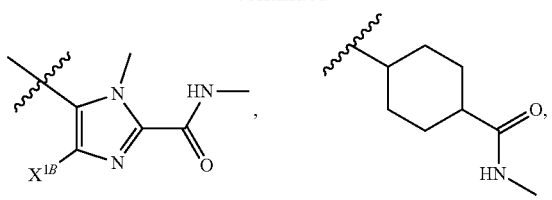

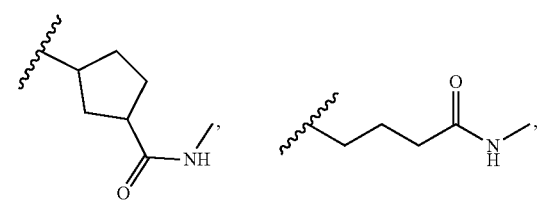

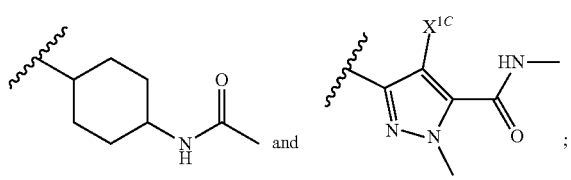

R³ can be selected from a substituted

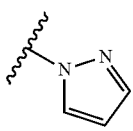

and an unsubstituted or a substituted

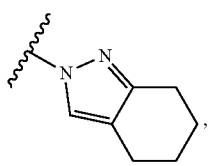 [SMILES: *n1cc2c(n1)CCCC2]

wherein when R³ is a substituted

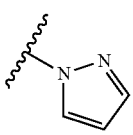 [SMILES: *n1cccn1]

or a substituted

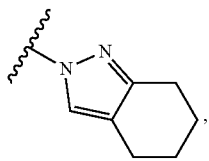 [SMILES: *n1cc2c(n1)CCCC2]

the

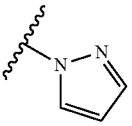 [SMILES: *n1cccn1]

can be substituted 2 or 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH₂, —C(=O)NH(an unsubstituted $C_{1-4}$ alkyl) and —C(=O)N(an unsubstituted $C_{1-4}$ alkyl)₂; the

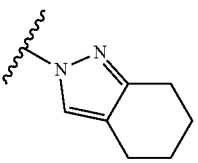 [SMILES: *n1cc2c(n1)CCCC2]

can be substituted 1, 2 or 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH₂, —C(=O)NH(an unsubstituted $C_{1-4}$ alkyl) and —C(=O)N(an unsubstituted $C_{1-4}$ alkyl)₂; and provided that R³ is not

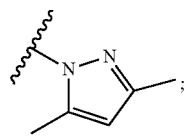 [SMILES: *n1nc(C)cc1C]

;

$X^{1A}$, $X^{1B}$ and $X^{1C}$ can be independently selected from hydrogen, halogen, an unsubstituted $C_{1-5}$ alkyl and an unsubstituted $C_{1-5}$ haloalkyl; $Y^{1A}$ can be CH, C—CHF₂, C—F, C—Cl, C(NH₂), C(NH(unsubstituted $C_{1-5}$ alkyl)), C(N(unsubstituted $C_{1-5}$ alkyl)₂) or N; $Y^{2A}$ can be CH, C-halogen, C—OCH₃, C(NH₂), C(NH(unsubstituted $C_{1-5}$ alkyl)), C(N(unsubstituted $C_{1-5}$ alkyl)₂) or N; $Y^{3A}$ can be CH or N; $Y^{4A}$ can be CH or N; $Y^{1B}$ can be CH, C—CHF₂, C—F, C—Cl, C(NH₂), C(NH(unsubstituted $C_{1-5}$ alkyl)), C(N(unsubstituted $C_{1-5}$ alkyl)₂) or N (nitrogen); $Y^{2B}$ can be CH, C-halogen, C—OCH₃, C(NH₂), C(NH(unsubstituted $C_{1-5}$ alkyl)), C(N(unsubstituted $C_{1-5}$ alkyl)₂) or N (nitrogen); $Y^{3B}$ can be CH or N (nitrogen); $Y^{4B}$ can be CH or N (nitrogen); $Y^{1C}$ $Y^{2C}$, $Y^{3C}$ and $Y^{4C}$ can be each independently CH, C-(halogen) or N (nitrogen); $Y^{1D}$ can be CH, C—CH₃, C—OCH₃, C-(halogen), C—CHF₂, C—CF₃ or N (nitrogen); $Y^{2D}$ can be CH, C—CH₃, C—OCH₃, C-(halogen), C—CHF₂, C—CF₃ or N (nitrogen); $Y^{3D}$ can be CH, C-(halogen) or N (nitrogen); $Y^{1E}$, $Y^{1F}$ and $Y^{1G}$ can be each independently CH, C-(halogen) or N (nitrogen); $Y^{1H}$ $Y^{2H}$, $Y^{3H}$, $Y^{4H}$, $Y^{5H}$ and $Y^{6H}$ can be each independently CH, C-(halogen) or N (nitrogen); $R^{41}$ can be hydrogen, an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —NH$_2$, an unsubstituted C$_{1-5}$ alkoxy, an unsubstituted —NH(an unsubstituted C$_{1-5}$ alkyl), —N(an unsubstituted C$_{1-5}$ alkyl)$_2$, —C(=O)NH$_2$, —O—P(=O)(OH)$_2$, an unsubstituted 5- or 6-membered monocyclic heterocyclyl and 5- or 6-membered monocyclic heterocyclyl substituted by one or more unsubstituted C$_{1-4}$ alkyl groups; R$^{42}$ can be —CH$_3$ or —CD$_3$; R$^{43}$ can be —NH(an unsubstituted or a substituted C$_{1-5}$ alkyl), —N(an unsubstituted or a substituted C$_{1-5}$ alkyl)$_2$, —NH(an unsubstituted or a substituted C$_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl; R$^{44}$ can be an unsubstituted or a substituted C$_{1-5}$ alkyl, an unsubstituted C$_{1-5}$ haloalkyl or an unsubstituted or a substituted monocyclic C$_{3-6}$ cycloalkyl, wherein when the C$_{1-5}$ alkyl and the monocyclic C$_{3-6}$ cycloalkyl are substituted, the C$_{1-5}$ alkyl and the C$_{3-6}$ cycloalkyl can be substituted with one or more groups selected from hydroxy, —C(=O)OH and —C(=O)NH$_2$; and R$^{45}$ can be selected from hydrogen, halogen, —CN, —OH, —NH$_2$, —C(=O)OH, —CH=CH$_2$, an unsubstituted C$_{1-5}$ alkyl, and an unsubstituted or a substituted monocyclic C$_{3-6}$ cycloalkyl, wherein when the monocyclic C$_{3-6}$ cycloalkyl is substituted, the C$_{3-6}$ cycloalkyl can be substituted with one or more hydroxy groups.

As provided herein, R$^1$ can be a substituted phenyl. In some embodiments, R$^1$ can be a mono-substituted phenyl. In other embodiments, R$^1$ can be a di-substituted phenyl. In still other embodiments, R$^1$ can be a tri-substituted phenyl. Exemplary R$^1$ groups include, but are not limited to, the following:

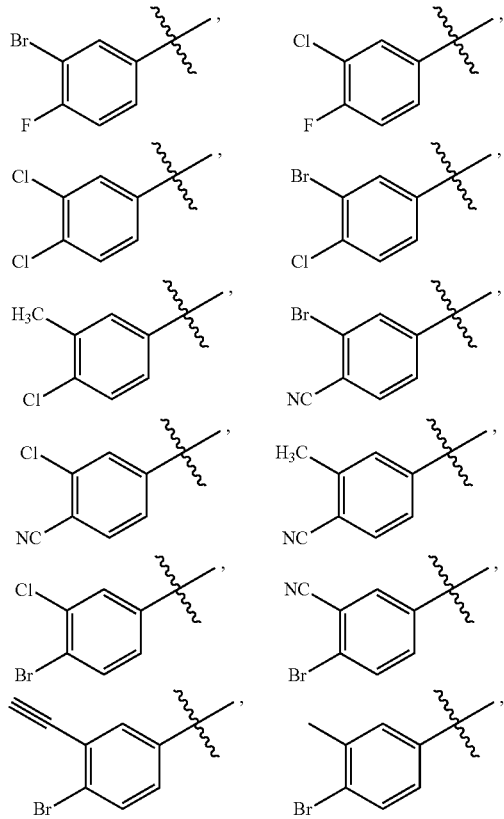

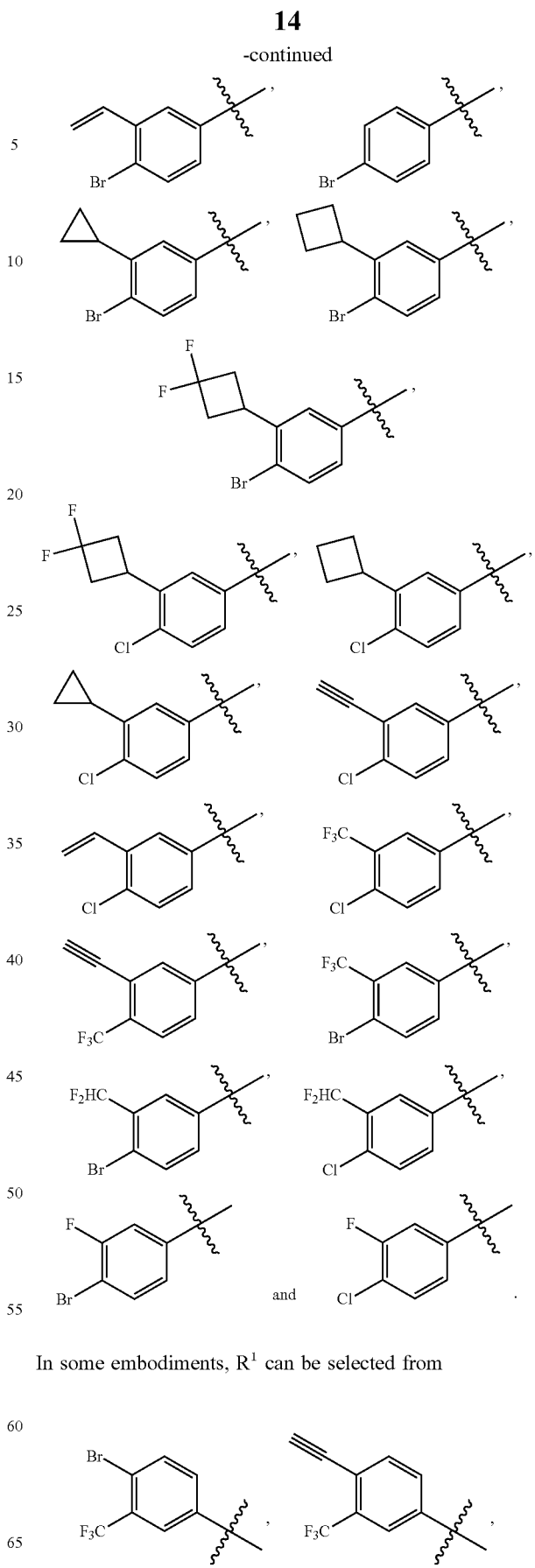

In some embodiments, R$^1$ can be selected from

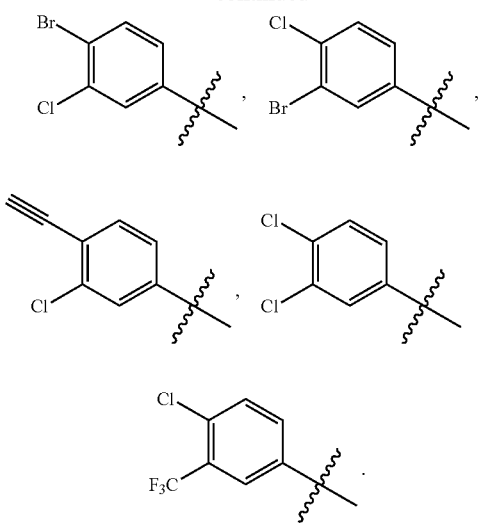

In various embodiments, R² in Formula (I) can be selected from

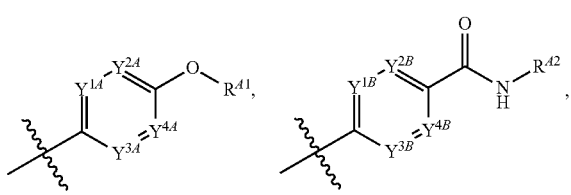

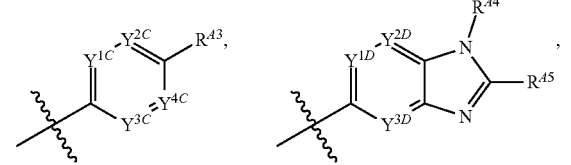

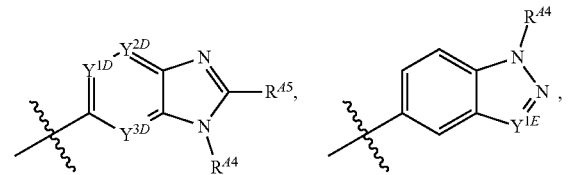

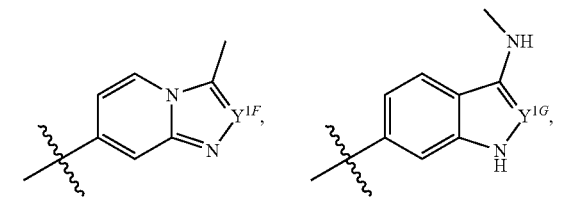

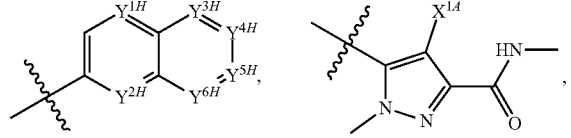

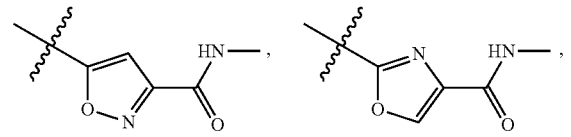

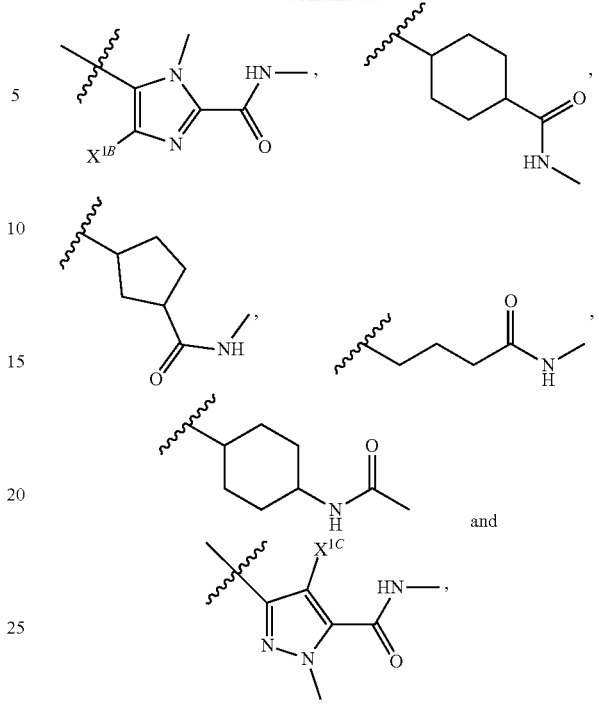

wherein the variables $X^{1A}$, $X^{1B}$, $X^{1C}$, $Y^{1A}$, $Y^{2A}$, $Y^{3A}$, $Y^{4A}$, $Y^{1B}$, $Y^{2B}$, $Y^{3B}$, $Y^{4B}$, $Y^{1C}$, $Y^{2C}$, $Y^{3C}$, $Y^{4C}$, $Y^{1D}$, $Y^{2D}$, $Y^{3D}$, $Y^{1E}$, $Y^{1F}$, $Y^{1G}$, $Y^{1H}$, $Y^{2H}$, $Y^{3H}$, $Y^{4H}$, $Y^{5H}$, $Y^{6H}$, $R^{A1}$, $R^{A2}$, $R^{A3}$, $R^{A4}$, and, $R^{A5}$, can, be, as, defined, elsewhere, herein.

In some embodiments, R² in Formula (I) can be

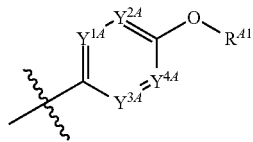

where $R^{A1}$ can be an unsubstituted $C_{1-5}$ alkyl. For example, $R^{A1}$ can be methyl, ethyl, n-propyl, iso-propyl, n-butyl, iso-butyl, sec-butyl, tert-butyl, n-pentyl or a branched pentyl. In still other embodiments, R² in Formula (I) can be

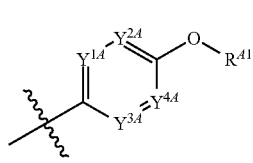

where $R^{A1}$ can be a substituted $C_{1-5}$ alkyl. As provided herein, a $C_{1-5}$ alkyl for $R^{A1}$ can be substituted with one or more hydroxy groups (such as 1, 2 or 3 hydroxy groups), one or more —NH₂ groups (for example, 1, 2 or 3 —NH₂ groups), one or more an unsubstituted $C_{1-5}$ alkoxy groups (such as 1, 2 or 3 alkoxy groups), one or more an unsubstituted —NH(an unsubstituted $C_{1-5}$ alkyl) groups (such as 1, 2 or 3 —NH(an unsubstituted $C_{1-5}$ alkyl) groups), one or more —N(an unsubstituted $C_{1-5}$ alkyl)₂ (for example, 1, 2 or 3 —N(an unsubstituted $C_{1-5}$ alkyl)₂ groups), one or more —C(=O)NH₂ (for example, 1 or 2 —C(=O)NH₂ groups), one or more —O—P(=O)(OH)$_2$ (for example, 1 or 2 —O—P(=O)(OH)$_2$ groups), one or more unsubstituted 5- or 6-membered monocyclic heterocyclyls (for example, 1, 2 or 3 unsubstituted 5- or 6-membered monocyclic heterocyclyls) and/or one or more 5- or 6-membered monocyclic heterocyclyls substituted by one or more unsubstituted C$_{1-4}$ alkyl groups (for example, 1, 2 or 3 5- or 6-membered monocyclic heterocyclyls each independently substituted with 1, 2 or 3 unsubstituted C$_{1-4}$ alkyl groups). Exemplary C$_{1-5}$ alkyls substituted with one or more hydroxy groups include —CH$_2$CH$_2$OH, —CH$_2$CH(CH$_3$)OH and —CH$_2$CH(OH)CH$_2$(OH). As provided herein, a C$_{1-5}$ alkyl for R$^{A1}$ can be substituted by one or more —NH$_2$ groups, one or more —NH(an unsubstituted C$_{1-5}$ alkyl) groups and/or one or more —N(an unsubstituted C$_{1-5}$ alkyl)$_2$ groups. For example, R$^{A1}$ can be —(CH$_2$)$_{1-4}$NH$_2$, —(CH$_2$)$_{1-4}$NH(an unsubstituted C$_{1-5}$ alkyl) or —(CH$_2$)$_{1-4}$N(an unsubstituted C$_{1-5}$ alkyl)$_2$. Examples of C$_{1-5}$ alkyls substituted with one or more unsubstituted C$_{1-5}$ alkoxy groups include —CH$_2$CH$_2$OCH$_3$ and —CH$_2$CH(CH$_3$)OCH$_3$. An example of an C$_{1-5}$ alkyl substituted with —C(=O)NH$_2$ is —CH$_2$—C(=O)NH$_2$. An example of an C$_{1-5}$ alkyl substituted with —O—P(=O)(OH)$_2$ is —CH$_2$CH(O—P(=O)(OH)$_2$)CH$_3$. An example of an C$_{1-5}$ alkyl substituted with —O—P(=O)(OH)$_2$ is —CH$_2$CH(O—P(=O)(OH)$_2$)(CH$_3$). In some embodiments, R$^{A1}$ can be a C$_{1-5}$ alkyl substituted with one moiety selected from hydroxy, —NH$_2$, an unsubstituted C$_{1-5}$ alkoxy, an unsubstituted —NH(an unsubstituted C$_{1-5}$ alkyl), —N(an unsubstituted C$_{1-5}$ alkyl)$_2$, —C(=O)NH$_2$ and —O—P(=O)(OH)$_2$. For example, R$^{A1}$ can be —(CH$_2$)$_{1-4}$OH, —(CH$_2$)$_{1-2}$CH(CH$_3$)(OH), —CH$_2$CH(OH)CH$_2$(OH), —(CH$_2$)$_{1-4}$NH$_2$, —(CH$_2$)$_{1-4}$NH(an unsubstituted C$_{1-5}$ alkyl) or —(CH$_2$)$_{1-4}$N(an unsubstituted C$_{1-5}$ alkyl)$_2$, —(CH$_2$)$_{1-4}$OCH$_3$, —(CH$_2$)$_{1-4}$C(=O)NH$_2$, —(CH$_2$)$_{1-4}$(O—P(=O)(OH)$_2$) and —(CH$_2$)$_{1-2}$CH(O—P(=O)(OH)$_2$)(CH$_3$). In some embodiments, R$^{A1}$ can be a C$_{1-5}$ alkyl substituted with an unsubstituted 5- or 6-membered monocyclic heterocyclyls and/or a 5- or 6-membered monocyclic heterocyclyls substituted by one or more unsubstituted C$_{1-4}$ alkyl groups. Exemplary 5- or 6-membered monocyclic heterocyclyls that can be substituted on a C$_{1-5}$ alkyl include pyrrolidinyl, piperidinyl, morpholinyl, 1,2,4-oxadiazol-5(4H)-one, 2,4-dihydro-3H-1,2,4-triazol-3-onyl, pyrazolonyl and piperazinyl. In other embodiments, R$^2$ in Formula (I) can be

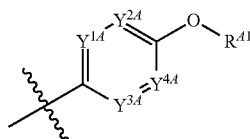

where R$^{A1}$ can be an unsubstituted monocyclic C$_{3-6}$ cycloalkyl. In yet still other embodiments, R$^2$ in Formula (I) can be

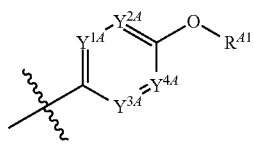

where R$^{A1}$ can be a substituted monocyclic C$_{3-6}$ cycloalkyl substituted with one or more hydroxy groups (such as 1, 2 or 3 hydroxy groups), one or more —NH$_2$ groups (for example, 1, 2 or 3 —NH$_2$ groups), one or more an unsubstituted C$_{1-5}$ alkoxy groups (such as 1, 2 or 3 alkoxy groups), one or more an unsubstituted —NH(an unsubstituted C$_{1-5}$ alkyl) groups (such as 1, 2 or 3 —NH(an unsubstituted C$_{1-5}$ alkyl) groups), one or more —N(an unsubstituted C$_{1-5}$ alkyl)$_2$ (for example, 1, 2 or 3 —N(an unsubstituted C$_{1-5}$ alkyl)$_2$ groups), one or more —C(=O)NH$_2$ (for example, 1 or 2 —C(=O)NH$_2$ groups), one or more —O—P(=O)(OH)$_2$ (for example, 1 or 2 —O—P(=O)(OH)$_2$ groups), one or more unsubstituted 5- or 6-membered monocyclic heterocyclyls (for example, 1, 2 or 3 unsubstituted 5- or 6-membered monocyclic heterocyclyls) and/or one or more 5- or 6-membered monocyclic heterocyclyls substituted by one or more unsubstituted C$_{1-4}$ alkyl groups (for example, 1, 2 or 3 5- or 6-membered monocyclic heterocyclyls each independently substituted with 1, 2 or 3 unsubstituted C$_{1-4}$ alkyl groups). Examples of monocyclic C$_{3-6}$ cycloalkyls include cyclopropyl, cyclobutyl, cyclopentyl and cyclohexyl. In some embodiments, R$^{A1}$ can be a substituted monocyclic C$_{3-6}$ cycloalkyl substituted with one moiety selected from hydroxy, —NH$_2$, an unsubstituted C$_{1-5}$ alkoxy, an unsubstituted —NH(an unsubstituted C$_{1-5}$ alkyl) and —N(an unsubstituted C$_{1-5}$ alkyl)$_2$. In some embodiments, R$^{A1}$ can be cyclobutyl substituted with a moiety selected from hydroxy, —NH$_2$, an unsubstituted —NH(an unsubstituted C$_{1-5}$ alkyl) and —N(an unsubstituted C$_{1-5}$ alkyl)$_2$. In some embodiments, R$^{A1}$ can be hydrogen.

In some embodiments, Y$^{1A}$, Y$^{2A}$, Y$^{3A}$ and Y$^{4A}$ can be each CH. In other embodiments, one of Y$^{1A}$, Y$^{2A}$, Y$^{3A}$ and Y$^{4A}$ can be N. In still other embodiments, two or three of Y$^{1A}$, Y$^{2A}$, Y$^{3A}$ and Y$^{4A}$ can be N. In some embodiments, Y$^{1A}$ can be C—CHF$_2$, C—F or C—Cl; and Y$^{2A}$, Y$^{3A}$ and Y$^{4A}$ can be each CH. In some embodiments, Y$^{2A}$ can be C-halogen. In other embodiments, Y$^{2A}$ can be C—OCH$_3$. In some embodiments, Y$^{2A}$ can be C-halogen; and Y$^{1A}$ Y$^{3A}$ and Y$^{4A}$ can be each CH. In some embodiments, Y$^{2A}$ can be C(NH$_2$), C(NH(unsubstituted C$_{1-5}$ alkyl)) or C(N(unsubstituted C$_{1-5}$ alkyl)$_2$). In other embodiments, Y$^{2A}$ can be C—OCH$_3$; and Y$^{1A}$, Y$^{3A}$ and Y$^{4A}$ can be each CH. In other embodiments, Y$^{2A}$ can be C(NH$_2$), C(NH(unsubstituted C$_{1-5}$ alkyl)) or C(N(unsubstituted C$_{1-5}$ alkyl)$_2$); and Y$^{1A}$, Y$^{3A}$ and Y$^{4A}$ can be each CH. Examples of R$^2$ include the following

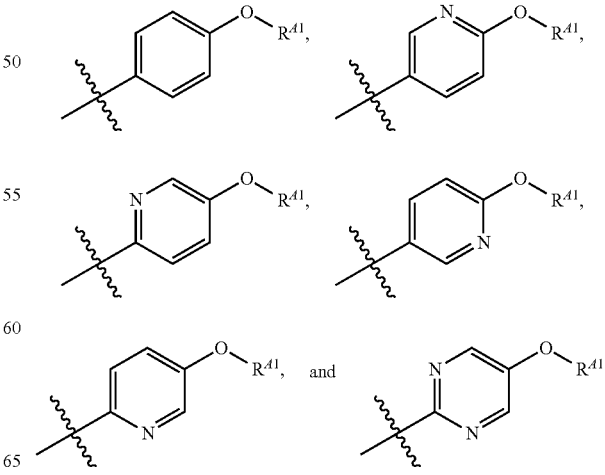

In another embodiment, $R^2$ in Formula (I) can be

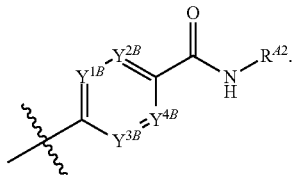

In various embodiments, $Y^{1B}$ can be CH, C—Cl or N; $Y^{2B}$ can be CH, C—Cl, C—OCH$_3$, C(NH$_2$), C(NH(unsubstituted C$_{1-5}$ alkyl)) or C(N(unsubstituted C$_{1-5}$ alkyl)$_2$) or N; $Y^{3B}$ can be CH or N; $Y^{4B}$ can be CH or N; and $R^{A2}$ can be —CH$_3$ or —CD$_3$. In some embodiments, $Y^{1B}$, $Y^{2B}$, $Y^{3B}$ and $Y^{4B}$ can be each CH. In other embodiments, at least one of $Y^{1B}$, $Y^{3B}$ and $Y^{4B}$ can be N (nitrogen). As an example, one of $Y^{1B}$, $Y^{3B}$ and $Y^{4B}$ can be N such that the ring of

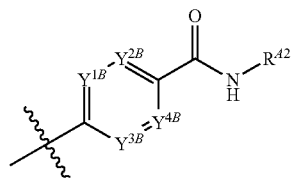

can be pyridinyl. Other examples of rings where at least one of $Y^{1B}$, $Y^{3B}$ and $Y^{4B}$ is nitrogen include pyridazine, pyrimidine and pyrazine. In some embodiments, $Y^{1B}$, $Y^{2B}$, $Y^{3B}$ and $Y^{4B}$ can be each CH. In other embodiments, one of $Y^{1B}$, $Y^{2B}$, $Y^{3B}$ and $Y^{4B}$ can be N. In still other embodiments, two or three of $Y^{1B}$, $Y^{2B}$, $Y^{3B}$ and $Y^{4B}$ can be N. In some embodiments, $Y^{1B}$ can be C—CHF$_2$, C—F or C—Cl; and $Y^{2B}$, $Y^{3B}$ and $Y^{4B}$ can be each CH. In some embodiments, $Y^{2B}$ can be C-halogen. In other embodiments, $Y^{2B}$ can be C—OCH$_3$. In still other embodiments, $Y^{2B}$ can be C(NH$_2$), C(NH(unsubstituted C$_{1-5}$ alkyl)) or C(N(unsubstituted C$_{1-5}$ alkyl)$_2$). In some embodiments, $Y^{2B}$ can be C-halogen (such as C—Cl); and $Y^{1B}$, $Y^{3B}$ and $Y^{4B}$ can be each CH. In other embodiments, $Y^{2B}$ can be C—OCH$_3$; and $Y^{1B}$, $Y^{3B}$ and $Y^{4B}$ can be each CH. In still other embodiments, $Y^{2B}$ can be C(NH$_2$), C(NH(unsubstituted C$_{1-5}$ alkyl)) or C(N(unsubstituted C$_{1-5}$ alkyl)$_2$); and $Y^{1B}$, $Y^{3B}$ and $Y^{4B}$ can be each CH. Exemplary $R^2$ groups include

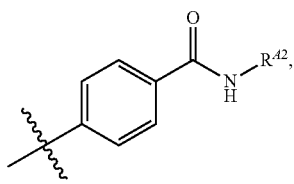

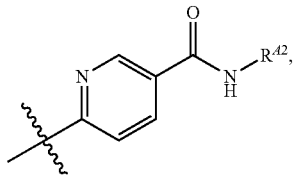

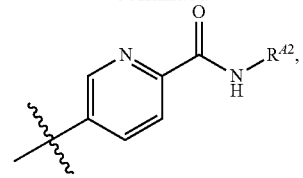

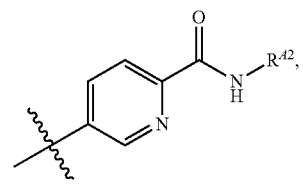

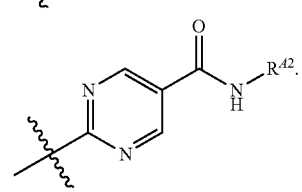

and

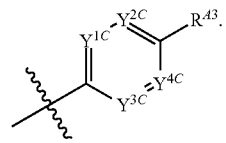

In another embodiment, $R^2$ in Formula (I) can be

In some embodiments, $Y^{1C}$, $Y^{2C}$, $Y^{3C}$ and $Y^{4C}$ can be each independently CH or N (nitrogen); and $R^{A3}$ can be —NH$_2$, —NH(an unsubstituted or a substituted C$_{1-5}$ alkyl), —N(an unsubstituted or a substituted C$_{1-5}$ alkyl)$_2$, —NH(an unsubstituted or a substituted C$_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl. In some embodiments, $R^{A3}$ can be —NH$_2$. In other embodiments, $R^{A3}$ can be —NH(an unsubstituted C$_{1-5}$ alkyl). In still other embodiments, $R^{A3}$ can be —NH(a substituted C$_{1-5}$ alkyl). In yet still other embodiments, —N(an unsubstituted C$_{1-5}$ alkyl)$_2$. In some embodiments, $R^{A3}$ can be —N(a substituted C$_{1-5}$ alkyl)$_2$. Examples of C$_{1-5}$ alkyls include methyl, ethyl, n-propyl, iso-propyl, n-butyl, iso-butyl, sec-butyl, tert-butyl, n-pentyl or a branched pentyl. When the C$_{1-5}$ alkyl is substituted, the C$_{1-5}$ alkyl can be substituted with one or more hydroxy groups, for example, 1, 2 or 3 hydroxy groups. For example, —NH(CH$_2$)$_{1-5}$OH, —NH(CH$_2$)$_{1-4}$CH(OH)(CH$_3$), —NH(CH$_2$)$_{1-3}$CH(OH)CH$_2$(CH$_3$), —NH(CH$_2$)$_{1-3}$CH(OH)CH$_2$(OH) or —NH((CH$_2$)$_{1-5}$OH)$_2$. As provided herein, $R^{A3}$ can be an unsubstituted or a substituted 5- or 6-membered heteroaryl. In some embodiments, $R^{A3}$ can be an unsubstituted or a substituted 5-membered-monocyclic heteroaryl. Non-limiting examples of suitable 5-membered-monocyclic heteroaryls include pyrazolyl, imidazolyl, 1,2,3-triazolyl, 1,2,4-triazolyl and tetrazolyl. In other embodiments, $R^{43}$ can be an unsubstituted or a substituted 6-membered-monocyclic heteroaryl. In some instances, the 5- and/or 6-membered-monocyclic heteroaryl can include 1, 2 or 3 heteroatoms, such as N (nitrogen), O (oxygen) and/or S (sulfur). In some embodiments, $R^{43}$ can be an unsubstituted or a substituted 5- or 6-membered-monocyclic heteroaryl that includes 1 or 2 nitrogens. Non-limiting examples of suitable 5-membered-monocyclic heteroaryls include pyrazolyl, imidazolyl, 1,2,3-triazolyl, 1,2,4-triazolyl and tetrazolyl. Examples of 6-membered monocyclic heteroaryls includes pyridinyl, pyridazinyl, pyrimidinyl and pyrazinyl. In some embodiments, $R^{43}$ can be an unsubstituted or a substituted 4-membered-monocyclic heterocyclyl. In other embodiments, $R^{43}$ can be an unsubstituted or a substituted 5-membered-monocyclic heterocyclyl. In yet still other embodiments, $R^{43}$ can be an unsubstituted or a substituted 6-membered-monocyclic heterocyclyl. In some instances, the 4- to 6-membered-monocyclic heterocyclyl can include 1, 2 or 3 heteroatoms N (nitrogen), O (oxygen) and/or S (sulfur). In some embodiments, $R^{43}$ can be an unsubstituted or a substituted 4- to 6-membered-monocyclic heterocyclyl that includes 1 or 2 nitrogens. Non-limiting examples of suitable 4- to 6-membered-monocyclic heterocyclyls include azetidinyl, pyrrolidinyl, morpholinyl, 1,2,4-oxadiazol-5(4H)-onyl, 2,4-dihydro-3H-1,2,4-triazol-3-onyl, pyrazolonyl and piperazinyl. Possible substitutions that can be present on a —NH(a substituted $C_{3-6}$ monocyclic cycloalkyl), a substituted monocyclic heteroaryl and/or a substituted monocyclic heterocyclyl of $R^{43}$ include halogen, hydroxy, amino, an unsubstituted $C_{1-6}$ alkyl and an unsubstituted $C_{1-6}$ haloalkyl.

In some embodiments, $Y^{1C}$, $Y^{2C}$, $Y^{3C}$ and $Y^{4C}$ can be each CH such that $R^2$ can be

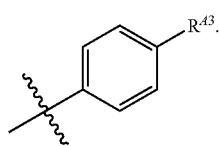

In other embodiments, at least one of $Y^{1C}$, $Y^{2C}$, $Y^{3C}$ and $Y^{4C}$ can be N (nitrogen). Exemplary rings for

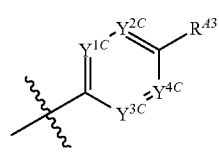

when at least one of $Y^{1C}$, $Y^{2C}$, $Y^{3C}$ and $Y^{4C}$ is N include pyridinyl, pyridazine, pyrimidine and pyrazine. In some embodiments, $Y^{1C}$, $Y^{2C}$, $Y^{3C}$ and $Y^{4C}$ can be each CH. In other embodiments, one of $Y^{1C}$, $Y^{2C}$, $Y^{3C}$ and $Y^{4C}$ can be N. In still other embodiments, $Y^{2C}$ is CH, C—F or C—Cl. In yet still other embodiments, two or three of $Y^{1C}$, $Y^{2C}$, $Y^{3C}$ and $Y^{4C}$ can be N. In some embodiments, one of $Y^{1C}$, $Y^{2C}$, $Y^{3C}$ and $Y^{4C}$ can be C-(halogen). Examples of $R^2$ include the following

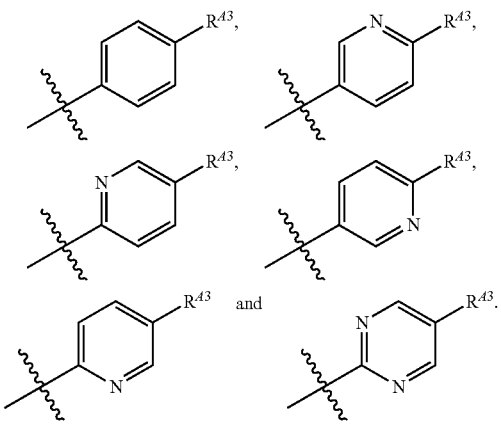

In another embodiment, $R^2$ in Formula (I) can be

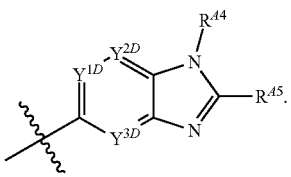

In still another embodiment, $R^2$ in Formula (I) can be

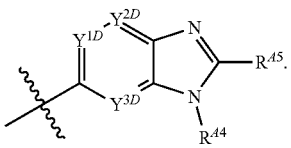

In various embodiments, $Y^{1D}$ can be CH, C—CH$_3$, C—OCH$_3$, C-(halogen), C—CHF$_2$, C—CF$_3$ or N; $Y^{2D}$ can be CH, C—CH$_3$, C—OCH$_3$, C-(halogen), C—CHF$_2$, C—CF$_3$ or N; $Y^{3D}$ can be CH, C-(halogen) or N; $R^{44}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(=O)OH and —C(=O)NH$_2$; and $R^{45}$ can be selected from hydrogen, halogen, —CN, —OH, —NH$_2$, —C(=O)OH, —CH=CH$_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

In some embodiments, $Y^{1D}$, $Y^{2D}$ and $Y^{3D}$ can be each CH. In other embodiments, one of $Y^{1D}$ and $Y^{2D}$ can be CH; the other of $Y^{1D}$ and $Y^{2D}$ can be C—CH$_3$, C—OCH$_3$, C-(halogen), C—CHF$_2$, C—CF$_3$; and $Y^{3D}$ can be CH. In still other embodiments, one of $Y^{1D}$ and $Y^{2D}$ can be CH; the other of $Y^{1D}$ and $Y^{2D}$ can be C—CH$_3$, C—OCH$_3$, C-(halogen), C—CHF$_2$, C—CF$_3$; and $Y^{3D}$ can be N (nitrogen). The halogen of C-(halogen) can be F, Cl, Br of I. In some embodiments, $Y^{2D}$ can be N. In some embodiments, $Y^{3D}$ can be N. In some embodiments, $Y^{2D}$ and $Y^{3D}$ can be each N. In some embodiments, C-(halogen) of $Y^{1D}$ and/or $Y^{2D}$ can be C—F or C—Cl. In some embodiments, $R^{44}$ can be an unsubstituted C$_{1-5}$ alkyl. In other embodiments, R$^{A4}$ can be a substituted C$_{1-5}$ alkyl. In still other embodiments, R$^{A4}$ can be an unsubstituted C$_{1-5}$ haloalkyl. In yet still other embodiments, R$^{A4}$ can be an unsubstituted cyclopropyl, an unsubstituted cyclobutyl, an unsubstituted cyclopentyl or an unsubstituted cyclohexyl. In some embodiments, R$^{A4}$ can be a substituted monocyclic C$_{3-6}$ cycloalkyl, substituted with one or more (such as 1, 2 or 3) hydroxy groups. Examples of C$_{1-5}$ alkyls for R$^{A4}$ include methyl, ethyl, n-propyl, iso-propyl, n-butyl, iso-butyl, sec-butyl, tert-butyl, n-pentyl or a branched pentyl. As provided herein, a C$_{1-5}$ alkyl for R$^{A4}$ can be substituted with one or more hydroxy groups (such as 1, 2 or 3 hydroxy groups), one or more —C(=O)OH groups (for example, 1, 2 or 3 —C(=O)OH groups) and/or one or more —C(=O)NH$_2$ groups, such as 1, 2 or 3 —C(=O)NH$_2$ groups. Exemplary C$_{1-5}$ alkyls substituted with one or more hydroxy groups, one or more —C(=O)OH groups and/or one or more —C(=O)NH$_2$ groups include, —CH$_2$CH$_2$OH, —CH(CH$_3$)OH, —CH$_2$CH(CH$_3$)OH, —CH$_2$C(=O)NH$_2$, —CH$_2$CH$_2$C(=O)NH$_2$, —CH(CH$_3$)C(=O)NH$_2$, —CH$_2$CH(CH$_3$)C(=O)NH$_2$, —CH$_2$C(=O)OH, —CH$_2$CH$_2$C(=O)OH, —CH(CH$_3$)C(=O)OH and —CH$_2$CH(CH$_3$)C(=O)OH. Examples of C$_{1-5}$ haloalkyls include —CF$_3$, —CCl$_3$, —CHF$_2$, —C(CH$_3$)F$_2$, —CHCl$_2$, —CH$_2$F, —CH(CH$_3$)F, —CH$_2$CH$_2$F, —CH$_2$CHF$_2$, —CH$_2$CF$_3$, —CH$_2$Cl, —CH$_2$CH$_2$F, —CH$_2$CH$_2$Cl, —CH$_2$CH$_2$CH$_2$F and —CH$_2$CH$_2$CH$_2$Cl.

In some embodiments, R$^{A5}$ can be hydrogen. In some embodiments, R$^{A5}$ can be halogen, —CN, —OH or —NH$_2$. In still other embodiments, R$^{A5}$ can be —C(=O)OH. In yet still other embodiments, R$^{A5}$ can be —CH=CH$_2$. In some embodiments, R$^{A5}$ can be an unsubstituted C$_{1-5}$ alkyl, such as methyl, ethyl, n-propyl, iso-propyl, n-butyl, iso-butyl, sec-butyl, tert-butyl, n-pentyl or a branched pentyl. In other embodiments, R$^{A5}$ can be an unsubstituted C$_{3-6}$ cycloalkyl. In other embodiments, R$^{A5}$ can be a substituted monocyclic C$_{3-6}$ cycloalkyl substituted with one or more (for example, 1, 2 or 3) hydroxy groups. The cycloalkyl for R$^{A5}$ can be cyclopropyl, cyclobutyl, cyclopentyl or cyclohexyl.

In another embodiment, R$^2$ in Formula (I) can be

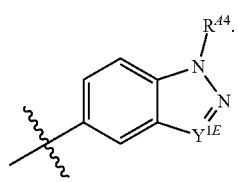

In various embodiments, Y$^{1E}$ can be CH. In other various embodiments, Y$^{1E}$ can be N (nitrogen). In some embodiments, R$^{A4}$ can be an unsubstituted or a substituted C$_{1-5}$ alkyl. In other embodiments, R$^{A4}$ can be an unsubstituted C$_{1-5}$ haloalkyl. In still other embodiments, R$^{A4}$ can be an unsubstituted or a substituted monocyclic C$_{3-6}$ cycloalkyl. For example, R$^{A4}$ can be selected from methyl, ethyl, n-propyl, iso-propyl, n-butyl, iso-butyl, sec-butyl, tert-butyl, n-pentyl, a branched pentyl, —CF$_3$, —CCl$_3$, —CHF$_2$, —C(CH$_3$)F$_2$, —CHCl$_2$, —CH$_2$F, —CH(CH$_3$)F, —CH$_2$CH$_2$F, —CH$_2$CHF$_2$, —CH$_2$CF$_3$, —CH$_2$Cl, —CH$_2$CH$_2$F, —CH$_2$CH$_2$Cl, —CH$_2$CH$_2$CH$_2$F, —CH$_2$CH$_2$CH$_2$Cl, cyclopropyl, cyclobutyl, cyclopentyl and cyclohexyl. Possible substitutions that can be present on a substituted monocyclic C$_{3-6}$ cycloalkyl include halogen, hydroxy, an unsubstituted C$_{1-6}$ alkyl and an unsubstituted C$_{1-6}$ haloalkyl, and possible substitutions that can be present on a substituted C$_{1-5}$ alkyl include halogen, hydroxy and an unsubstituted C$_{1-6}$ haloalkyl.

In another embodiment, R$^2$ in Formula (I) can be

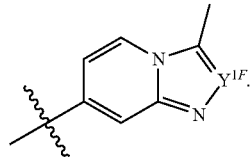

In some embodiments, Y$^{1F}$ can be CH. In other embodiments, Y$^{1F}$ can be N (nitrogen).

In another embodiment, R$^2$ in Formula (I) can be

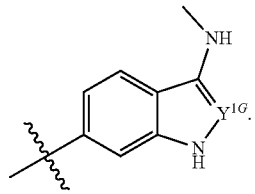

In some embodiments, R$^2$ in Formula (I) can be

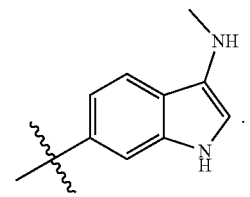 [SMILES: *c1ccc2c(NC)c[nH]c2c1]

In other embodiments, R$^2$ in Formula (I) can be

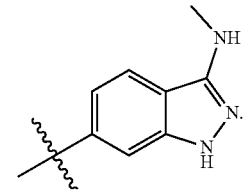 [SMILES: *c1ccc2c(NC)n[nH]c2c1]

In another embodiment, R$^2$ in Formula (I) can be

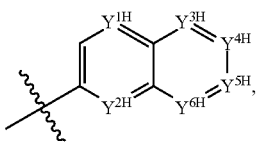

wherein Y$^{1H}$, Y$^{2H}$, Y$^{3H}$, Y$^{4H}$, Y$^{5H}$ and Y$^{6H}$ are each independently CH, C-(halogen) or N (nitrogen). In some embodiments, one of Y$^{1H}$ and Y$^{2H}$ can be N. In other embodiments, each of Y$^{1H}$ and Y$^{2H}$ can be N. In some embodiments, including those of this paragraph, one of Y$^{3H}$, Y$^{4H}$, Y$^{5H}$ and Y$^{6H}$ can be N. In other embodiments, including those of this paragraph, two of $Y^{3H}$, $Y^{4H}$, $Y^{5H}$ and $Y^{6H}$ can be N. In still other embodiments, including those of this paragraph, three or four of $Y^3H$ $Y^4H$ $Y^5H$ and $Y^{6H}$ can be N. Examples of

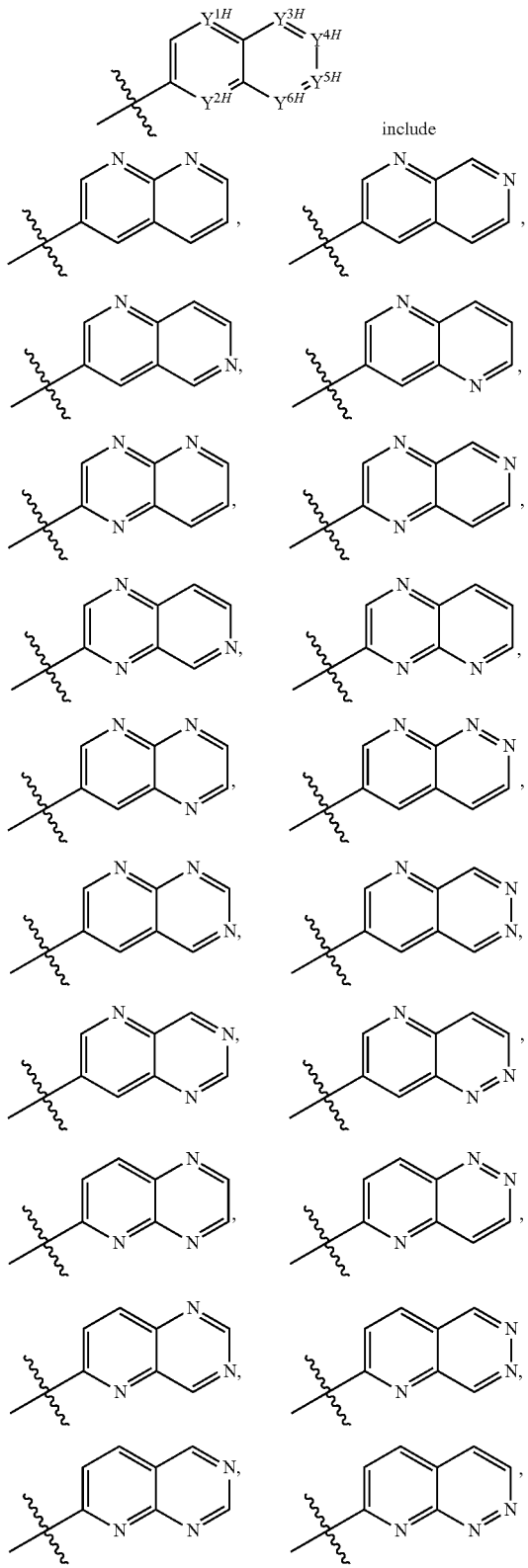

include

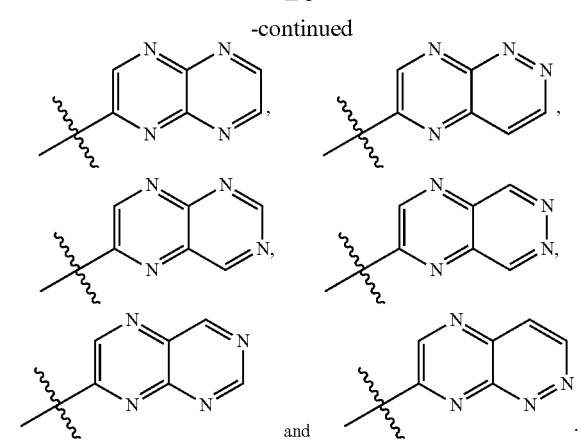

In another embodiment, $R^2$ in Formula (I) can be

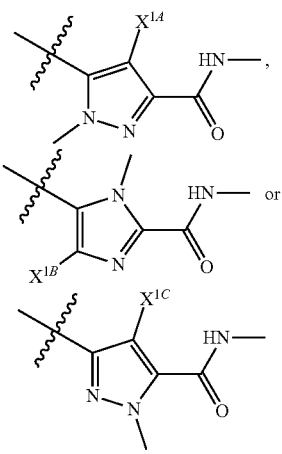

where $X^{1A}$, $X^{1B}$ and $X^{1C}$ can be independently selected from hydrogen, halogen (F, Cl and Br), an unsubstituted $C_{1-5}$ alkyl (such as methyl, ethyl, n-propyl, iso-propyl, n-butyl, iso-butyl, tert-butyl, n-pentyl (straight and branched version) and an unsubstituted $C_{1-5}$ haloalkyl ($CF_3$, $-CCl_3$, $-CHF_2$, $-C(CH_3)F_2$, $-CHCl_2$, $-CH_2F$, $-CH(CH_3)F$, $-CH_2CH_2F$, $-CH_2CHF_2$, $-CH_2CF_3$, $-CH_2Cl$, $-CH_2CH_2F$, $-CH_2CH_2Cl$, $-CH_2CH_2CH_2F$, $-CH_2CH_2CH_2Cl$). In some embodiments, $R^2$ can be

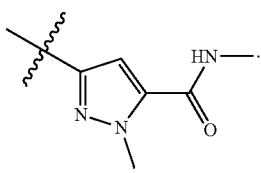 [SMILES: *c1cc(C(=O)NC)n(C)n1]

In another embodiment, $R^2$ in Formula (I) can be

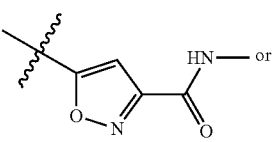

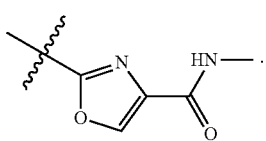

In another embodiment, R² in Formula (I) can be

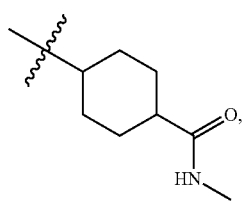

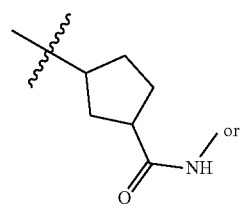

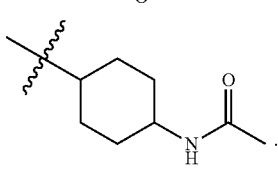

In another embodiment, R² in Formula (I) can be

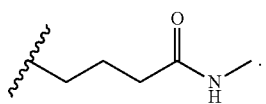 [SMILES: *CCCC(=O)NC]

In some embodiments, R² can be

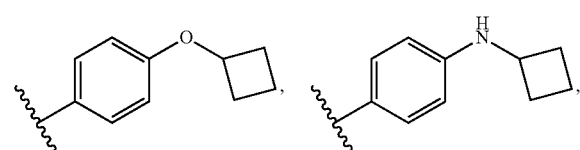

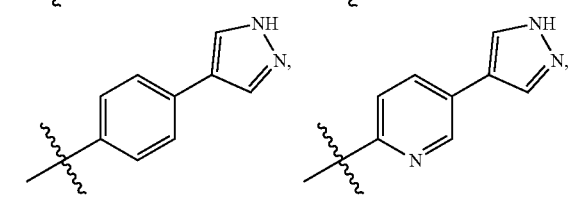

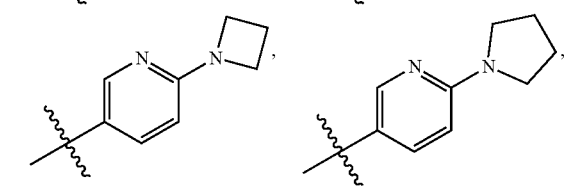

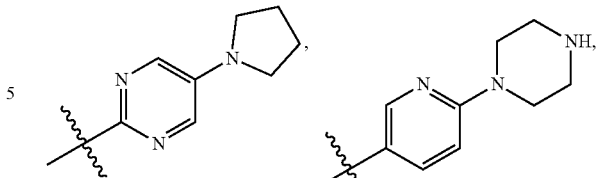

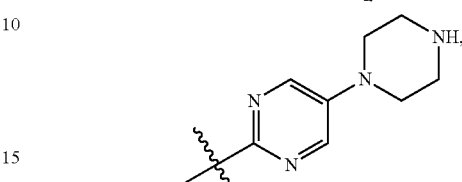

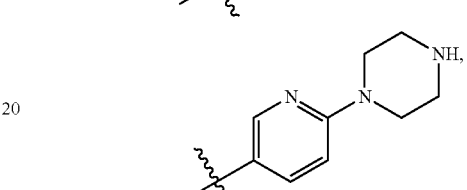

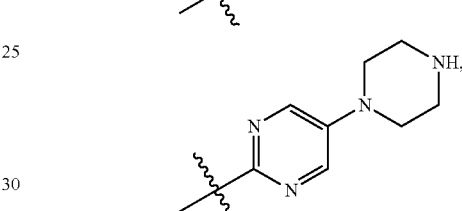

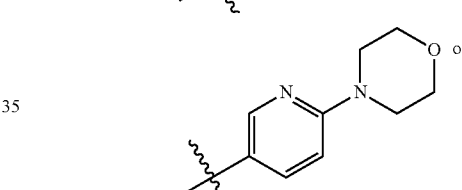

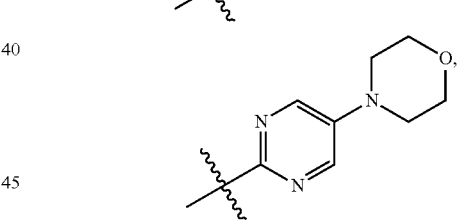

wherein each can be optionally substituted with one or more moieties (1, 2 or 3 moieties) independently selected from halogen, hydroxy, amino, an unsubstituted $C_{1-6}$ alkyl and an unsubstituted $C_{1-6}$ haloalkyl. In some embodiments, a hydrogen on a carbon can be replaced with halogen, hydroxy, amino, an unsubstituted $C_{1-6}$ alkyl or an unsubstituted $C_{1-6}$ haloalkyl and/or the hydrogen of a NH group can be replaced with an unsubstituted $C_{1-6}$ alkyl or an unsubstituted $C_{1-6}$ haloalkyl. Suitable halogens, unsubstituted $C_{1-6}$ alkyl and $C_{1-6}$ haloalkyls are provided herein and include F, Cl, methyl, ethyl, n-propyl, iso-propyl, n-butyl, iso-butyl, sec-butyl, tert-butyl, pentyl (straight-chained or branched), hexyl (straight-chained or branched), —$CF_3$, —$CCl_3$, —$CHF_2$, —$C(CH_3)F_2$, —$CHCl_2$, —$CH_2F$, —$CH(CH_3)F$, —$CH_2CH_2F$, —$CH_2CHF_2$, —$CH_2CF_3$, —$CH_2Cl$, —$CH_2CH_2F$, —$CH_2CH_2Cl$, —$CH_2CH_2CH_2F$, —$CH_2CH_2CH_2Cl$. Exemplary R² groups include Exemplary R² groups include -continued -continued
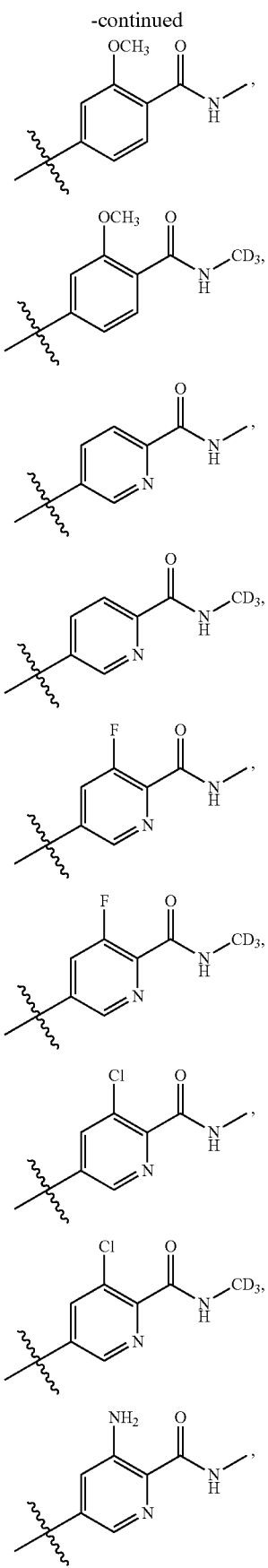
-continued
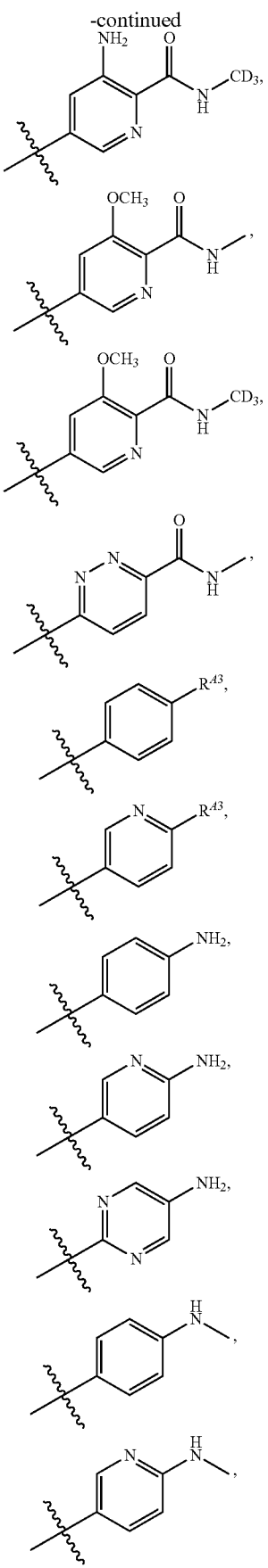

-continued
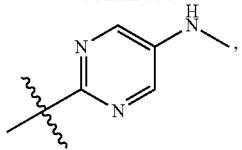
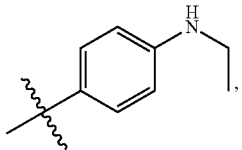
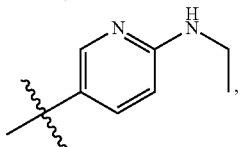
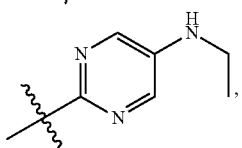
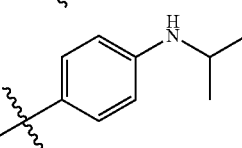
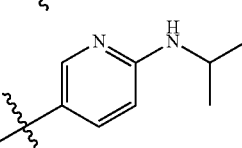
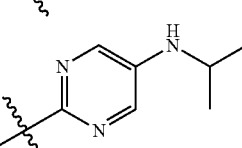
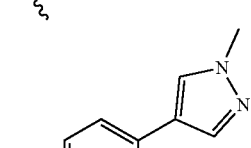
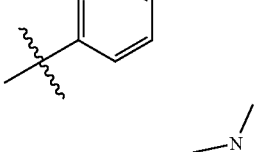
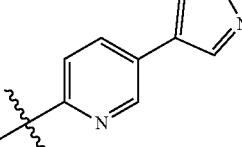
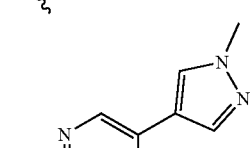
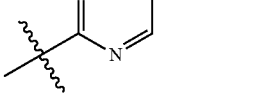
-continued
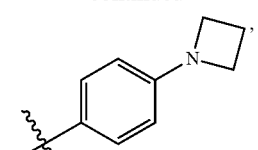
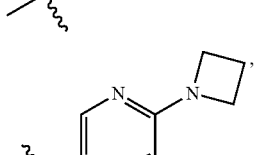
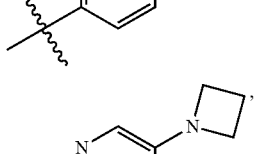
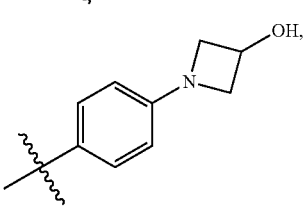
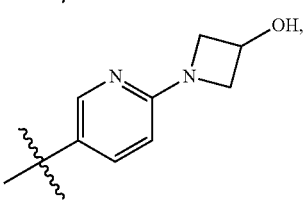
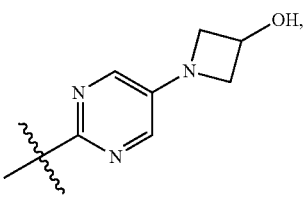
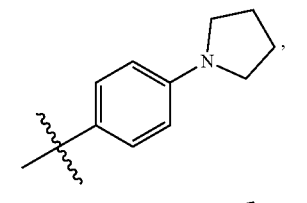
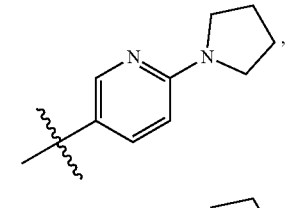
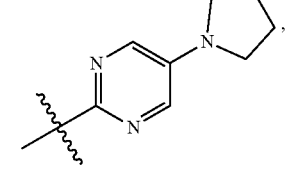

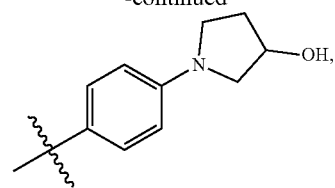
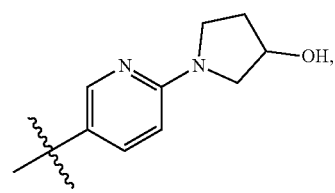
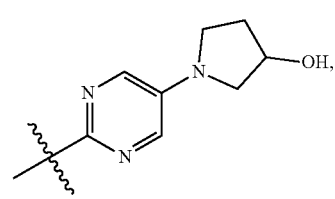
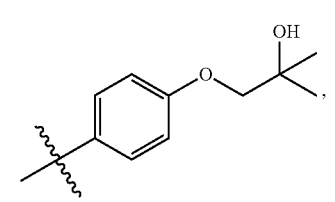
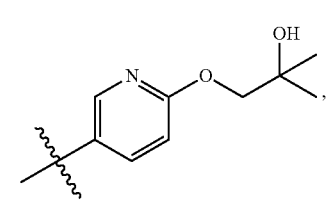
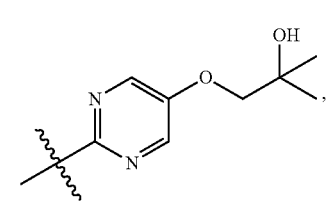
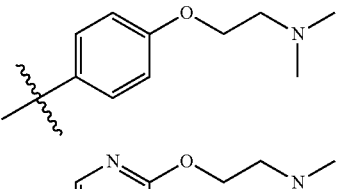
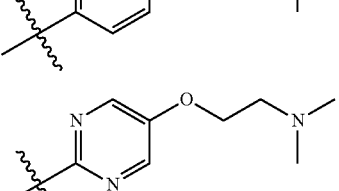
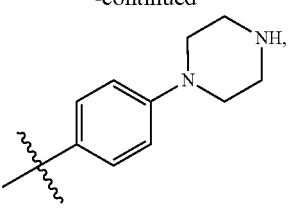
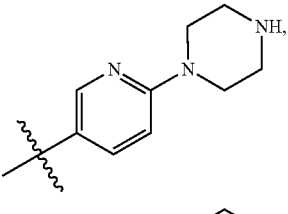
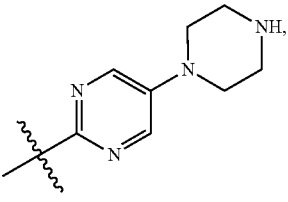
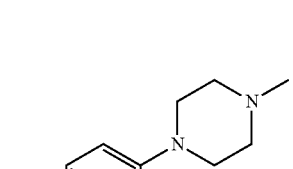
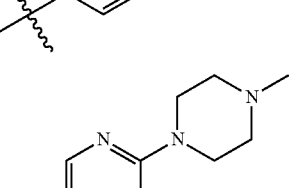
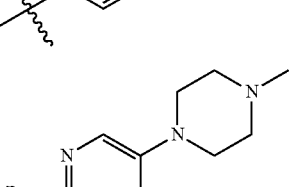
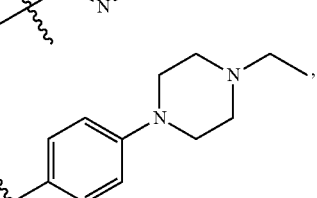
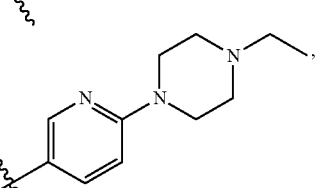

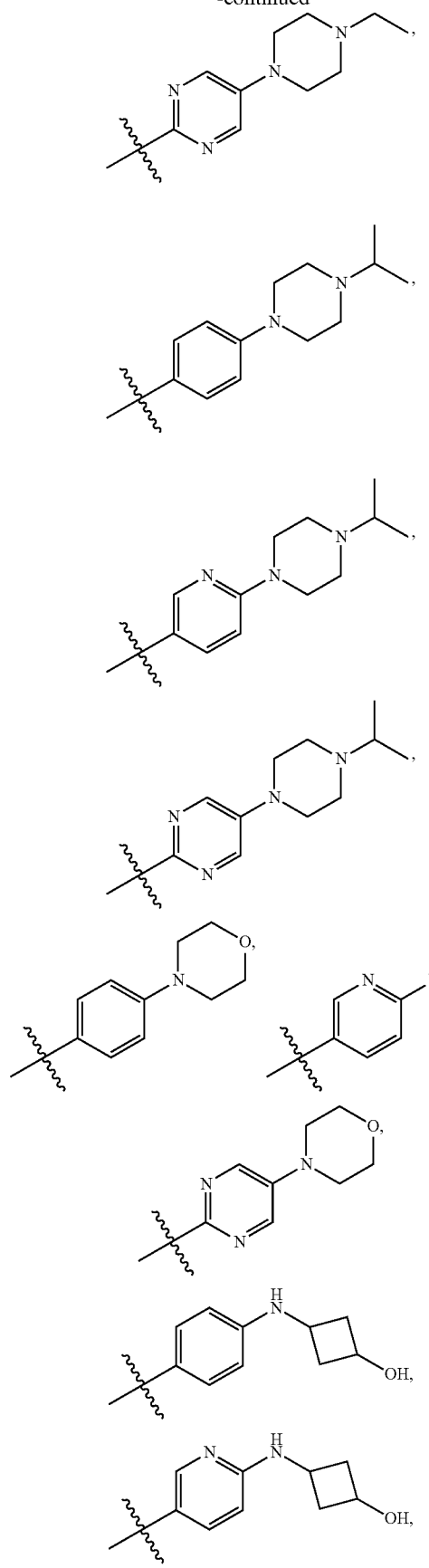
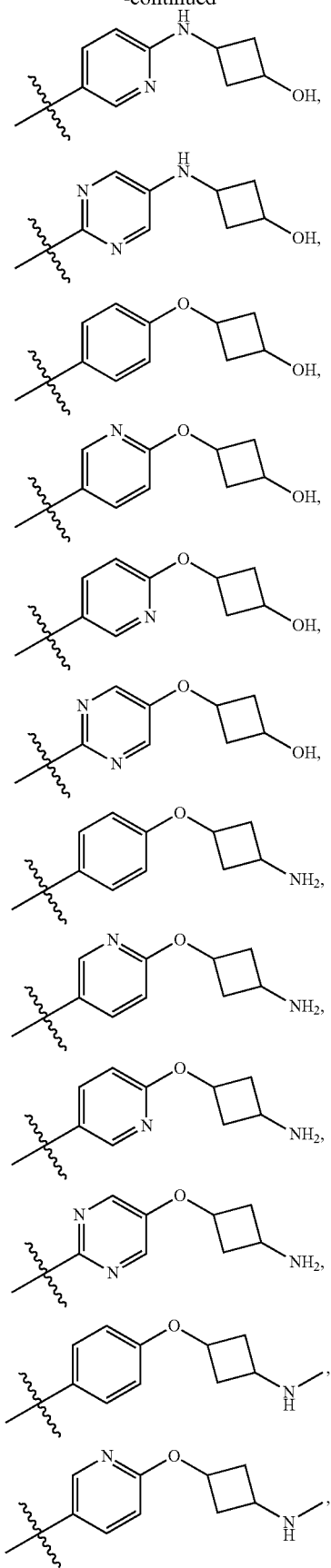

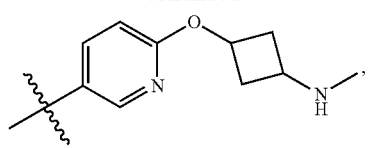
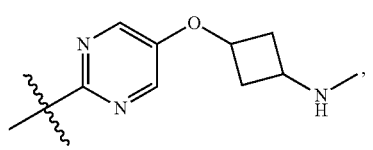
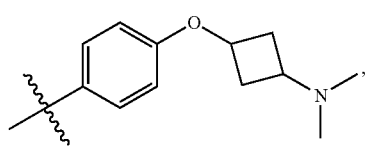
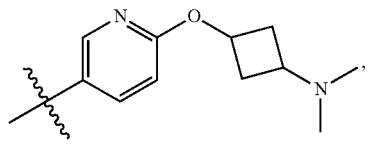
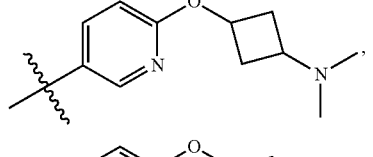
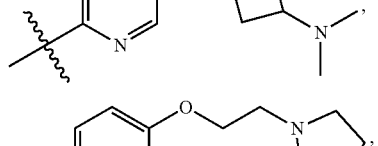
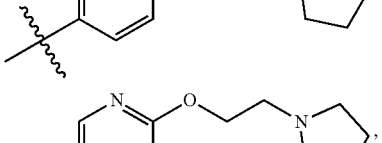
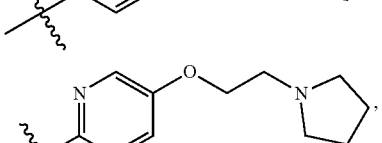
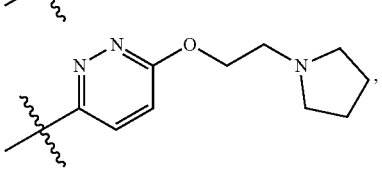
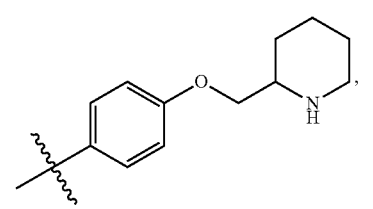
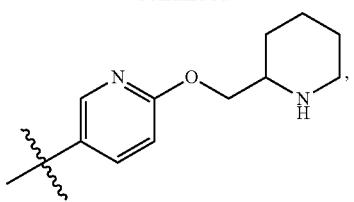
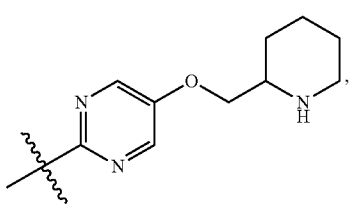
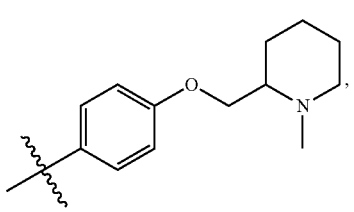
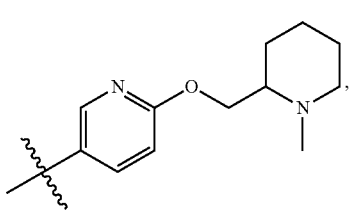
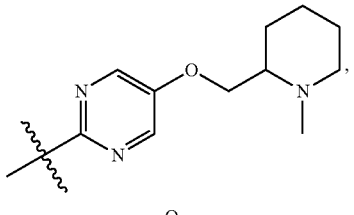
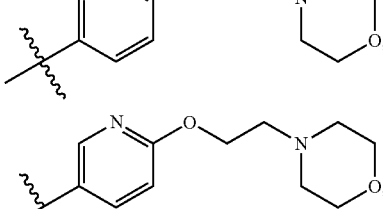
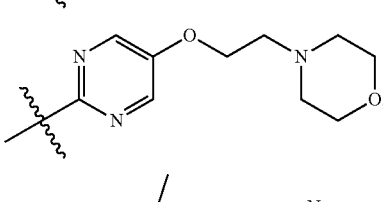
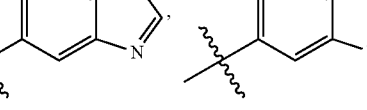

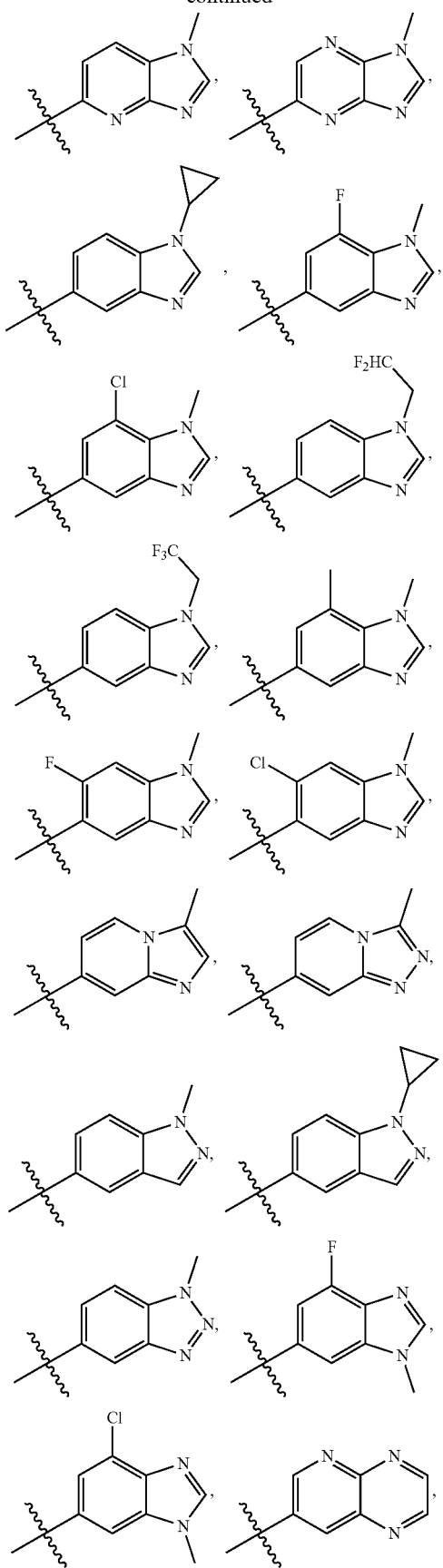
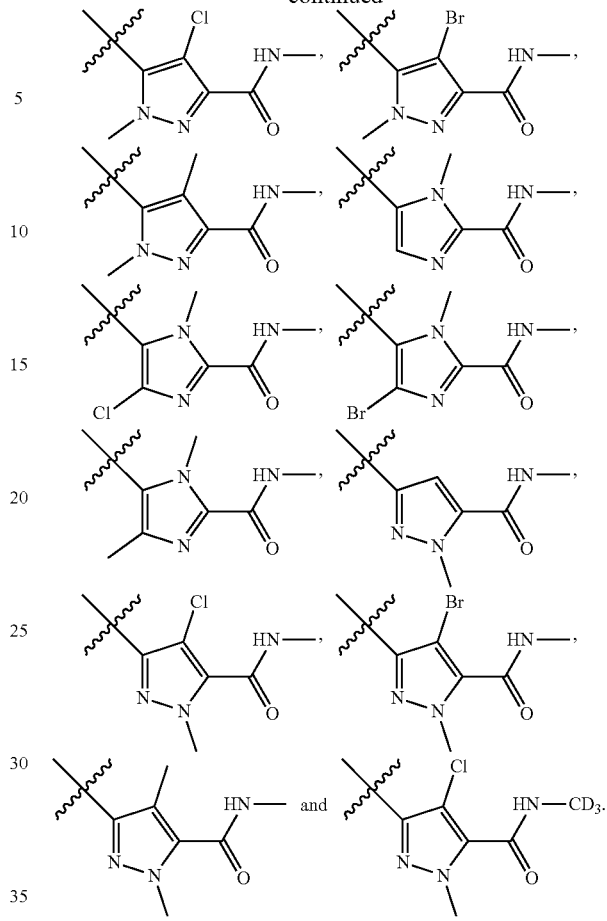
As described herein, $R^3$ can be a substituted
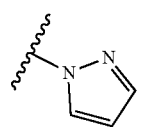 [SMILES: *n1cccn1]
or an unsubstituted or a substituted
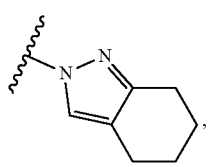
wherein when $R^3$ is a substituted
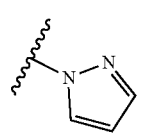
or a substituted the

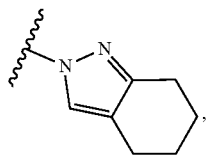 [SMILES: *n1cc2c(n1)CCCC2]

can be substituted 2 or 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$; and the

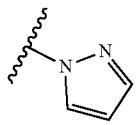 [SMILES: *n1cccn1]

can be substituted 1, 2 or 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$. In some embodiments, R$^3$ can be a substituted

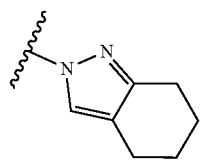 [SMILES: *n1cc2c(n1)CCCC2]

wherein the ring can be substituted 2 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$. In other embodiments, R$^3$ can be a substituted

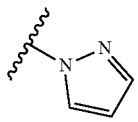 [SMILES: *n1cccn1]

wherein the ring can be substituted 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$. In some embodiments, R$^3$ can be an unsubstituted

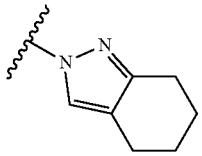

In other embodiments, R$^3$ can be a substituted

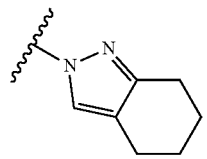

wherein the ring(s) can be substituted 1 time with a substituent independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$. In other embodiments, R$^3$ can be a substituted

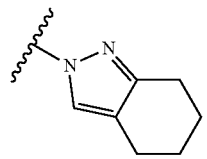 [SMILES: *n1cc2c(n1)CCCC2]

wherein the ring(s) can be substituted 2 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted $C_{1-4}$ alkyl)$_2$. In still other embodiments, R$^3$ can be a substituted

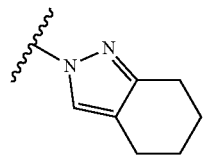 [SMILES: *n1cc2c(n1)CCCC2]

wherein the ring(s) can be substituted 3 times with substituents independently selected from deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH(an unsubstituted $C_{1-4}$ alkyl) and —C(=O)N(an unsubstituted C$_{1-4}$ alkyl)$_2$. When more than one substituent is present, the substituents on

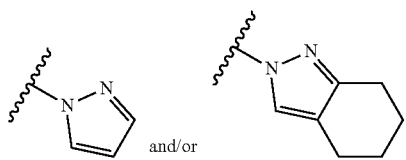 [SMILES: *n1cccn1 ; *n1cc2c(n1)CCCC2] and/or can be the same or different. Exemplary substituents substituted on

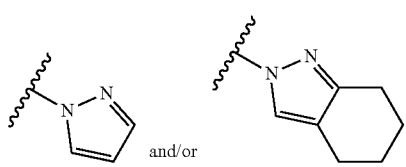 [SMILES: *n1cccn1 ; *n1cc2c(n1)CCCC2] and/or and/or include deuterium, fluoro, chloro, cyano, methyl, ethyl, n-propyl, iso-propyl, n-butyl, iso-butyl, sec-butyl, tert-butyl, n-pentyl, a branched pentyl, methoxy, ethoxy, n-propoxy, iso-propoxy, n-butoxy, iso-butoxy, sec-butoxy, tert-butoxy, n-pentoxy, a branched pentoxy, cyclopropyl, cyclobutyl, —CH(CH$_3$)OCH$_3$, —CHF$_2$, —CH$_2$F, —CF$_3$, —CHClF, —CH$_2$Cl, —CHCl$_2$, —CCl$_3$, —CH$_2$CHF$_2$, —CH$_2$CH$_2$F, —CH$_2$CF$_3$, —CH$_2$CHClF, —CH$_2$CH$_2$Cl, —CH$_2$CHCl$_2$, —CH$_2$CCl$_3$, —CH(CH$_3$)CF$_3$, —CH(CH$_3$)CHF$_2$, —C(CH$_3$)$_2$CF$_3$, —C(CH$_3$)$_2$CHF$_2$, —C(=O)NH$_2$, —C(=O)NH(CH$_3$), —C(=O)NH(CH$_2$CH$_3$), —C(=O)NH(isopropyl), —C(=O)N(CH$_3$)$_2$, —C(=O)N(CH$_2$CH$_3$)$_2$ and —C(=O)N(isopropyl)$_2$. In some embodiments, R$^3$ cannot be

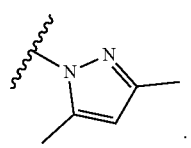

A non-limiting R$^3$ groups include

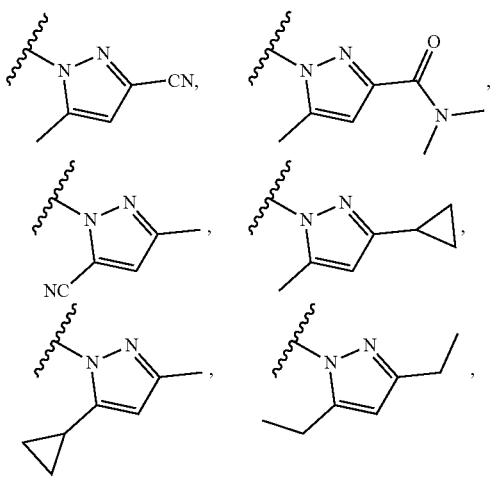

-continued

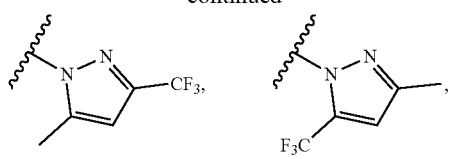

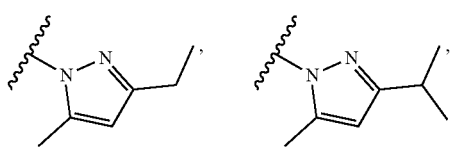

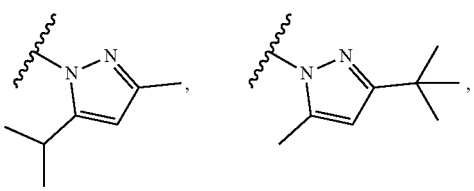

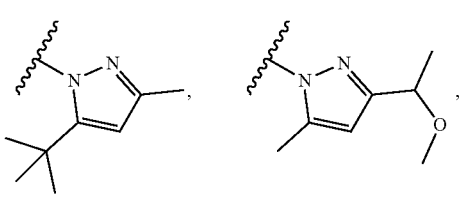

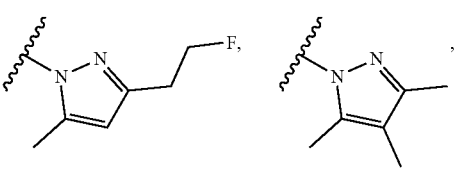

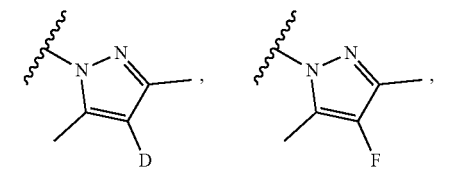

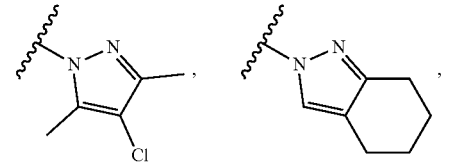

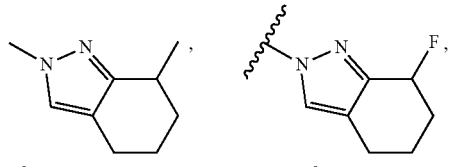

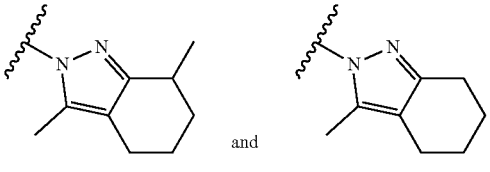

and

In some embodiments, a compound of Formula (I), or a pharmaceutically acceptable salt thereof, can be where R$^1$ can be a substituted phenyl; R$^2$ can be selected from

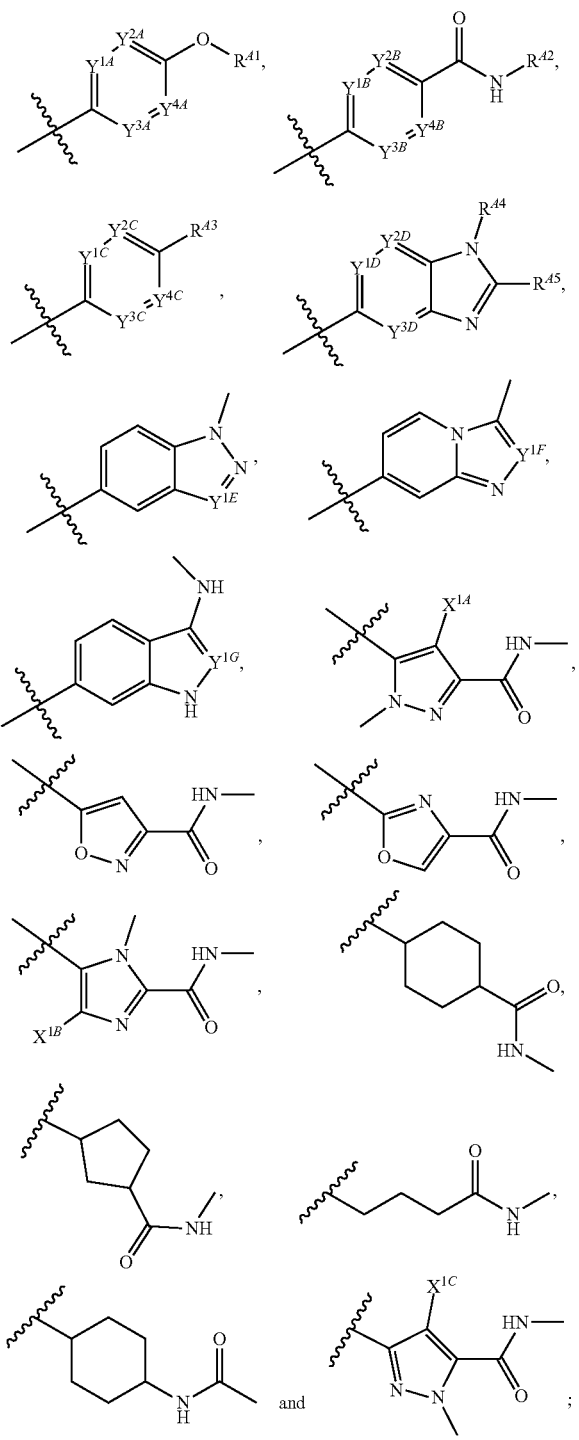

R³ can be selected from a substituted

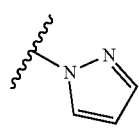

and an unsubstituted or a substituted

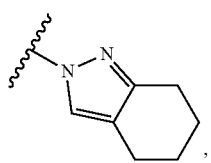 [SMILES: *n1cc2c(n1)CCCC2]

wherein when R³ is a substituted

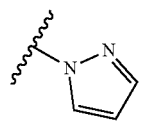

or a substituted

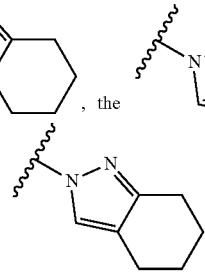, the 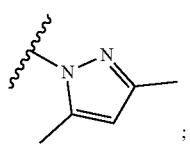 [SMILES: *n1nc(C)cc1C] and the can be substituted 2 or 3 times with substituents independently selected from halogen, cyano, an unsubstituted $C_{1-5}$ alkyl, an unsubstituted $C_{1-5}$ alkoxy, a $C_{1-5}$ alkyl substituted with an unsubstituted $C_{1-5}$ alkoxy, an unsubstituted $C_{3-4}$ cycloalkyl and an unsubstituted $C_{1-5}$ haloalkyl; and provided that R³ is not $X^{1A}$, $X^{1B}$ and $X^{1C}$ can be independently selected from hydrogen, halogen, an unsubstituted $C_{1-5}$ alkyl and an unsubstituted $C_{1-5}$ haloalkyl; $Y^{1A}$ can be CH, C—CHF₂, C—F, C—Cl or N; $Y^{2A}$ can be CH, C-halogen, C—OCH₃ or N; $Y^{3A}$ can be CH or N; $Y^{4A}$ can be CH or N; $Y^{1B}$ can be CH, C—CHF₂, C—F, C—Cl or N (nitrogen); $Y^{2B}$ can be CH, C-halogen, C—OCH₃ or N (nitrogen); $Y^{3B}$ can be CH or N (nitrogen); $Y^{4B}$ can be CH or N (nitrogen); $Y^{1C}$, $Y^{2C}$, $Y^{3C}$ and $Y^{4C}$ can be each independently CH, C-(halogen) or N (nitrogen); $Y^{1D}$ can be CH, C—CH₃, C—OCH₃, C-(halogen), C—CHF₂, C—CF₃ or N (nitrogen); $Y^{2D}$ can be CH, C—CH₃, C—OCH₃, C-(halogen), C—CHF₂, C—CF₃ or N (nitrogen); $Y^{3D}$ can be CH or N (nitrogen); $Y^{1E}$, $Y^{1F}$ and $Y^{1G}$ can be each independently CH, C-(halogen) or N (nitrogen); $R^{A1}$ can be an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy and an unsubstituted $C_{1-5}$ alkoxy; $R^{42}$ can be —$CH_3$ or —$CD_3$; $R^{43}$ can be an unsubstituted or a substituted 5-membered-monocyclic heteroaryl or an unsubstituted or a substituted 5-membered-monocyclic heterocyclyl; $R^{44}$ can be an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl can be substituted with one or more groups selected from hydroxy, —C(=O)OH and —C(=O)$NH_2$; and $R^{45}$ can be selected from hydrogen, halogen, —CN, —OH, —$NH_2$, —C(=O) OH, —CH=$CH_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl can be substituted with one or more hydroxy groups.

Examples of compounds of Formula (I), including pharmaceutically acceptable salts thereof, include:

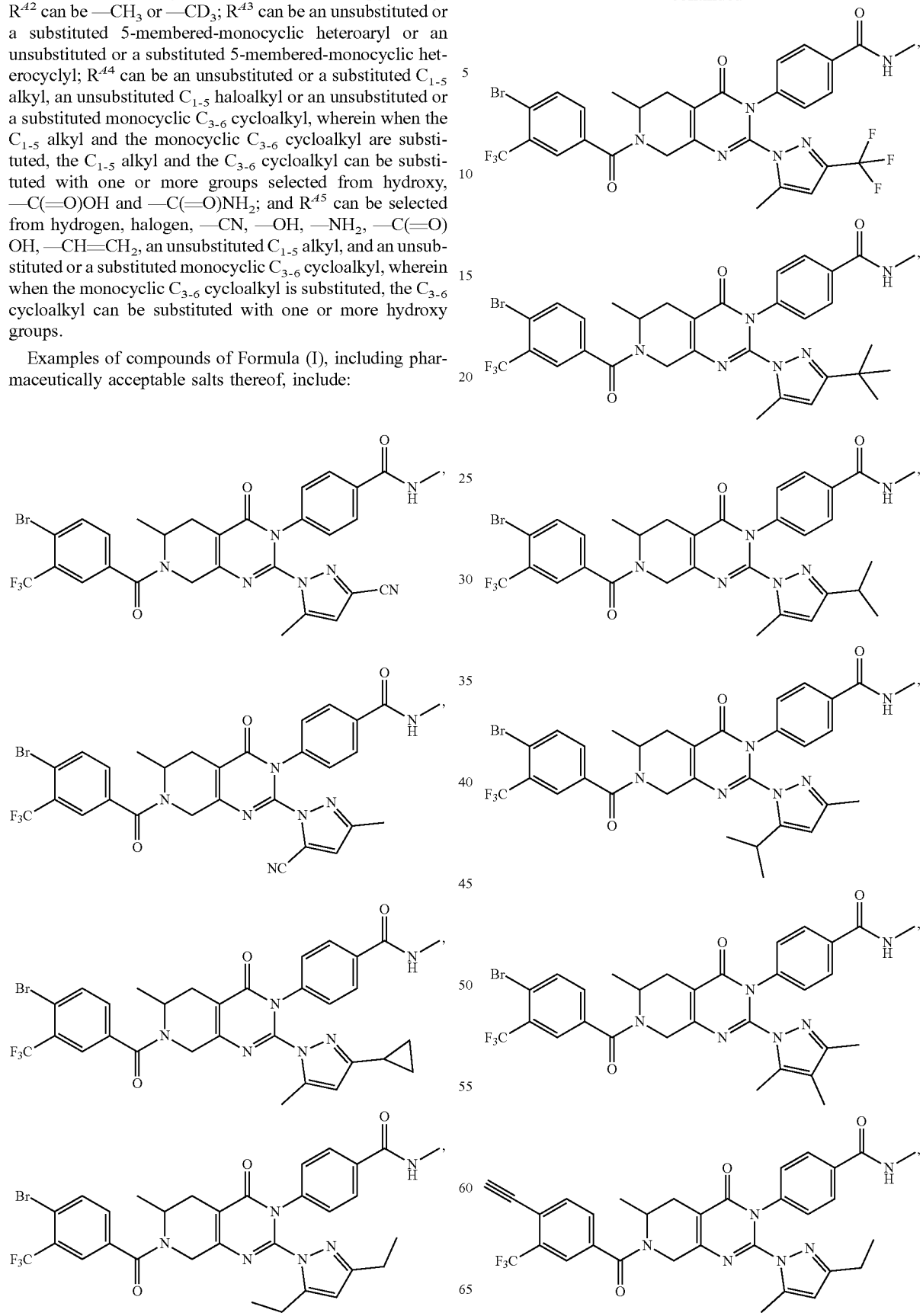

-continued

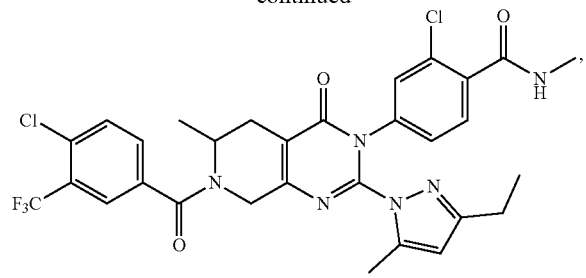
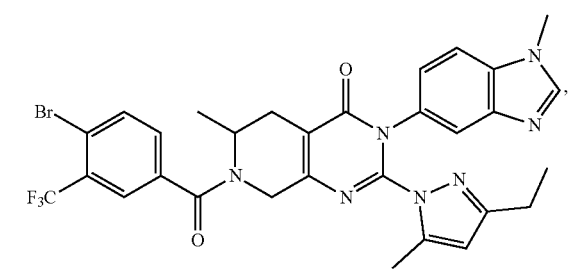
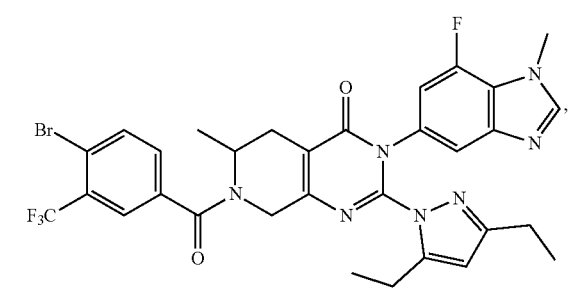
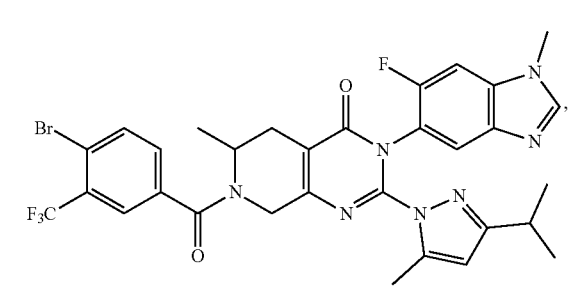
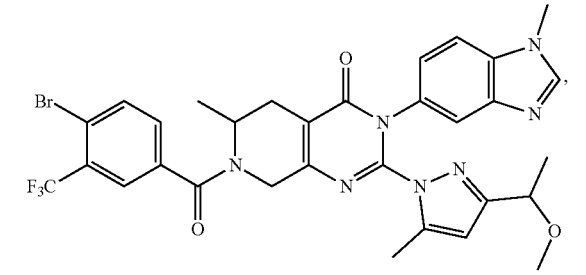
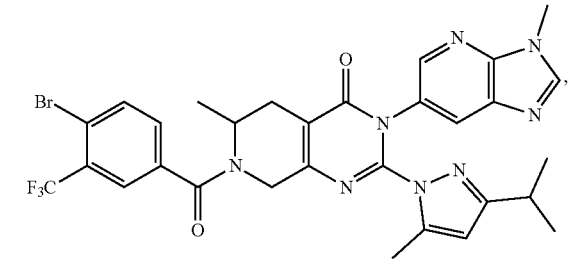
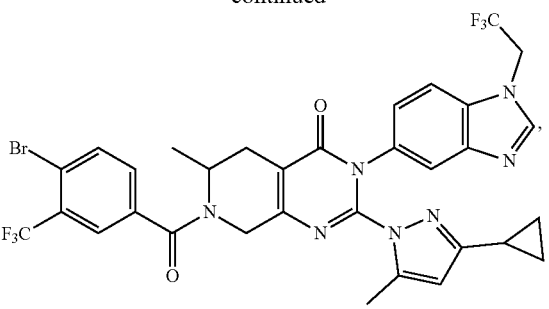
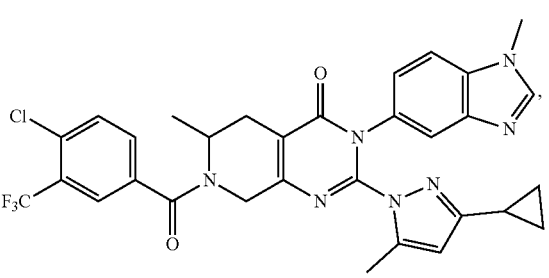
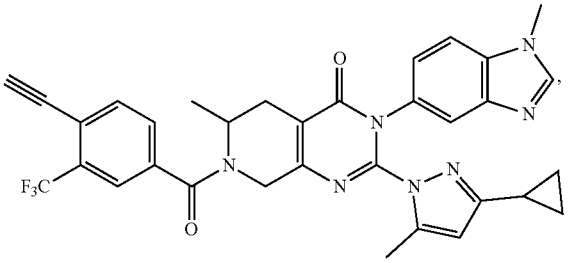
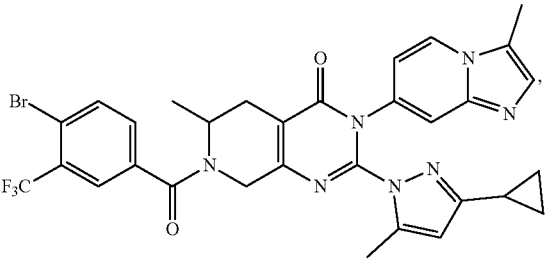
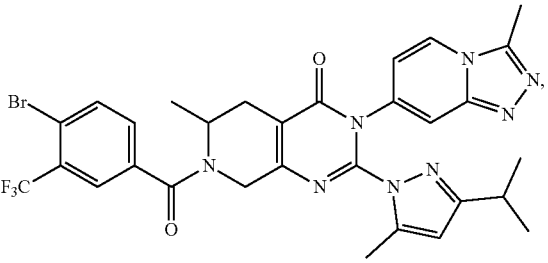
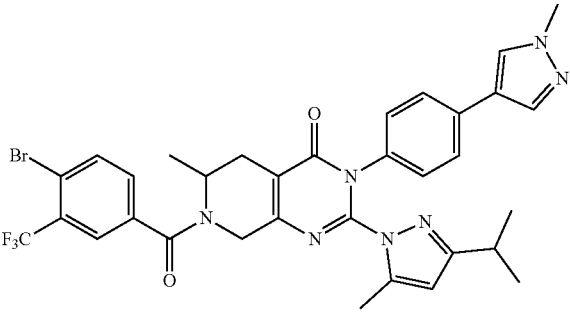

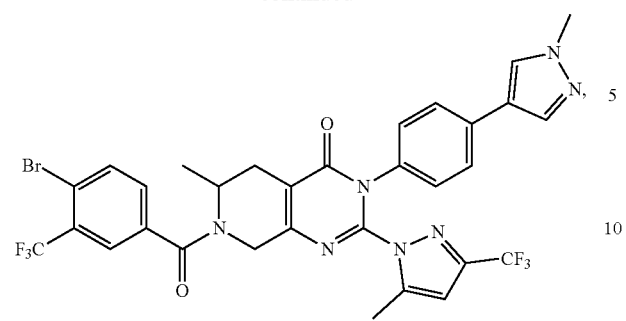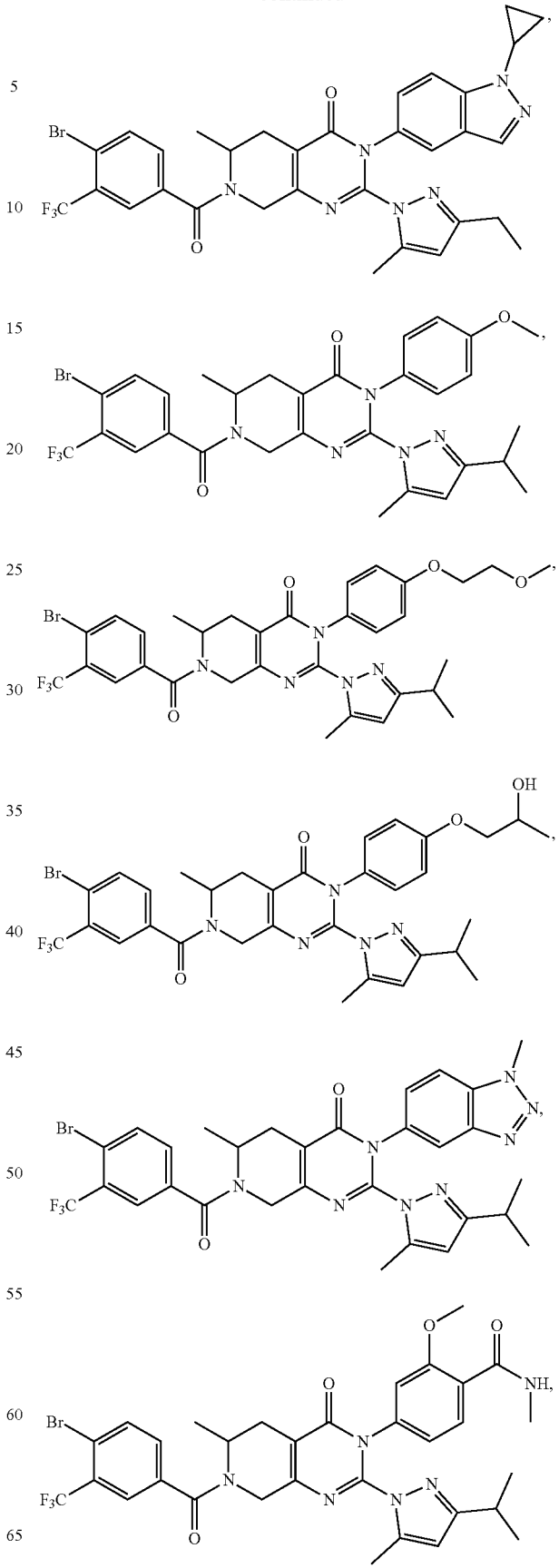

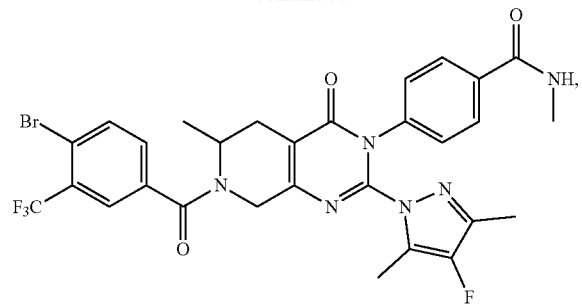
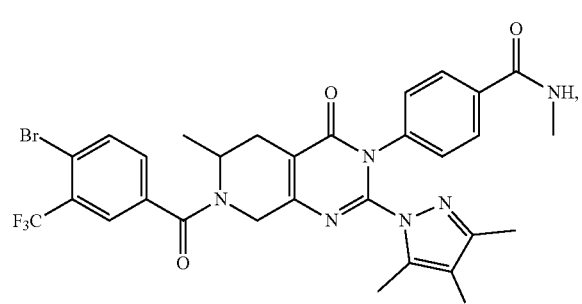
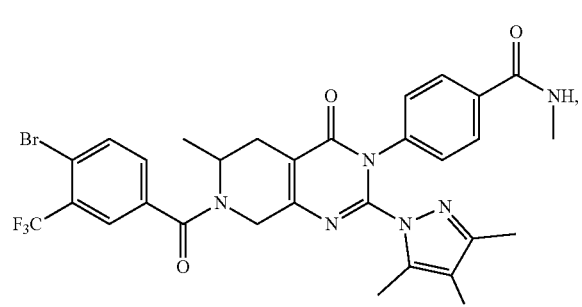
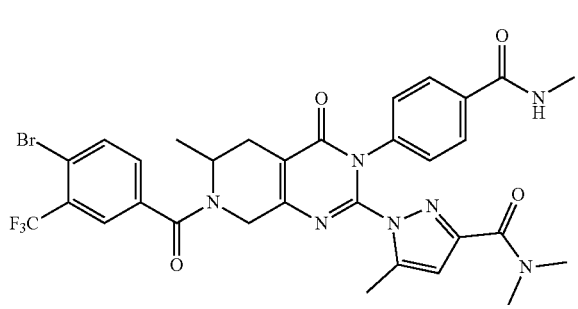
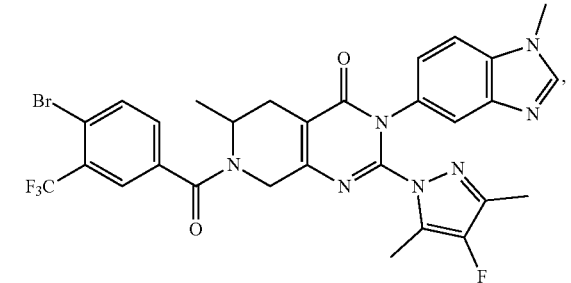
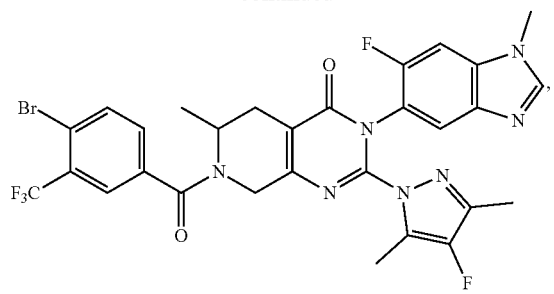
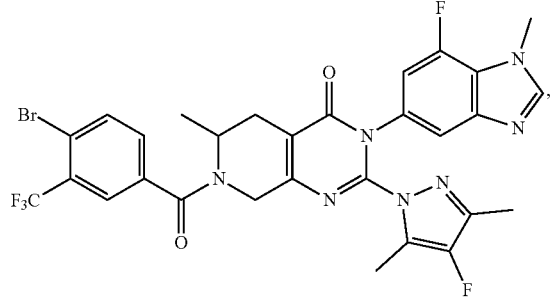
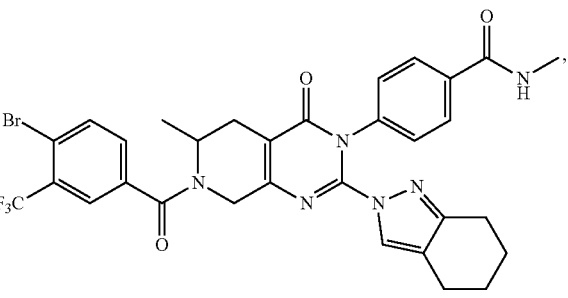
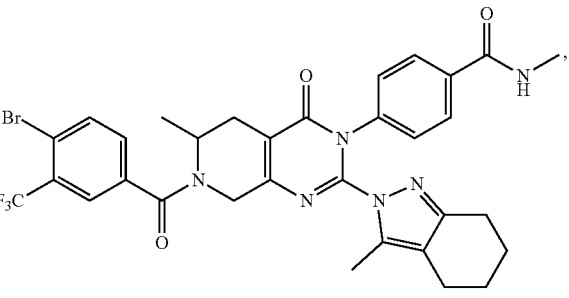
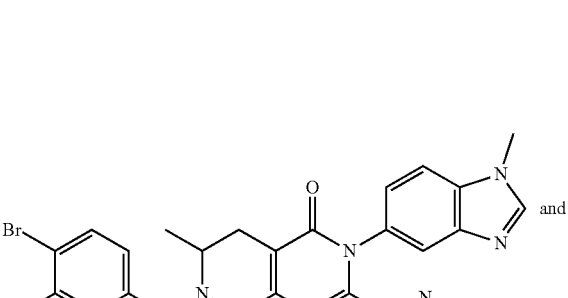

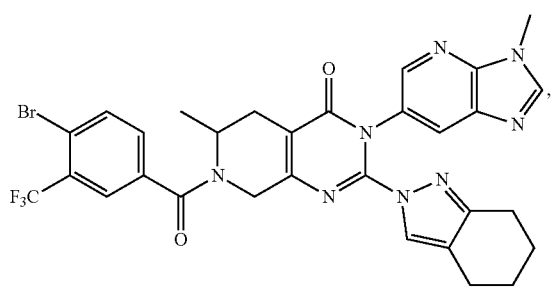
or a pharmaceutically acceptable salt of any of the foregoing.
Additional examples of compounds of Formula (I), including pharmaceutically acceptable salts thereof, include:
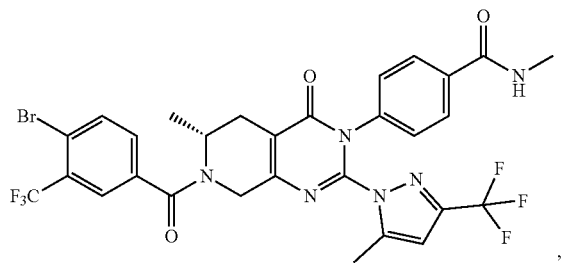
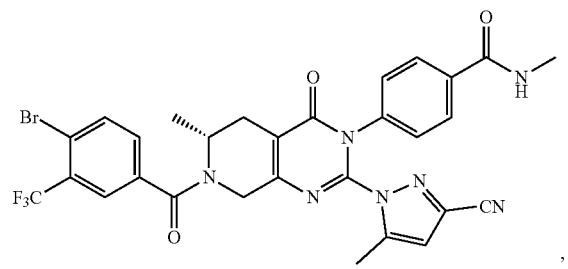
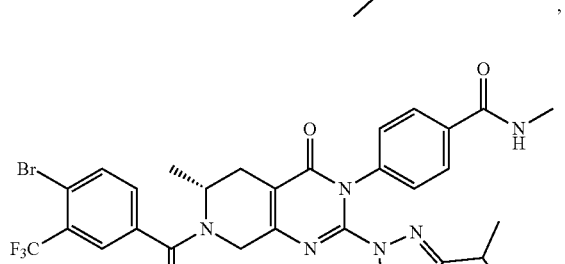
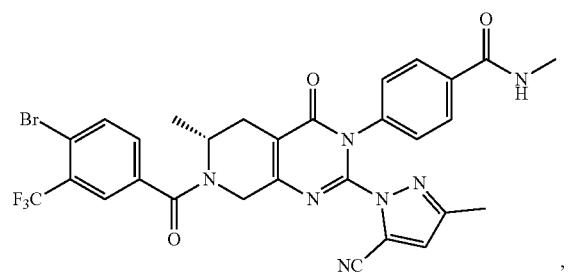
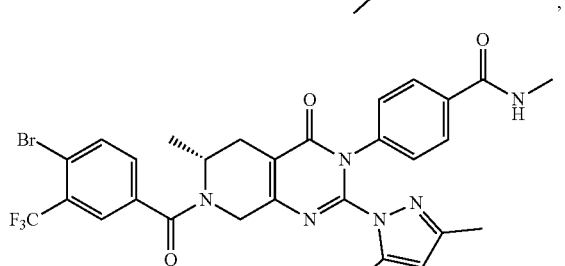
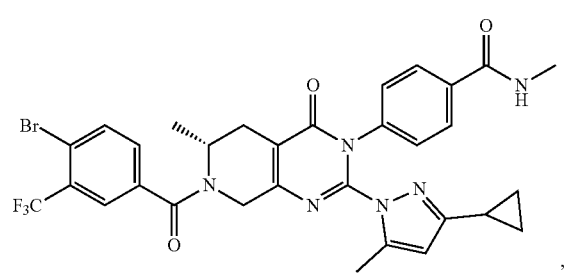
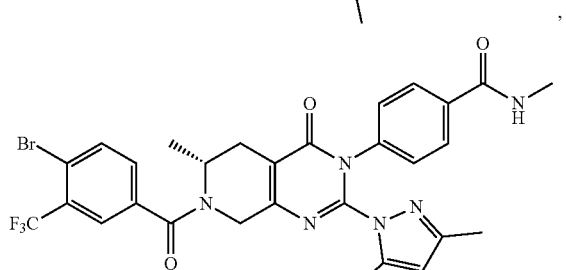
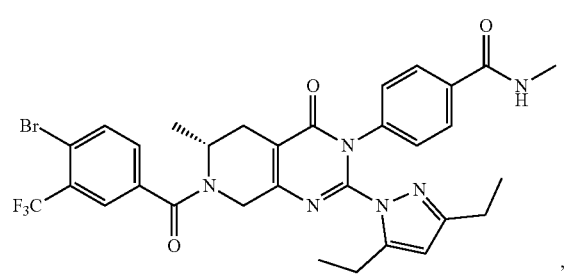
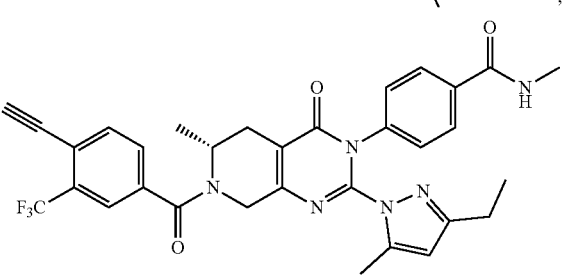

-continued
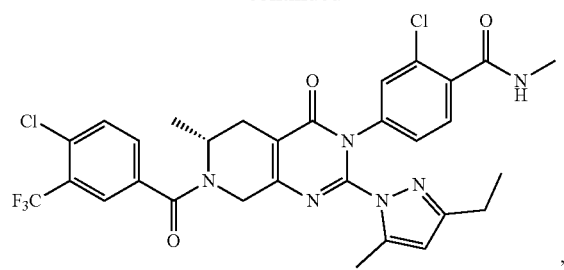
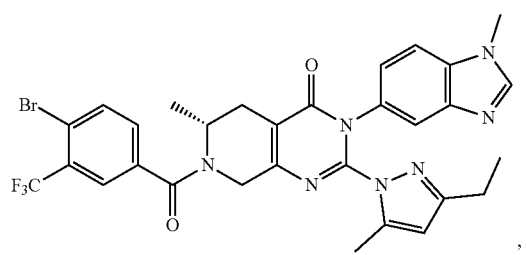
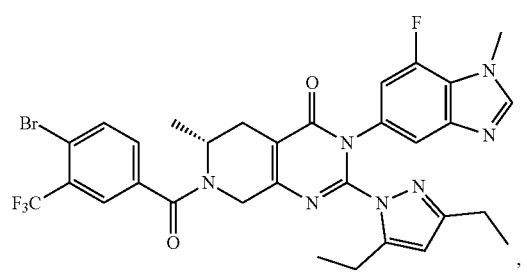
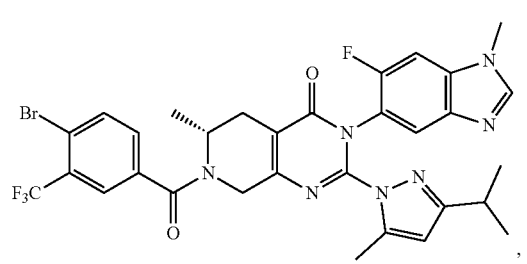
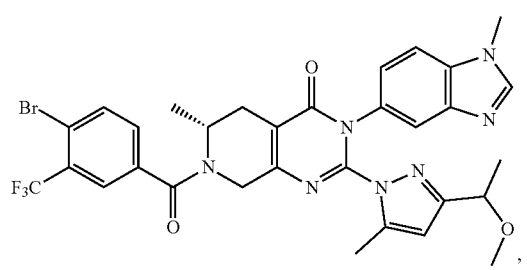
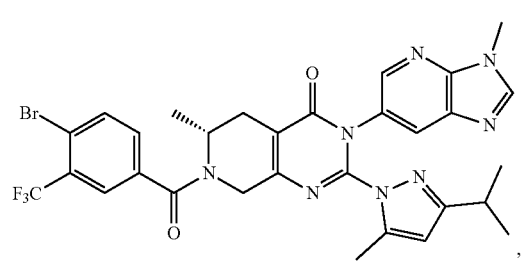
-continued
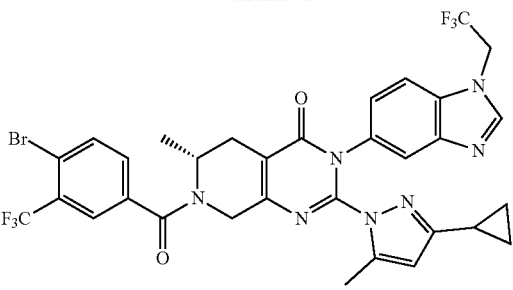
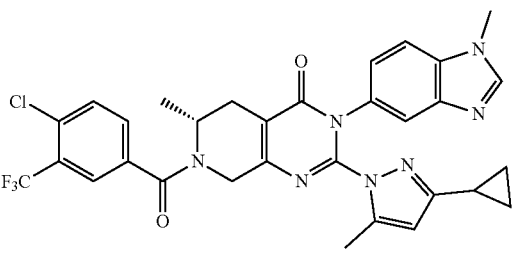
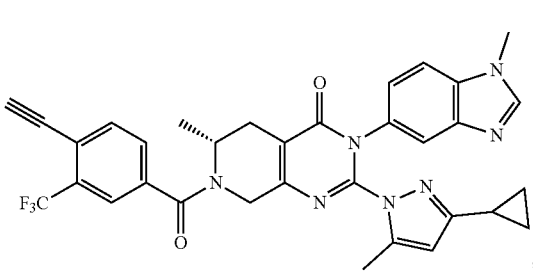
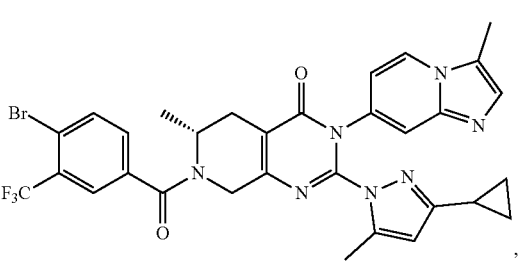
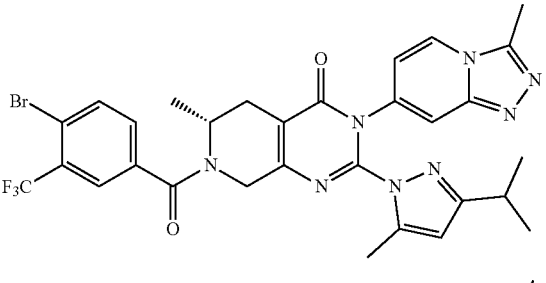
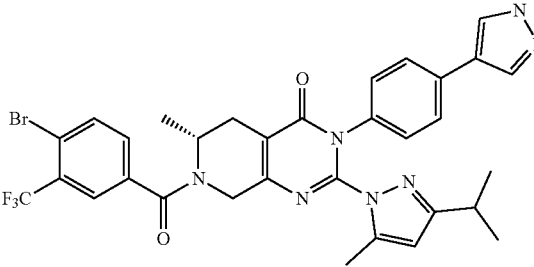

61
-continued
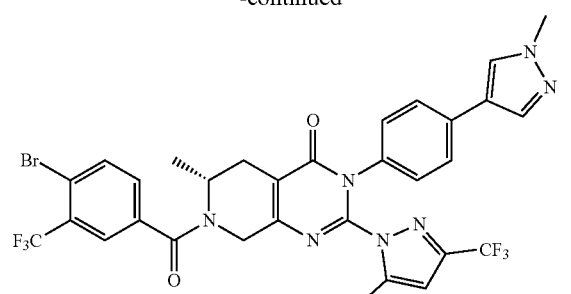
,
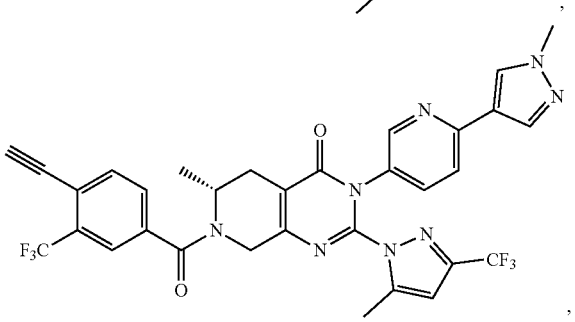
,
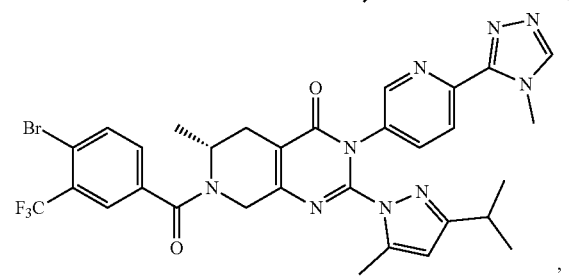
,
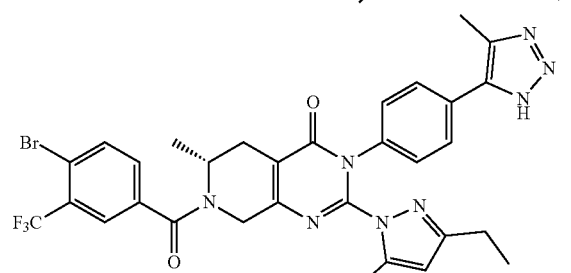
,
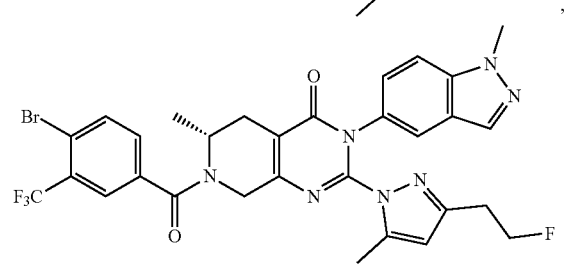
,
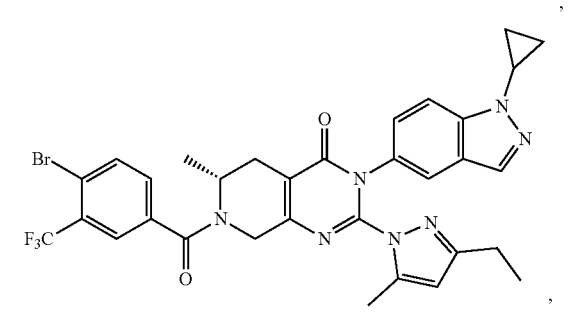
,
62
-continued
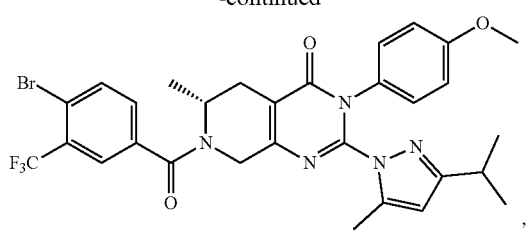
,
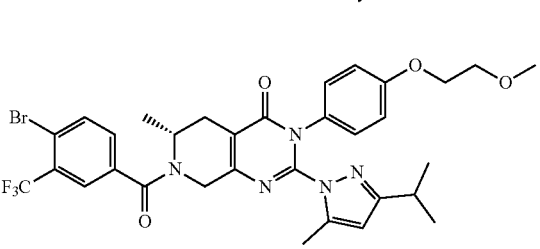
,
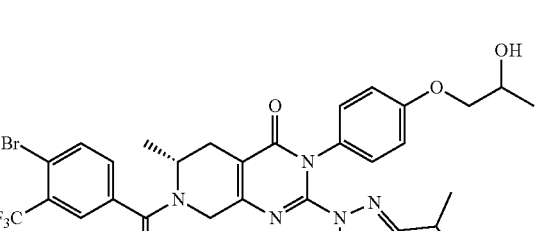
,
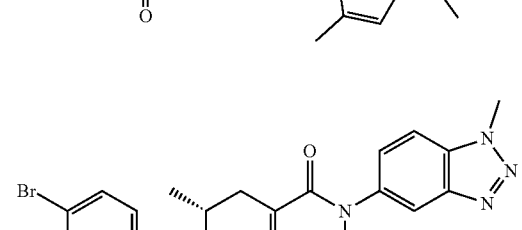
,
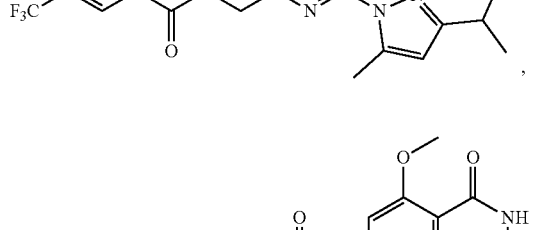
,
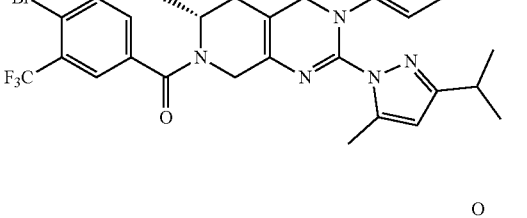
,
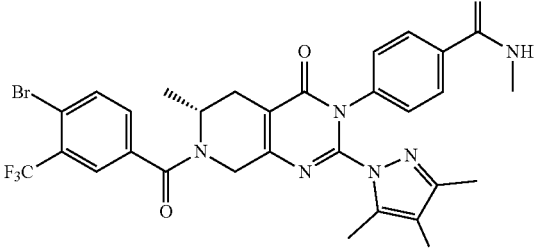
,

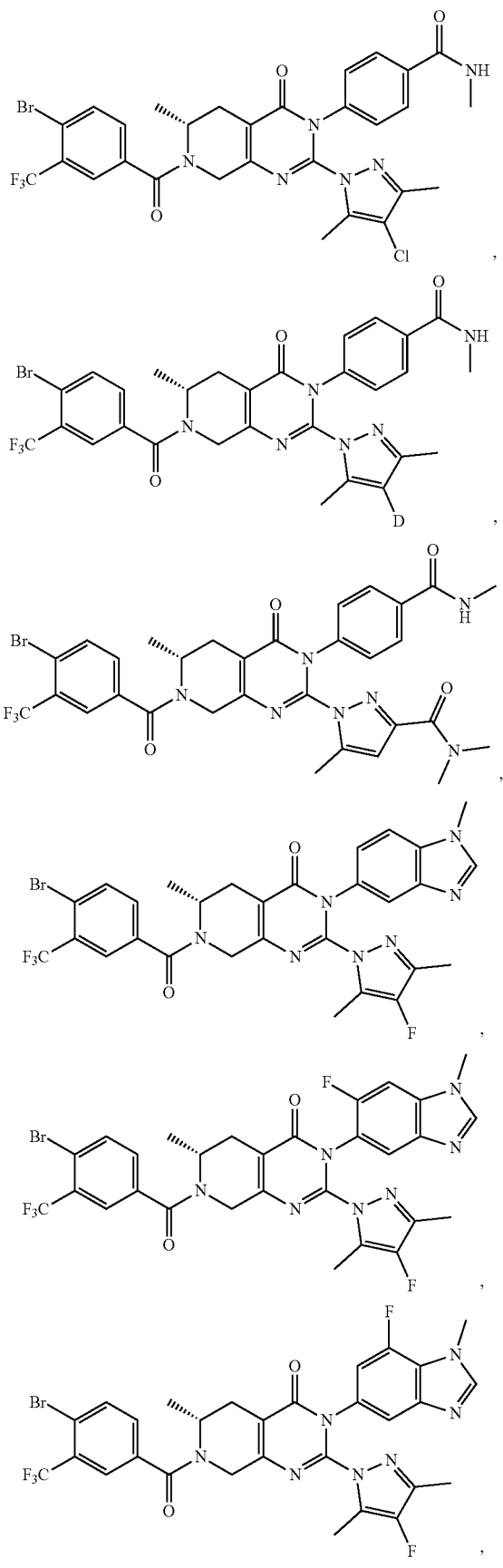

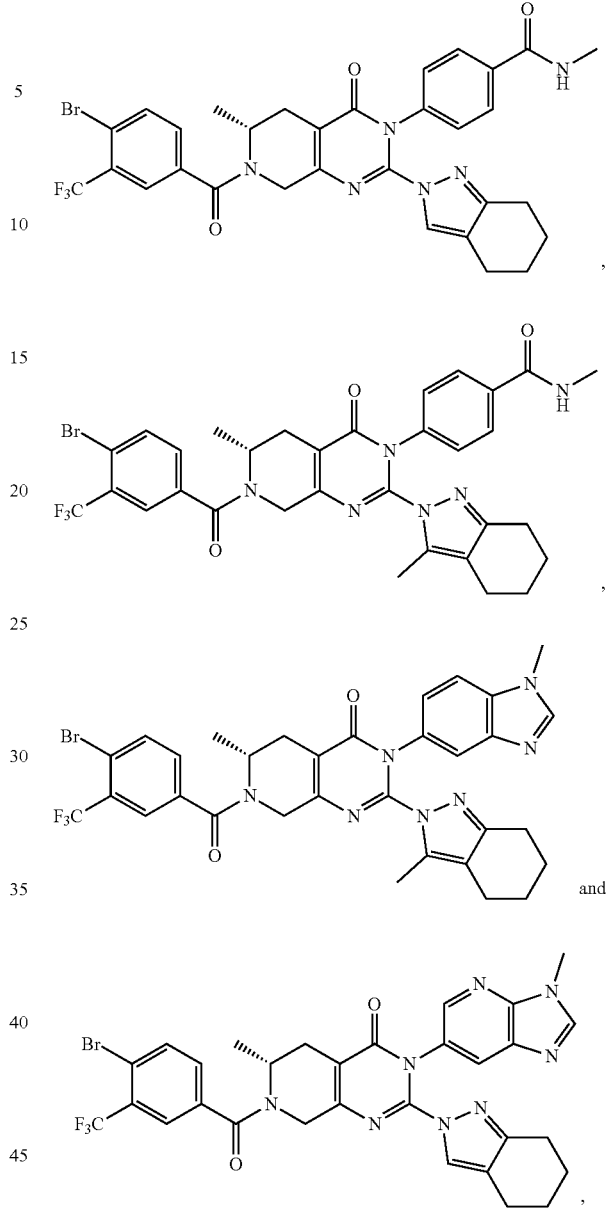

or a pharmaceutically acceptable salt of any of the foregoing.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

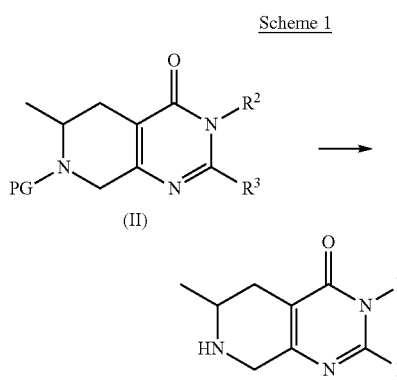

Compounds of Formula (I) (including pharmaceutically acceptable salts thereof) can be prepared from an intermediate of Formula (II), wherein $R^3$ is as provided herein, in which PG represents an amino protecting group such as Boc. The PG group can be cleaved from a compound of Formula (II) using methods known in the art. For example, when PG represents a Boc group, PG can be cleaved using acidic conditions, for example, in the presence of HCl in a suitable solvent (such as 1,4-dioxane) or in the presence of copper triflate. The coupling of the intermediate of Formula (III) with a suitable agent can afford a compound of Formula (I), along with pharmaceutically acceptable salts thereof. As an example, compounds of Formula (I), along with pharmaceutically acceptable salts thereof, can be obtained by reacting a compound of Formula (III) with an acyl chloride of general formula $R^1$—C(=O)—Cl, in the presence of a suitable base (e.g., triethylamine) in a suitable solvent (e.g., acetonitrile). As an alternative example, compounds of Formula (I) and its pharmaceutically acceptable salts, can be obtained by reacting a compound of Formula (III) with a carboxylic acid of general formula $R^1$—COOH, in the presence of a suitable base (e.g., triethylamine), in a suitable solvent (e.g., acetonitrile or DMF), using a suitable amino acid coupling agent (e.g., HATU, or EDC). Further compounds of Formula (I), along with pharmaceutically acceptable salts thereof, can be prepared from a compound of Formula (III) using methods known in the art.

Scheme 2

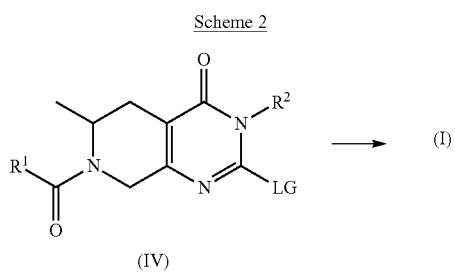

Compounds of Formula (I), including pharmaceutically acceptable salts thereof, can also be prepared from an intermediate of Formula (IV), in which LG represents a leaving group (such as sulfhydryl, methylsulfoxide or halogen (e.g., Cl or Br)). A compound of Formula (I) can be prepared from a compound of Formula (IV) in which LG represents —$SO_2CH_3$ by reacting $R^3$ as provided herein, in the presence of a base (such as diisopropylethylamine (DIPEA) or NaH) in a suitable solvent (such as THF, DMF or acetonitrile). A compound of Formula (I) can be prepared from a compound of Formula (IV) in which LG represents chloro by reacting an optionally substituted pyrazole, in the presence of a base (for example, triethylamine, DBU or DIPEA) in a suitable solvent (such as acetonitrile, DMF or THF), optionally in the presence of a catalyst, such as DMAP.

Scheme 3

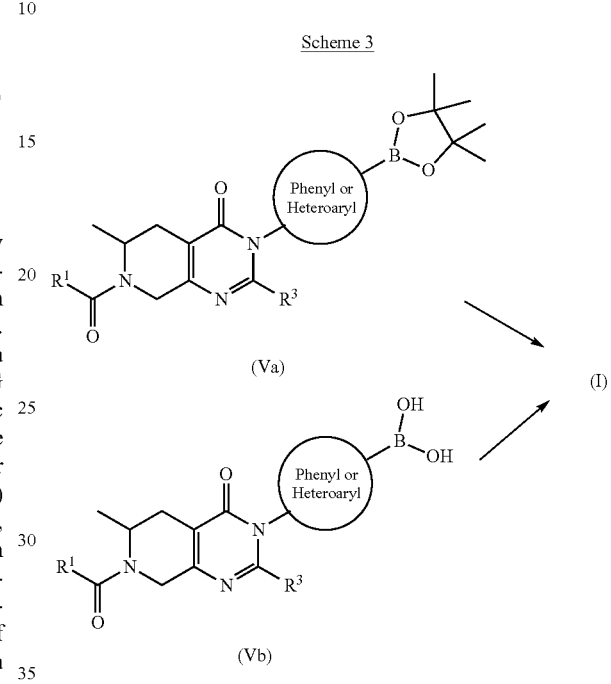

A compound of Formula (I), along with pharmaceutically acceptable salts thereof, in which $R^2$ represents a phenyl or a heteroaryl, can be prepared from compounds of Formula (Va) and Formula (Vb), both of which have $R^3$ as provided herein. Formula (Va) and Formula (Vb) are in turn generated by reacting the corresponding heteroarylhalide (such as bromo or iodo) with a palladium catalyst (e.g. $Pd(PPh_3)_4$) in the presence of a base (for example, $Cs_2CO_3$) and pinacoldiborane in a suitable solvent or solvent mixture (e.g. 1,4-dioxane/$H_2O$). Alternatively, other methods known to those skilled in the art maybe used to generate boronic acids or boronic esters (for example, Leermann et al., Org. Lett. (2011) 13, 4479-4481; Zhang et al., J. Am. Chem. Soc. (2019) 141, 9124-9128; Mfuh et al., J. Am. Chem. Soc. (2016) 138, 2985-2988).

Scheme 4

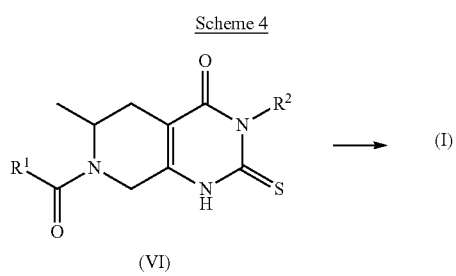

Compounds of Formula (I), along with pharmaceutically acceptable salts thereof, can be prepared from an intermediate of Formula (VI) and R³ as provided herein, in the presence of t-butyl hydroperoxide (TBHP) in a suitable solvent (e.g., acetonitrile).

Scheme 5

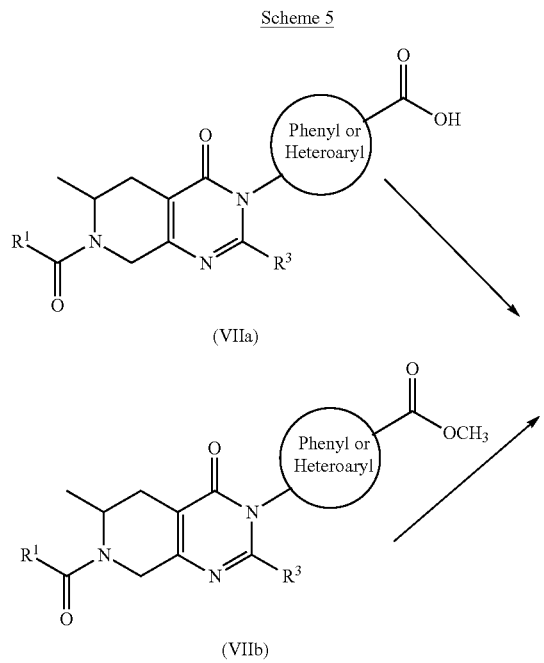

(VIIa)

(VIIb)

Compounds of Formula (I), including pharmaceutically acceptable salts thereof, in which R² represents a phenyl or heteroaryl substituted with an amide can be prepared from an acid intermediate of Formula (VIIa) that incorporates R³ as provided herein, and an amine of Formula NH₂—R^A2, using a peptide coupling agent (such as HATU) in the presence of a base (for example, diisopropylethylamine) in a suitable solvent, such as acetonitrile or DMF. Compounds of Formula (I), along with pharmaceutically acceptable salts thereof, in which R² represents a phenyl substituted with an amide or R² represents a heteroaryl substituted with an amide can be prepared from an ester intermediate of Formula (VIIb) that incorporates R³ as provided herein, and an amine of general formula NH₂—R^A2 in a suitable solvent (such as acetonitrile), optionally at elevated temperature.

Scheme 6

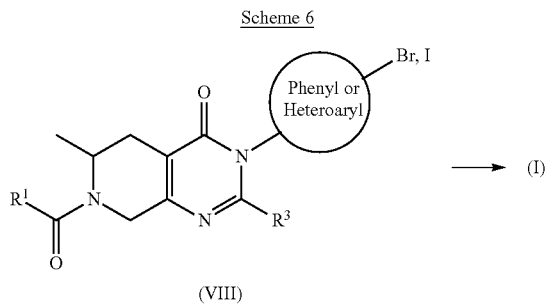

(VIII)

Compounds of Formula (I), or a pharmaceutically acceptable salt thereof, in which R² represents a phenyl or a heteroaryl substituted with an amine, can be prepared via Buchwald-Hartwig amination from an intermediate of Formula (VIII) that has R³ as provided herein, and an amine, using a catalyst (for example, XantPhos Pd G3) in the presence of a base (e.g., Cs₂CO₃) in a suitable solvent (such as 1,4-dioxane). Compounds of Formula (I), or a pharmaceutically acceptable salt thereof, in which R² represents a phenyl or a heteroaryl substituted with a monocyclic heteroaryl, can be prepared from an intermediate of Formula (VIII) and a boronic acid or boronic ester (for example, an optionally substituted 4,4,5,5-tetramethyl-1,3,2-dioxaborolan-2-yl heteroaryl) using a catalyst, such as Pd(PPh₃)₄, in the presence of a base (such as Cs₂CO₃) in a suitable solvents, such as 1,4-dioxane/H₂O. Examples in literature of this reaction are described and the following references are examples: Fan, et al., Org. Lett. (2015) 17, 5934-5937; Sheng et al. Org. Lett. (2008) 10, 4109-4112.

Scheme 7

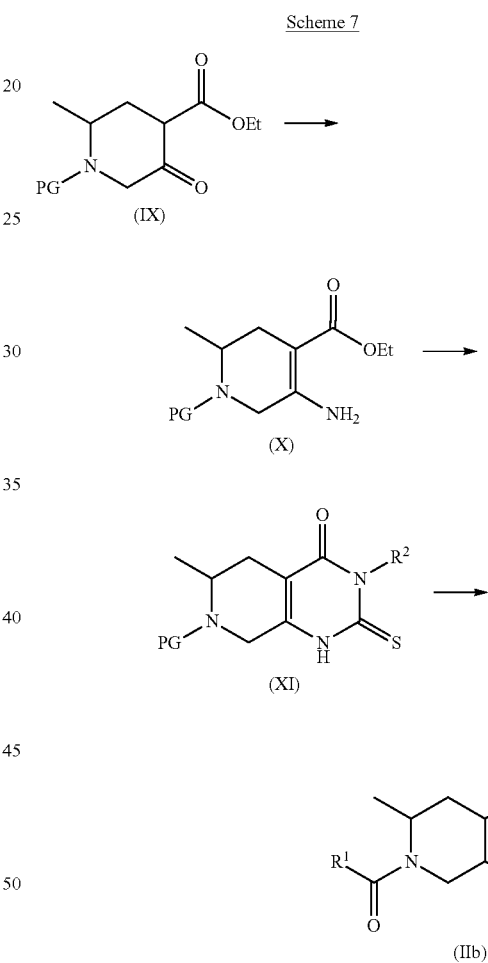

Intermediate of Formula (IIb) can be prepared from a compound of Formula (IX) using ammonium acetate in a suitable solvent (such as ethanol) to afford an intermediate of Formula (X). Treatment of the intermediate of Formula (X) with a base, such as NaH, in a suitable solvent (such as THF) followed by the subsequent addition of an isothiocyanate of general formula R²—NCS can give an intermediate of Formula (XI). The intermediate of Formula (XI) can be subsequently alkylated with an iodomethane, or any alkylhalide, in the presence of a base (such as DBU) in a suitable solvent (such as DMF) to afford a compound of Formula (IIb).

Scheme 8

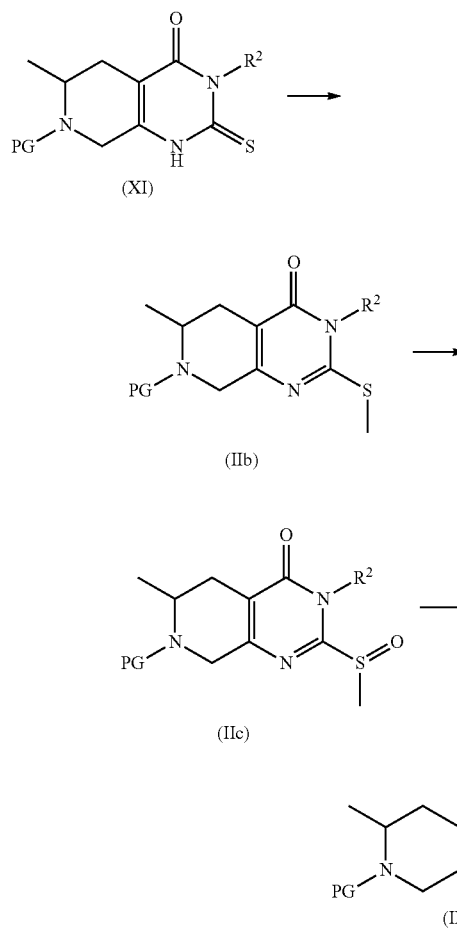

Intermediate of Formula (III) that has a R³ as provided herein, can be prepared from a compound of Formula (XI) using methyl iodide or methyl bromide, in the presence of a base, such as DBU, in a suitable solvent, such as DMF, to afford an intermediate of Formula (IIb). Oxidation of an intermediate of Formula (IIb) to a sulfoxide intermediate of Formula (IIc) can be achieved by a treatment with an oxidative agent (such as m-CPBA) in the presence of MgSO₄ and NaOAc in a suitable solvent (such as dichloromethane). Treatment of intermediate of Formula (IIc) with 3,5-dimethylpyrazole in the presence of a base (such as DIPEA), optionally in the presence of a catalyst (for example, DMAP) in a suitable solvent (such as DMF) can afford an intermediate of Formula (III).

Scheme 9

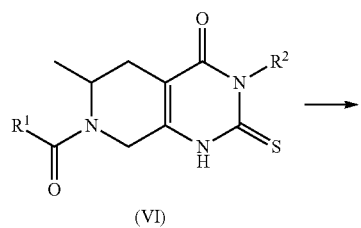

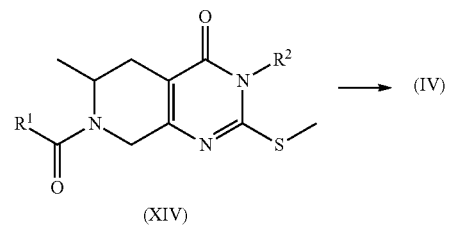

Intermediates of Formula (IV) in which the leaving group LG represents a methylsulfoxide can be prepared from an intermediate of Formula (VI) using methyl iodide or methyl bromide, in the presence of a base (for example, DBU) in a suitable solvent, such as DMF, to afford an intermediate of Formula (XIV). Oxidation of an intermediate of Formula (XIV) to a sulfoxide intermediate of Formula (IV, LG is sulfoxide) can be achieved using an oxidative agent, such as m-CPBA, in the presence of MgSO₄ and NaOAc in a suitable solvent, such as dichloromethane.

Scheme 10

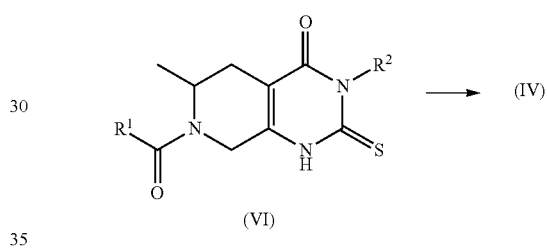

Intermediates of Formula (IV) in which the leaving group LG is chloro, can be prepared from an intermediate of Formula (VI) using thiophosgene, or sulfuryl chloride in a suitable solvent (such as THF).

Scheme 11

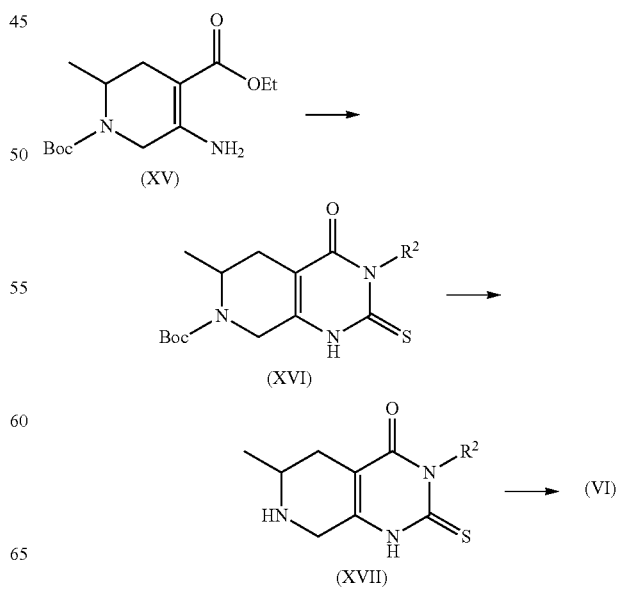

-continued

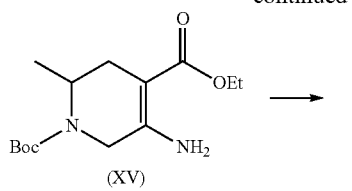

(XV)

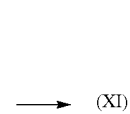

(XXIV)

Intermediate of Formula (VI) can be prepared from an intermediate of Formula (XV) in the presence of a base, such as NaH, in a suitable solvent (for example, THF) followed by the subsequent addition of an isothiocyanate of general formula R²—NCS to afford an intermediate of Formula (XVI). The Boc group of an intermediate of Formula (XVI) can be deprotected in the presence of an acid (e.g., HCl or TFA) in a suitable solvent (for example, 1,4-dioxane) to afford an intermediate of Formula (XVII). Intermediates of Formula (VI) can be prepared from an intermediate of Formula (XVII) following several conditions known to those skilled in the art.

Further compounds of Formula (VI) can be obtained by reacting a compound of Formula (XVII) with an acyl chloride of general formula R¹—C(=O)—Cl in the presence of a base (e.g., Et₃N) in a suitable solvent (e.g., DMF), including bases and solvents known to those skilled in the art. Compounds of Formula (VI) can be obtained by reacting compound of Formula (XVII) with a carboxylic acid of general formula R¹—C(=O)—OH in the presence of an amide coupling agent (such as HATU) in a suitable solvent. Additional compounds of Formula (VI) can be prepared from a compound of Formula (XVII) using methods known in the art.

Scheme 12

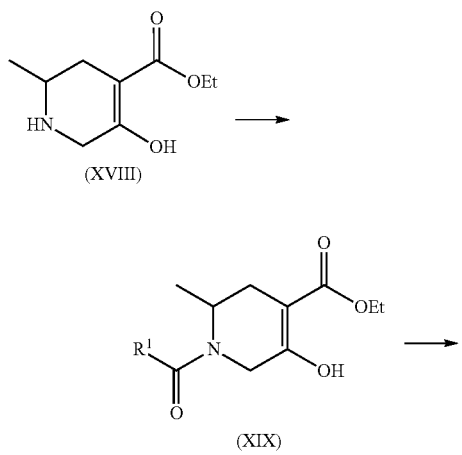

-continued

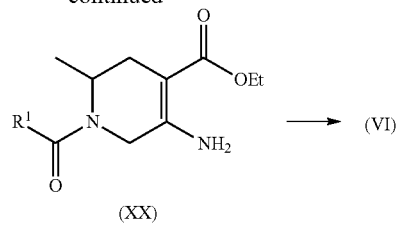

(XX)

An intermediate of Formula (VI) can be prepared from an intermediate of Formula (XVIII) following conditions known in the art, such as conditions used to convert an intermediate of Formula (XVII) to an intermediate for Formula (VI). For example, intermediates of Formula (XIX) can be obtained by reacting a compound of Formula (XVIII) with an acyl chloride of general formula R¹—C(=O)—Cl in the presence of a base in a suitable solvent. Additional compounds of Formula (XIX) can be obtained by reacting a compound of Formula (XVIII) with a carboxylic acid of general formula R¹—C(=O)—OH in the presence of an amide coupling agent (such as HATU) in a suitable solvent. Suitable solvents are known to those skilled in the art and/or described herein.

Intermediates of Formula (XX) can be prepared from an intermediate of Formula (XI) in the presence of ammonium acetate, in a suitable solvent (such as ethanol). Intermediate of Formula (VI) can be prepared from an intermediate of Formula (XX) in the presence of a base (for example, NaH) in a suitable solvent (e.g., THF) followed by the addition of an isothiocyanate of general formula R²—NCS. An intermediate of Formula (XX) can be treated with thiophosgene/ NMM in a suitable solvent, such as dichloromethane, to afford an intermediate isothiocyanate, which can be converted to an intermediate of Formula (VI) by using an amine of general formula NH₂—R², in the presence of a base, such as triethylamine, in a suitable solvent (such as acetonitrile).

Scheme 13

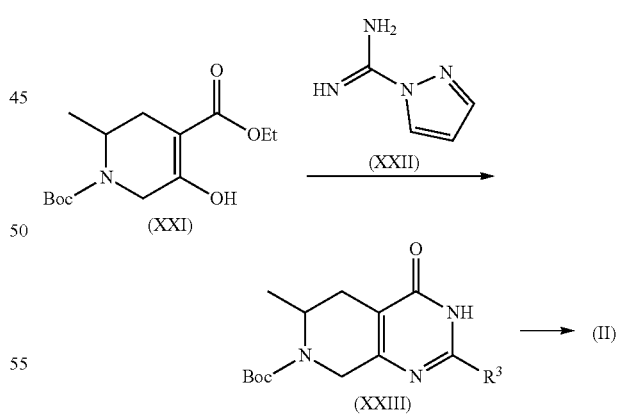

Intermediates of Formula (II) in which PG can be a protecting group, such as Boc, can be prepared from an intermediate of Formula (XXI) using a guanidine derivative of Formula (XXII) that contains a R³ as provided herein, in the presence of a base, such as DBU, in a suitable solvent (such as CH₃CN) to afford an intermediate of Formula (XXIII). An intermediate of Formula (XXIII) that contains an optionally substituted pyrazole, can be used to obtain to an intermediate of Formula (II) using methods known in the art. As an example, an intermediate of Formula (XXIII) that contains an optionally substituted pyrazole, can be reacted with an aryl or heteroaryl boronic acid of general formula R²—B(OH)₂, in the presence of TMEDA and Cu(OAc)₂ to afford an intermediate of Formula (II) in which R² represents a phenyl, a monocyclic heteroaryl or a fused-bicyclic heteroaryl.

Scheme 14

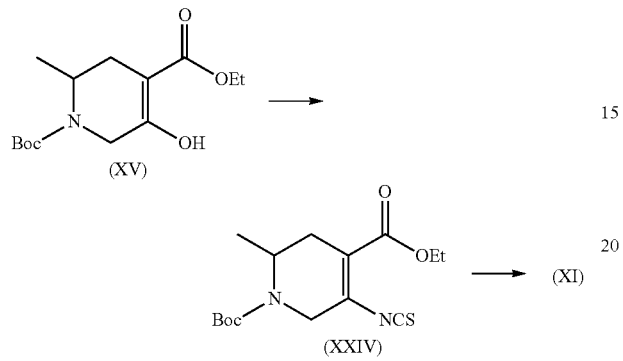

Intermediates of Formula (XI) can be obtained from an intermediate of Formula (XV) using methods known in the art, for example, by treating an intermediate of Formula (XV) with thiophosgene and NMM in a suitable solvent (such as THF). Treatment of an intermediate of Formula (XXIV) with an amine of general formula R²—NH₂ affords an intermediate of Formula (XI) in which PG represents a Boc group.

Scheme 15

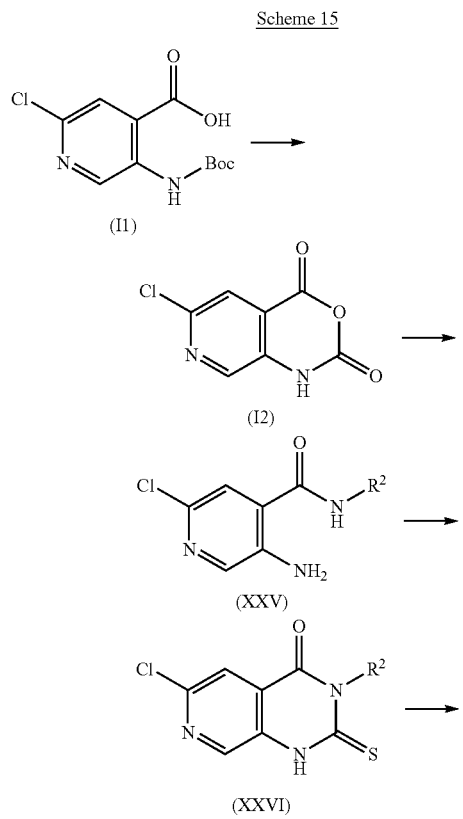

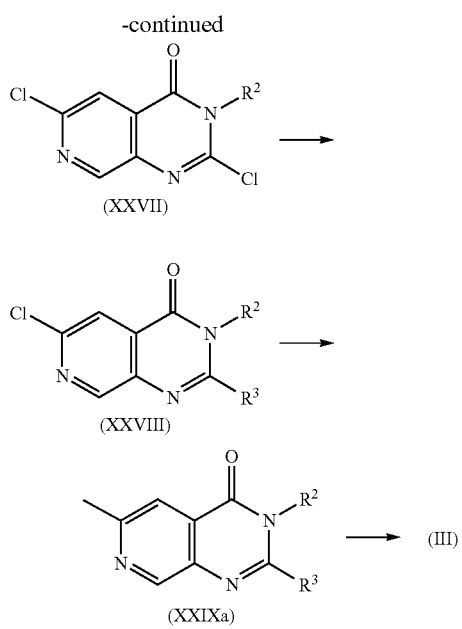

Intermediates of Formula (III), can be prepared from a chloro-N-Boc-aminopyridinecarboxylic acid intermediate of Formula (I1) using a base (such as triethylamine) in the presence of 2-chloro-N-methylpyridinium iodide in a suitable solvent (for example, acetonitrile) to afford an intermediate of Formula (I2). An intermediate of Formula (I2) can be converted to an intermediate of Formula (XXV) using an amine of general formula R²—NH₂, in a suitable solvent (for example, acetic acid). Reaction of an intermediate of Formula (XXV) with 1,1'-Thiocarbonyldiimidazole (TCDI) in DMF can afford a thio intermediate of Formula (XXVI), which can be converted in an intermediate of Formula (XXVII) using thiophosgene or sulfuryl chloride in a suitable solvent (such as 1,4-dioxane). Treatment of an intermediate of Formula (XXVII) with 3,5-dimethylpyrazole can afford an intermediate of Formula (XXVIII). Intermediates of Formula (XXVIII) that includes a R³ as provided herein, can be reacted with methylboronic acid using a Pd catalyst (e.g. Pd(Ph₃)₄) in a suitable solvent (such as dioxane/water) to afford an intermediate of Formula (XXIXa) that includes a R³ as provided herein. An intermediate of Formula (XXIXa) that includes a R³ as provided herein, can be converted to an intermediate of Formula (III) by catalytic hydrogenation using H₂ in the presence of a catalyst (for example Pt/C) in an appropriate solvent(s) (e.g., acetic acid/THF/ethanol).

Scheme 15

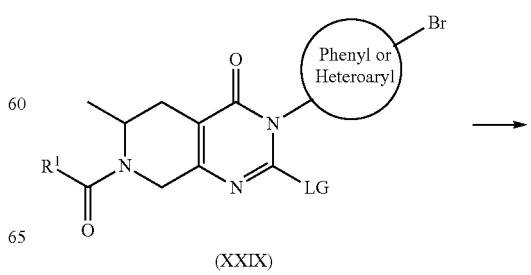

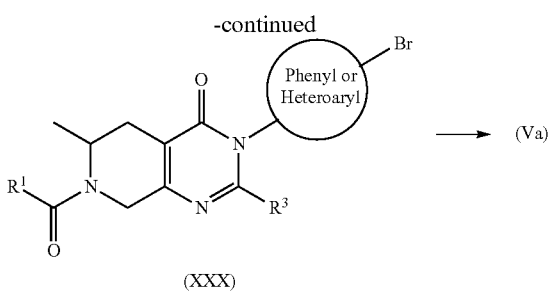

(XXX)

Intermediates of Formula (Va) can be prepared from an intermediate of Formula (XXIX), in which LG represents a leaving group (such as, sulfhydryl, methylsulfoxide or halogen (e.g., chloro or bromo). Intermediates of Formula (XXIX) can be reacted with a $R^3$ as provided herein, in the presence of a base (such as diisopropylethylamine) in a suitable solvent, such as acetonitrile, to afford an intermediate of Formula (XXX) that includes a $R^3$ as provided herein. The conversion of bromo intermediate Formula (XXX) to a boronic ester intermediate of Formula (Va) can be achieved using bis(pinacolato)diboron in the presence of a catalyst (such as Pd(dppf)Cl$_2$) in the presence of a base, such as KOAc, in a suitable solvent (for example, 1,4-dioxane).

Scheme 16

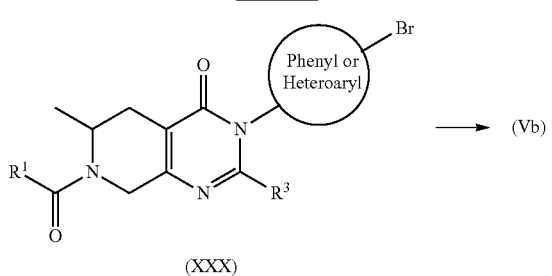

(XXX)

Intermediates of Formula (Vb) can be prepared from an intermediate of Formula (XXX) using bis(pinacolato)diboron, in the presence of a base (e.g., KOAc) and Pd(dppf)Cl$_2$ in a suitable solvent, such as 1,4-dioxane and water, to obtain an intermediate of Formula (Vb).

Scheme 17

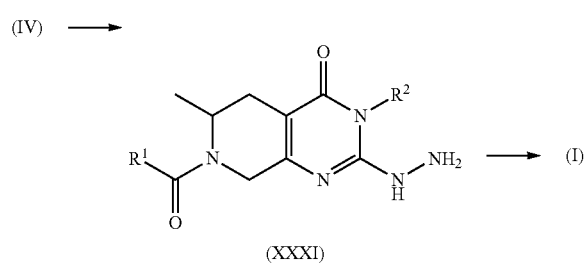

Intermediates of Formula (XXXI) can be prepared from an intermediate of Formula (IV) using hydrazine hydrate in an appropriate solvent (such as ethanol). Subsequent formation of compounds of Formula (I), including pharmaceutically acceptable salts thereof, can be accomplished by reacting intermediates of Formula (XXXI) with acetylacetone in a polar solvent (for example, ethanol) at an elevated temperature(s).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction <$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT >twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels including STOPS™ compounds) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those STOPS™ compounds described in U.S. 2020/0147124 A1, which is hereby incorporated by reference for the purpose of describing the STOPS™ compounds provided therein, such as modified oligonucleotides identified as Nos. 1-392.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

| Table of Abbreviations | |
|---|---|
| Abbreviation | Meaning |
| h | hour |
| * | single diastereomer, absolute stereochemistry unknown |
| rt | room temperature |
| EA | ethyl acetate |
| CyH | cyclohexane |
| PE | petroleum ether |
| DIPEA | diisopropylethylamine |
| SFC | Supercritical Fluid Chromatography |

4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide

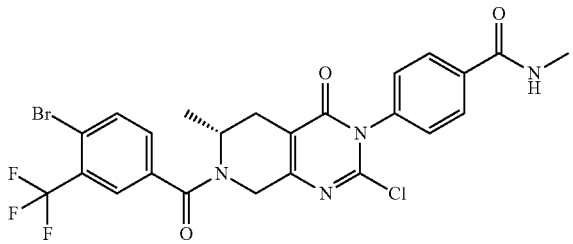 [SMILES: CNC(=O)c1ccc(-n2c(Cl)nc3c(c2=O)C[C@@H](C)N(C(=O)c2ccc(Br)c(C(F)(F)F)c2)C3)cc1]

To a solution of oxalyl dichloride (181 g, 1.43 mol) in $CH_2Cl_2$ (1.5 L) at −65° C. was added DMSO (111 mL) in $CH_2Cl_2$ (500 mL). After stirring for 1 h, t-butyl (R)-(1-hydroxypropan-2-yl)carbamate (250 g, 1.43 mol) in $CH_2Cl_2$ (500 mL) was added dropwise. After stirring for 2 h, $Et_3N$ (144 g, 1.43 mol, 198 mL) was added dropwise. The mixture was gradually warmed to 25° C. and then stirred at 25° C. for 4 h. The reaction was quenched by the addition of $NH_4Cl$ (sat., aq., 2.5 L), and then extracted with $CH_2Cl_2$ (2×2.5 L). The combined organic layers were dried over $Na_2SO_4$. The solids were removed by filtration and the filtrate was concentrated under reduced pressure to give the crude product as a colorless oil, t-butyl (R)-(1-oxopropan-2-yl)carbamate (450 g, 2.60 mol, 91% yield), which was used in the next step without further purification.

To a solution of t-butyl (R)-(1-oxopropan-2-yl)carbamate (225 g, 1.30 mol) in $CH_2Cl_2$ (2.25 L) was added (carbethoxymethylene)triphenylphosphorane (429 g, 1.23 mol). The mixture was stirred at 25° C. for 12 h. The mixture was concentrated under reduced pressure to give the crude product that was purified by silica gel column chromatography (PE:EA=15:1 to 5:1) to afford ethyl (R)-4-((t-butoxycarbonyl)amino)pent-2-enoate (500 g, 2.06 mol, 79.1% yield) as a colorless oil. $^1$H NMR ($CDCl_3$, 400 MHz) δ 6.86 (dd, J=15.76, 4.88 Hz, 1H) 5.89 (dd, J=15.70, 1.56 Hz, 1H) 4.58 (br s, 1H) 4.39 (br s, 1H) 4.18 (q, J=7.13 Hz, 2H) 1.44 (s, 9H) 1.24-1.29 (m, 6H).

To a solution of ethyl (R)-4-((t-butoxycarbonyl)amino)pent-2-enoate (125 g, 513 mmol) in $CH_3OH$ (1.25 L) was added 10% Pd/C (6.00 g) and $Pd(OH)_2$ (6.06 g) under $N_2$. The suspension was degassed under vacuum and purged with $H_2$ (1.04 g, 514 mmol) several times. The mixture was stirred under $H_2$ (50 psi) at 50° C. for 12 h. The solids were removed by filtration under $N_2$. The filtrate was evaporated to dryness to afford ethyl (R)-4-((t-butoxycarbonyl)amino)pentanoate (480 g, 1.96 mol, 95% yield) as a colorless oil. $^1$H NMR ($CDCl_3$, 400 MHz) δ 4.29-4.45 (m, 1H) 4.13 (q, J=7.13 Hz, 2H) 3.57-3.75 (m, 1H) 2.35 (t, J=7.69 Hz, 2H) 1.66-1.84 (m, 3H) 1.43 (s, 9H) 1.25 (t, J=7.13 Hz, 3H) 1.14 (d, J=6.50 Hz, 3H).

To a solution of ethyl (R)-4-((t-butoxycarbonyl)amino)pentanoate (480 g, 1.96 mol) in EA (2 L) was added HCl in EA (4M, 2.5 L). The mixture was stirred at 25° C. for 2 h. The mixture was concentrated under reduced pressure to give ethyl (R)-4-aminopentanoate HCl (450 g, crude) as a yellow oil that was used directly in the next step without purification.

To mixture of ethyl (R)-4-aminopentanoate HCl (225 g, 1.24 mol) in THF (4 L) and $H_2O$ (1 L), was added $K_2CO_3$ (427 g, 3.10 mol) at 25° C. After addition, the yellow solution was stirred at 25° C. for 30 min. A solution of ethyl 2-bromoacetate (206 g, 1.24 mol, 137 mL) dropwise at 25° C. over 30 min. The yellow solution was stirred at 25° C. for 11 h. The crude product, ethyl (R)-4-((2-ethoxy-2-oxoethyl)amino)pentanoate (400 g, 1.73 mol, 70% yield), was obtained as a colorless oil that used in the next step without work up or purification.

A solution of $(Boc)_2O$ (189 g, 865 mmol, 199 mL) was added dropwise into ethyl (R)-4-((2-ethoxy-2-oxoethyl)amino)pentanoate (200 g, 865 mmol) over 30 min. The yellow solution was stirred for 6 h at 25° C., and then pumped onto a filter. The filter cake was washed with EA (1 L), and the filtrate was collected. To the filtrate was added $H_2O$ (3 L). The mixture was extracted with EA (2×5 L). The combined organic layers were washed with brine (2 L) and dried over $Na_2SO_4$. The solids were removed by filtration. The filtrate was concentrated under reduced pressure to give the crude product, ethyl (R)-4-((t-butoxycarbonyl)(2-ethoxy-2-oxoethyl)amino)pentanoate (400 g, 1.21 mol, 70% yield), as a yellow oil, which used in the next step without purification. $^1$H NMR ($CDCl_3$, 400 MHz) δ 4.06-4.22 (m, 4H) 3.54-3.93 (m, 2H) 2.26-2.55 (m, 2H) 1.71 (qd, J=7.48, 3.69 Hz, 2H) 1.45-1.55 (m, 6H) 1.42 (s, 4H) 1.22-1.35 (m, 6H).

To a mixture of ethyl (R)-4-((t-butoxycarbonyl)(2-ethoxy-2-oxoethyl)amino)pentanoate (200 g, 603 mmol) in THF (2 L) was added t-BuOK (135 g, 1.21 mol) at 0° C. under $N_2$. The yellow mixture was stirred at 25° C. for 12 h under $N_2$. The reaction was quenched by the addition of aq. citric acid (250 g in 3 L of $H_2O$) at below 10° C. The mixture was extracted with EA (3×2.5 L). The combined organic layers were washed with brine (1×2 L) and dried over $Na_2SO_4$. The solids were removed by filtration, and the filtrate was concentrated under reduced pressure. The residue was purified by silica column chromatography (PE:EA=15:1 to 10:1) to afford 1-(t-butyl) 4-ethyl 5-oxo-2-(R)-methyl-3,6-dihydropyridine-1,4(2H)-dicarboxylate (210 g, 736 mmol, 61% yield) as a yellow oil. $^1$H NMR ($CDCl_3$, 400 MHz) δ 12.06 (s, 1H) 4.54 (br s, 1H) 4.33 (br d, J=19.39 Hz, 1H) 4.23 (dtt, J=10.62, 7.07, 7.07, 3.63, 3.63 Hz, 2H) 3.64 (br d, J=19.26 Hz, 1H) 2.45-2.55 (m, 1H) 2.18 (d, J=15.63 Hz, 1H) 1.47 (s, 9H) 1.31 (t, J=7.13 Hz, 3H) 1.11 (d, J=6.88 Hz, 3H).

To a solution of 1-(t-butyl) 4-ethyl 5-oxo-2-(R)-methyl-3,6-dihydropyridine-1,4(2H)-dicarboxylate (210 g, 736 mmol) in EA (1 L) was added a solution of HCl:EA (4 M, 2 L) dropwise at 25° C. The mixture was stirred at 25° C. for 3 h, and then concentrated under reduced pressure. The crude product was triturated with EA (500 mL) at 25° C. for 30 min to afford ethyl (R)-5-hydroxy-2-methyl-1,2,3,6-tetrahydropyridine-4-carboxylate HCl (140 g, 631 mmol, 86% yield, 100% purity) as a white solid. $^1$H NMR (Methanol-d$_4$, 400 MHz) δ 4.29 (q, J=6.96 Hz, 2H) 3.92-4.01 (m, 1H) 3.77-3.87 (m, 1H) 3.42-3.54 (m, 1H) 2.66-2.76 (m, 1H) 2.23-2.39 (m, 1H) 1.43 (d, J=6.50 Hz, 3H) 1.32 (t, J=7.07 Hz, 3H).

A solution of ethyl (R)-5-hydroxy-2-methyl-1,2,3,6-tetrahydropyridine-4-carboxylate HCl (115 g, 519 mmol), in DMF (1 L) was cooled to 0° C. DIPEA (268 g, 2.08 mol, 361 mL), and T$_3$P (495 g, 778 mmol, 463 mL, 50% purity) were added. The mixture was stirred at 25° C. for 12 h. The reaction was quenched by the addition water 2 L at 25° C. The mixture was diluted with EA (1.5 L) and extracted with EA (3×1 L). The combined organic layers were washed with brine (500 mL) and dried over Na$_2$SO$_4$. The solids were removed by filtration, and the filtrate was concentrated under reduced pressure. The residue was purified by silica gel chromatography (0 to 10% EA:PE gradient) to afford ethyl (R)-1-(4-bromo-3-(trifluoromethyl)benzoyl)-5-hydroxy-2-methyl-1,2,3,6-tetrahydropyridine-4-carboxylate (130 g, 259 mmol, 50% yield, 87% purity) as a yellow oil. $^1$H NMR (CDCl$_3$, 400 MHz), δ 12.10 (br s, 1H) 7.80 (d, J=8.13 Hz, 1H) 7.74 (d, J=1.88 Hz, 1H) 7.42 (dd, J=8.13, 1.88 Hz, 1H) 4.64-5.30 (m, 1H) 4.19-4.34 (m, 2H) 4.08-4.17 (m, 1H) 3.81 (br dd, J=12.13, 2.75 Hz, 1H) 2.58 (br d, J=14.76 Hz, 1H) 2.24 (br d, J=16.01 Hz, 1H) 1.32 (t, J=7.13 Hz, 3H) 1.25 (br t, J=3.13 Hz, 3H).

To a solution of ethyl (R)-1-(4-bromo-3-(trifluoromethyl)benzoyl)-5-hydroxy-2-methyl-1,2,3,6-tetrahydropyridine-4-carboxylate (90.0 g, 206 mmol) in ethanol (900 mL) was added NH$_4$OAc (79.5 g, 1.03 mol). The mixture was stirred at 60° C. for 2 h. The mixture was concentrated under reduced pressure, diluted with water (200 mL) and extracted with EA (3×200 mL). The combined organic layers were washed with brine (200 mL) and dried over Na$_2$SO$_4$. The solids were removed by filtration, and the filtrate was concentrated under reduced pressure. The residue was purified by silica gel chromatography (0 to 50% EA:PE gradient) to afford ethyl (R)-5-amino-1-(4-bromo-3-(trifluoromethyl)benzoyl)-2-methyl-1,2,3,6-tetrahydropyridine-4-carboxylate (55.0 g, 125 mmol, 61% yield, 99% purity) as a yellow solid. $^1$H-NMR (DMSO-d$_6$, 400 MHz) δ 7.98 (d, J=8.13 Hz, 1H) 7.84 (d, J=1.75 Hz, 1H) 7.63 (dd, J=8.19, 1.56 Hz, 1H) 6.74-7.47 (m, 2H) 4.63-4.91 (m, 1H) 4.00-4.08 (m, 2H) 3.80-3.95 (m, 1H) 3.59-3.75 (m, 1H) 2.45 (br d, J=5.75 Hz, 1H) 2.14 (br d, J=1.25 Hz, 1H) 1.06-1.20 (m, 6H).

To a solution of ethyl (R)-5-amino-1-(4-bromo-3-(trifluoromethyl)benzoyl)-2-methyl-1,2,3,6-tetrahydropyridine-4-carboxylate (100 g, 230 mmol) and NMM (102 g, 1.01 mol, 111 mL) in CH$_2$Cl$_2$ (1 L) was added SCCl$_2$ (55.5 g, 483 mmol, 37.0 mL) at 0° C. The mixture was stirred at 0° C. for 1 h. The reaction was quenched by the addition ice-water (100 mL) at 0° C. The mixture was diluted with CH$_2$Cl$_2$ (150 mL) and extracted with CH$_2$Cl$_2$ (3×500 mL). The combined organic layers were washed with brine (500 mL) and dried over Na$_2$SO$_4$. The solids were removed by filtration, and the solvent of the filtrate was concentrated under reduced pressure. The residue was purified by silica gel chromatography (0 to 20% EA:PE gradient) to afford ethyl (R)-1-(4-bromo-3-(trifluoromethyl)benzoyl)-5-isothiocyanato-2-methyl-1,2,3,6-tetrahydropyridine-4-carboxylate (100 g, 163 mmol, 71% yield, 78% purity) as a yellow oil. $^1$H-NMR (CDCl$_3$, 400 MHz) δ 7.74 (d, J=8.13 Hz, 1H) 7.66 (d, J=1.75 Hz, 1H) 7.34 (dd, J=8.13, 2.00 Hz, 1H) 4.55-5.18 (m, 1H) 4.14-4.26 (m, 3H) 3.67-3.85 (m, 2H) 2.51-2.70 (m, 1H) 2.31-2.47 (m, 1H) 1.29 (t, J=7.13 Hz, 3H) 1.18 (dd, J=7.00, 3.38 Hz, 4H).

To a solution of ethyl (R)-1-(4-bromo-3-(trifluoromethyl)benzoyl)-5-isothiocyanato-2-methyl-1,2,3,6-tetrahydropyridine-4-carboxylate (100 g, 210 mmol) in CH$_3$CN (1 L) were added 4-amino-N-methylbenzamide (31.5 g, 210 mmol) and Et$_3$N (53.0 g, 524 mmol, 72.9 mL). The mixture was stirred at 95° C. for 12 h to obtain a yellow suspension. The mixture was concentrated under reduced pressure. The crude product was triturated with EA (500 mL) at 25° C. for 1 h to afford (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 119 mmol, 57% yield, 86% purity) as a white solid. $^1$H-NMR (DMSO-d$_6$, 400 MHz) δ 8.49-8.57 (m, 1H) 8.02 (br d, J=7.63 Hz, 1H) 7.88 (m, 3H) 7.69 (br d, J=7.63 Hz, 1H) 7.29 (br d, J=8.88 Hz, 1H) 7.25 (br s, 1H) 5.08-5.27 (m, 1H) 4.18-4.35 (m, 1H) 4.05-4.14 (m, 1H) 2.80 (d, J=4.50 Hz, 3H) 2.53-2.62 (m, 1H) 2.17-2.36 (m, 1H) 1.18-1.20 (m, 3H).

To a solution of (R)-4-(7-(4-bromo-3-(trifluoromethyl)benzoyl)-6-methyl-4-oxo-2-thioxo-1,4,5,6,7,8-hexahydropyrido[3,4-d]pyrimidin-3(2H)-yl)-N-methylbenzamide (80.0 g, 138 mmol) in dioxane (880 mL) was added SCCl$_2$ (31.6 g, 275 mmol, 21.1 mL). The mixture was stirred at 100° C. for 2 h and then concentrated under reduced pressure. The residue was purified by silica gel chromatography (0 to 80% EA:PE gradient) to afford 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (49.0 g, 81.5 mmol, 59% yield, 97% purity) as an off-white solid. $^1$H-NMR (CD$_3$OD, 400 MHz) δ 7.94-8.03 (m, 3H) 7.90 (d, J=1.75 Hz, 1H) 7.61-7.68 (m, 1H) 7.42-7.54 (m, 2H) 5.02-5.49 (m, 1H) 4.13-4.56 (m, 2H) 2.95 (s, 3H) 2.72-2.86 (m, 1H) 2.56 (br d, J=17.89 Hz, 1H) 1.24-1.38 (m, 3H).

Example 1

Compounds 1 & 2

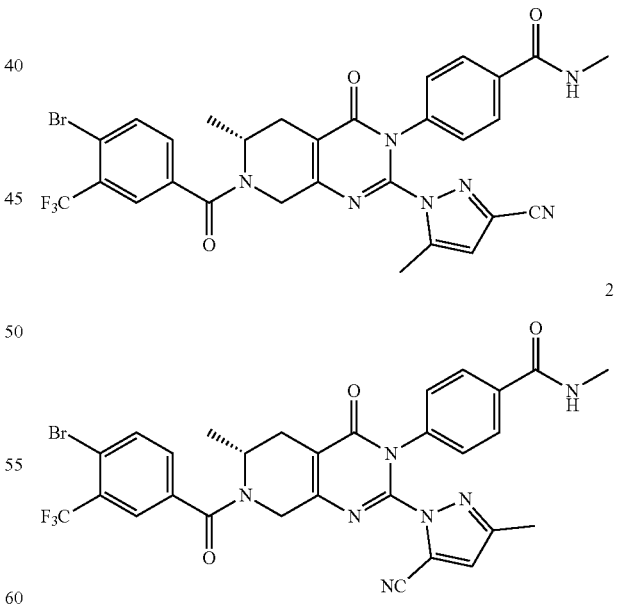

General Procedure A. Triethylamine (0.25 mL, 1.8 mmol) was added to a solution of 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (150 mg, 0.26 mmol) and 5-methyl-1H-pyrazole-3-carbonitrile (82.57 mg, 0.77 mmol) in anhydrous CH$_3$CN (3 mL)

under $N_2$. The mixture was stirred at 130° C. for 18 h. $NaHCO_3$ (sat., aq.) was added, and the mixture was extracted with EA (3×). The combined organic phases were washed with water and brine and dried over $Na_2SO_4$. The solids were removed by filtration and the filtrate was evaporated to dryness. The crude mixture was purified by flash chromatography on silica gel (0 to 5% $CH_3OH$ in $CH_2Cl_2$) to afford a beige solid. The solid was purified by SFC (30:70, $CH_3OH:CO_2$) to afford two products as white solids. (R)-4-(7-(4-bromo-3-(trifluoromethyl)benzoyl)-2-(3-cyano-5-methyl-1H-pyrazol-1-yl)-6-methyl-4-oxo-5,6,7,8-tetrahydropyrido[3,4-d]pyrimidin-3(4H)-yl)-N-methylbenzamide (1) (84 mg, 50%). $^1$H-NMR (DMSO-$d_6$, 400 MHz, 80° C.): 1.28 (d, J=6.7 Hz, 3H), 2.42 (s, 3H), 2.57 (d, J 16.8 Hz, 1H), 2.74-2.84 (m, 4H), 4.31 (d, J=20.3 Hz, 1H), 4.59 (br. s., 1H), 4.80 (br. s., 1H), 6.70 (s, 1H), 7.33 (d, J=7.8 Hz, 2H), 7.70 (dd, J=8.2 Hz, 1.7 Hz, 1H), 7.81 (d, J=8.9 Hz, 2H), 7.88 (d, J=1.4 Hz, 1H), 8.0 (d, J=8.0 Hz, 1H), 8.26-8.31 (m, 1H) ppm. LC-MS: $C_{29}H_{23}BrF_3N_7O_3$ [M+H]$^+$: 654/656. (R)-4-(7-(4-bromo-3-(trifluoromethyl)benzoyl)-2-(5-cyano-3-methyl-1H-pyrazol-1-yl)-6-methyl-4-oxo-5,6,7,8-tetrahydropyrido[3,4-d]pyrimidin-3(4H)-yl)-N-methylbenzamide (2) (10 mg, 6%). $^1$H-NMR (DMSO-$d_6$, 400 MHz, 80° C.): 1.28 (d, J=6.2 Hz, 3H), 1.97 (s, 3H), 2.52-2.59 (m, 1H), 2.74-2.84 (m, 4H), 4.28 (d, J=20.3 Hz, 1H), 4.54 (br. s., 1H), 4.82 (br. s., 1H), 7.10 (s, 1H), 7.33 (d, J=8.6 Hz, 2H), 7.70 (dd, J=8.2 Hz, 1.7 Hz, 1H), 7.81 (d, J=8.9 Hz, 2H), 7.88 (d, J=1.4 Hz, 1H), 8.0 (d, J=8.0 Hz, 1H), 8.26-8.31 (m, 1H) ppm. LC-MS: $C_{29}H_{23}BrF_3N_7O_3$ [M+H]$^+$: 654/656.

Example 2

Compound 3

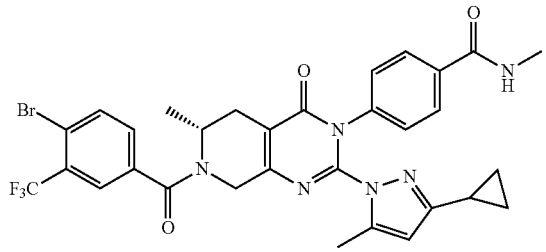 [SMILES: CNC(=O)c1ccc(-n2c(-n3nc(C4CC4)cc3C)nc3c(c2=O)C[C@@H](C)N(C(=O)c2ccc(Br)c(C(F)(F)F)c2)C3)cc1]

General Procedure B. NaH (60% dispersion in oil, 15.073 mg, 0.38 mmol) was added, at 0° C., to a solution of 3-cyclopropyl-5-methyl-1H-pyrazole (23.02 mg, 0.19 mmol) in anhydrous DMF (1 mL) under $N_2$. The mixture was stirred for 5 min, and then 4-[(6R)-7-[4-bromo-3-(trifluoromethyl)benzoyl]-2-chloro-6-methyl-4-oxo-3H,4H,5H,6H,7H,8H-pyrido[3,4-d]pyrimidin-3-yl]-N-methylbenzamide (100 mg, 0.17 mmol) was added. The mixture was allowed to warm to rt and the stirred for 1 h. Water was added, and the mixture was extracted with EA (3×). The combined organic phases were washed with water and brine, and dried over $Na_2SO_4$. The solids were removed by filtration and the filtrate was evaporated to dryness. The crude mixture was purified by chromatography on silica gel (0 to 5% $CH_3OH$ in $CH_2Cl_2$) to afford (R)-4-(7-(4-bromo-3-(trifluoromethyl)benzoyl)-2-(3-cyclopropyl-5-methyl-1H-pyrazol-1-yl)-6-methyl-4-oxo-5,6,7,8-tetrahydropyrido[3,4-d]pyrimidin-3(4H)-yl)-N-methylbenzamide (3) (22 mg, 19%) as a white solid. $^1$H-NMR (DMSO-$d_6$, 400 MHz, 80° C.): 0.20-0.36 (m, 2H), 0.56-0.70 (m, 2H), 1.26 (d, J=6.9 Hz, 3H), 1.47-1.60 (m, 1H), 2.34 (s, 3H), 2.42-2.55 (m, 1H), 2.64-2.75 (m, 1H), 2.80 (d, J=4.6 Hz, 3H), 4.26 (d, J=19.6 Hz, 1H), 4.40-5.01 (m, 2H), 5.84 (s, 1H), 7.23 (d, J=8.1 Hz, 2H), 7.70 (dd, J=8.0 Hz, 1.3 Hz, 1H), 7.77 (d, J=8.6 Hz, 2H), 7.88 (d, J=1.3 Hz, 1H), 7.99 (d, J=8.0 Hz, 1H), 8.20-8.26 (m, 1H) ppm. LC-MS: $C_{31}H_{28}BrF_3N_6O_3$ [M+H]$^+$: 669/671.

The compounds in Table 1 were prepared according to the method indicated.

TABLE 1

| Compound | General Procedure | Structure | LC-MS [M + H]$^+$ | $^1$H-NMR |
|---|---|---|---|---|
| 4 | B | 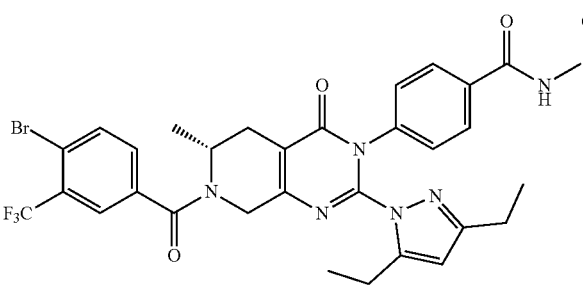 | 671/673 | $^1$H-NMR (DMSO-$d_6$, 400 MHz, 80° C.): 0.84 (t, J = 7.6 Hz, 3H), 1.16 (t, J = 7.5 Hz, 3H), 1.25 (d, J = 6.5 Hz, 3H), 2.21 (q, J = 7.5 Hz, 2H), 2.51-2.55 (m, 2H), 2.68-2.74 (m, 2H), 2.77 (d, J = 4.5 Hz, 3H), 4.25 (d, J = 19.3 Hz, 1H), 4.34-5.00 (m, 2H), 5.85 (s, 1H), 7.21 (d, J = 8.1 Hz, 2H), 7.66 (dd, J = 8.1, 1.4 Hz, 1H), 7.75 (d, J = 8.1 Hz, 2H), 7.87 (d, J = 1.5 Hz, 1H), 7.98 (d, J = 8.1 Hz, 1H), 8.13-8.29 (m, 1H) ppm. |

TABLE 1-continued

| Compound | General Procedure | Structure | LC-MS [M + H]+ | 1H-NMR |
|---|---|---|---|---|
| 5 | A | 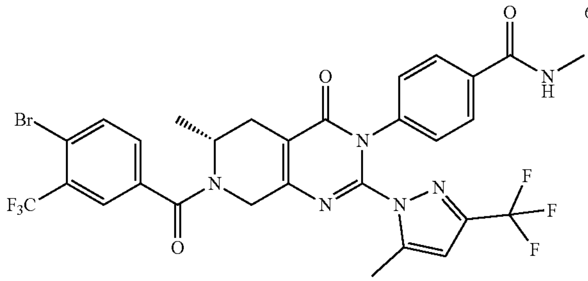 | 697/699 | 1H-NMR (DMSO-d6, 400 MHz, 80° C.): 1.28 (d, J = 6.9 Hz, 3H), 2.42 (s, 3H), 2.54-2.59 (m, 1H), 2.78 (d, J = 4.5 Hz, 3H), 2.81-2.82 (m, 1H), 4.28-4.33 (m, 1H), 4.58-4.60 (m, 1H), 4.78-4.83 (m, 1H), 6.48 (s, 1H), 7.30 (d, J = 8.1 Hz, 2H), 7.70 (dd, J = 8.1; 1.9 Hz, 1H), 7.79 (d, J = 8.8 Hz, 2H), 7.88 (d, J = 1.8 Hz, 1H), 8.01 (d, J = 8.1 Hz, 1H), 8.26-8.27 (m, 1H) ppm. |
| 6 | B | 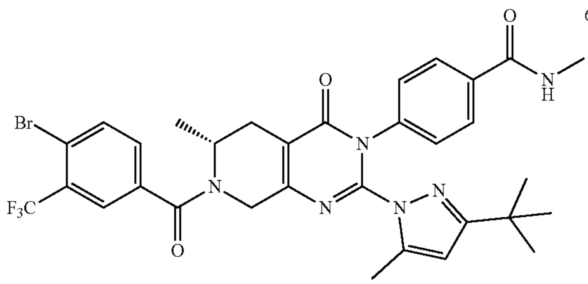 | 685/687 | 1H-NMR (DMSO-d6, 400 MHz, 80° C.): 0.92 (s, 9H), 1.27 (d, J = 6.6 Hz, 3H), 2.37 (s, 3H), 2.51-2.58 (m, 1H), 2.71-2.76 (m, 1H), 2.79 (d, J = 4.7 Hz, 3H), 4.22-4.34 (m, 1H), 4.55 (br. s., 1H), 4.79 (br. s., 1H), 5.98 (d, J = 0.8 Hz, 1H), 7.22 (d, J = 7.8 Hz, 2H), 7.70 (dd, J = 8.1 Hz, 1.9 Hz, 1H), 7.75-7.78 (m, 2H), 7.88 (d, J = 2.0 Hz, 1H), 8.0 (d, J = 8.1 Hz, 1H), 8.16-8.21 (m, 1H) ppm. |
| 7 | B | 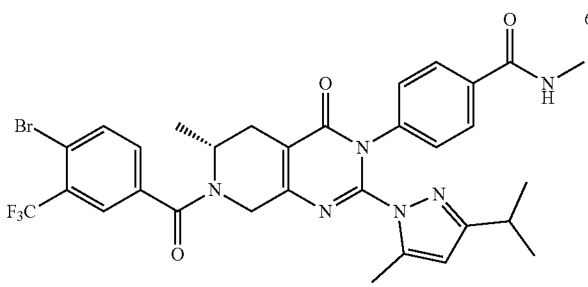 | 671/673 | 1H-NMR (DMSO-d6, 400 MHz, 80° C.): 0.82-0.92 (m, 6H), 1.27 (d, J = 6.8 Hz, 3H), 2.35 (s, 3H), 2.55-2.59 (m, 1H), 2.69-2.76 (m, 1H), 2.79 (d, J = 4.5 Hz, 3H), 3.01-3.05 (m, 1H), 4.20-4.36 (m, 1H), 4.40-4.96 (m, 2H), 5.87 (s, 1H), 7.23 (d, J = 8.1 Hz, 2H), 7.70 (dd, J = 8.3 Hz, 1.6 Hz, 1H), 7.76 (d, J = 8.8 Hz, 2H), 7.88 (d, J = 1.6 Hz, 1H), 8.00 (d, J = 8.1 Hz, 1H), 8.13-8.27 (m, 1H) ppm. |
| 8 | B | 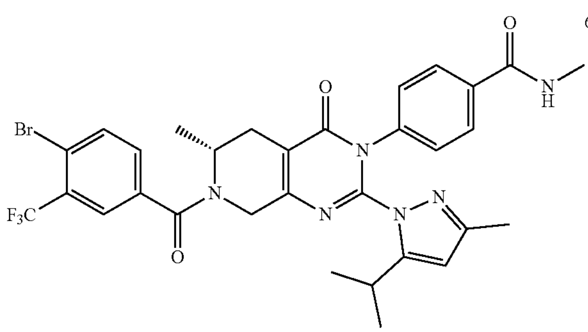 [SMILES: CNC(=O)c1ccc(-n2c(-n3nc(C)cc3C(C)C)nc3c(c2=O)C[C@@H](C)N(C(=O)c2ccc(Br)c(C(F)(F)F)c2)C3)cc1] | 671/673 | 1H-NMR (DMSO-d6, 400 MHz, 80° C.): 1.13-1.20 (m, 6H), 1.26 (d, J = 6.8 Hz, 3H), 1.87 (s, 3H), 2.54-2.58 (m, 1H), 2.73-2.87 (m, 4H), 3.12-3.22 (m, 1H), 4.16-4.37 (m, 1H), 4.39-4.94 (m, 2H), 5.86 (s, 1H), 7.25 (d, J = 8.1 Hz, 2H), 7.70 (dd, J = 8.3 Hz, 1.6 Hz, 1H), 7.77 (d, J = 8.3 Hz, 2H), 7.88 (d, J = 1.6 Hz, 1H), 8.00 (d, J = 8.1 Hz, 1H), 8.17-8.30 (m, 1H) ppm. |
| 9 | A | 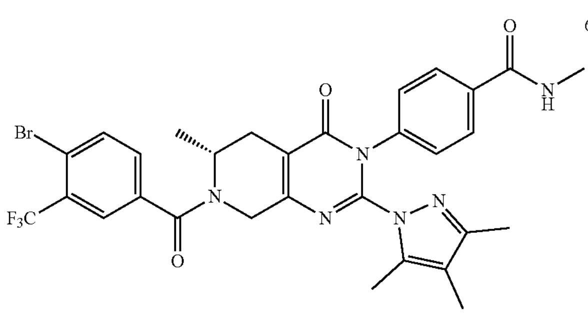 [SMILES: CNC(=O)c1ccc(-n2c(-n3nc(C)c(C)c3C)nc3c(c2=O)C[C@@H](C)N(C(=O)c2ccc(Br)c(C(F)(F)F)c2)C3)cc1] | 657/659 | 1H-NMR (DMSO-d6, 400 MHz, 80° C.): 1.27 (d, J = 6.9 Hz, 3H), 1.77 (s, 3H), 1.80 (s, 3H), 2.26 (s, 3H), 2.50-2.57 (m, 1H), 2.70-2.76 (m, 1H), 2.80 (d, J = 4.4 Hz, 3H), 4.17-4.30 (m, 1H), 4.42-4.91 (m, 2H), 7.26 (d, J = 8.4 Hz, 2H), 7.69 (dd, J = 8.4 Hz, 1.5 Hz, 1H), 7.76 (d, J = 8.6 Hz, 2H), 7.88 (d, J = 1.8 Hz, 1H), 7.99 (d, J = 8.1 Hz, 1H), 8.19-8.27 (m, 1H) ppm. |

TABLE 1-continued

| Compound | General Procedure | Structure | LC-MS [M + H]+ | 1H-NMR |
|---|---|---|---|---|
| 10 | A | 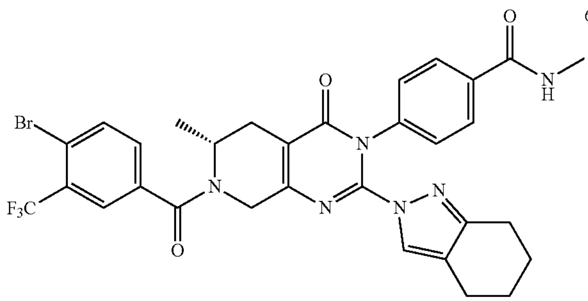 [SMILES: CNC(=O)c1ccc(-n2c(-n3cc4c(n3)CCCC4)nc3c(c2=O)C[C@@H](C)N(C(=O)c2ccc(Br)c(C(F)(F)F)c2)C3)cc1] | 669/671 | 1H-NMR (DMSO-d6, 400 MHz, 80° C.): 1.24 (d, J = 7.2 Hz, 3H), 1.51-1.64 (m, 4H), 2.20-2.26 (m, 2H), 2.39-2.44 (m, 2H), 2.50-2.52 (m, 1H), 2.66-2.76 (m, 1H), 2.79 (d, J = 4.5 Hz, 3H), 4.23 (d, J = 19.4 Hz, 1H), 4.34-4.87 (m, 2H), 7.27 (d, J = 8.3 Hz, 2H), 7.68 (dd, J = 8.3 Hz, 1.9 Hz, 1H), 7.73-7.81 (m, 3H), 7.85-7.90 (m, 1H), 7.98 (d, J = 8.1 Hz, 1H), 8.20-8.27 (m, 1H) ppm. |
| 11 | B | 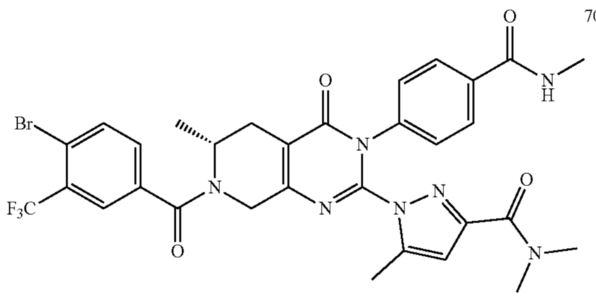 | 700/702 | 1H-NMR (DMSO-d6, 400 MHz, 80° C.): 1.28 (d, J = 6.8 Hz, 3H), 2.44 (s, 3H), 2.53-2.89 (m, 11H), 4.29 (d, J = 19.6 Hz, 1H), 4.58 (br. s., 1H), 4.80 (br. s., 1H), 6.31 (d, J = 0.8 Hz, 1H), 7.33 (d, J = 8.2 Hz, 2H), 7.70 (dd, J = 8.0 Hz, 1.9 Hz, 1H), 7.78 (d, J = 8.8 Hz, 2H), 7.88 (d, J = 1.7 Hz, 1H), 8.00 (d, J = 8.3 Hz, 1H), 8.18-8.26 (m, 1H) ppm. |
| 12 | B | 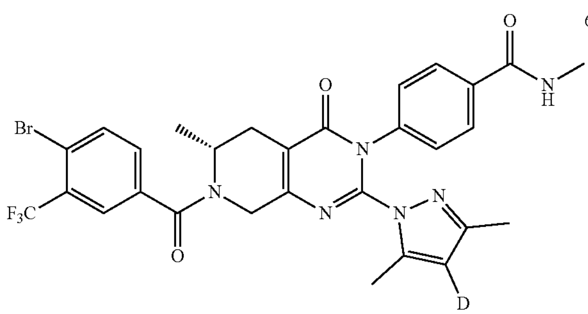 [SMILES: [2H]c1c(C)nn(-c2nc3c(c(=O)n2-c2ccc(C(=O)NC)cc2)C[C@@H](C)N(C(=O)c2ccc(Br)c(C(F)(F)F)c2)C3)c1C] | 644/646 | 1H-NMR (DMSO-d6, 400 MHz, 80° C.): 1.26 (d, J = 6.8 Hz, 3H), 1.84 (s, 3H), 2.32 (s, 3H), 2.51-2.58 (m, 1H), 2.72-2.86 (m, 1H), 2.79 (d, J = 4.6 Hz, 3H), 4.19-4.35 (m, 1H), 4.42-4.95 (m, 2H), 7.26 (d, J = 8.4 Hz, 2H), 7.70 (d, J = 9.0 Hz, 1H), 7.76 (d, J = 8.4 Hz, 2H), 7.86-7.91 (m, 1H), 8.00 (d, J = 8.0 Hz, 1H), 8.19-8.27 (m, 1H) ppm. |

Example 3

Additional Compounds

Additional compounds can be prepared using similar materials and methods described herein, such as those described herein.

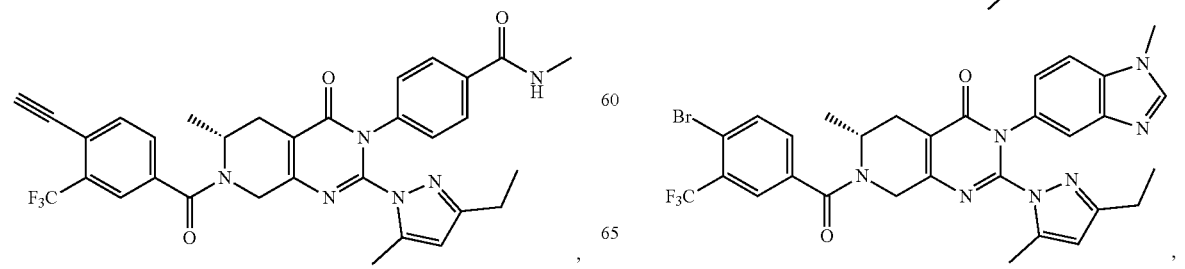

91
-continued
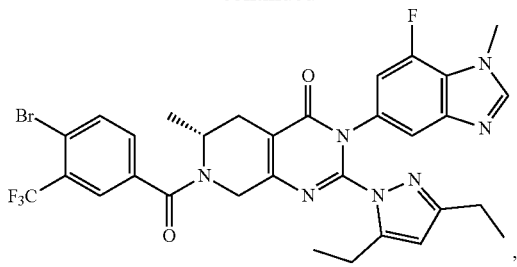
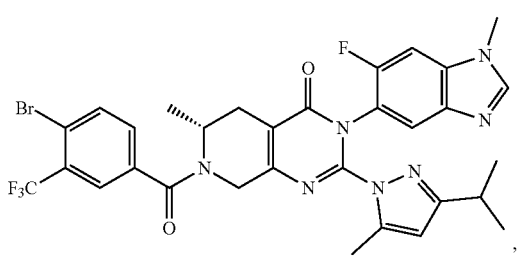
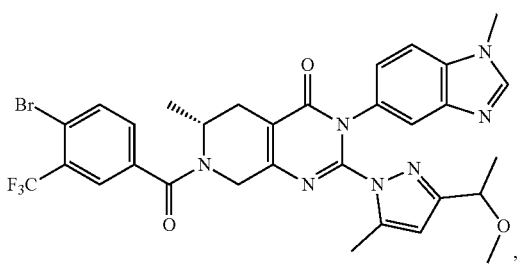
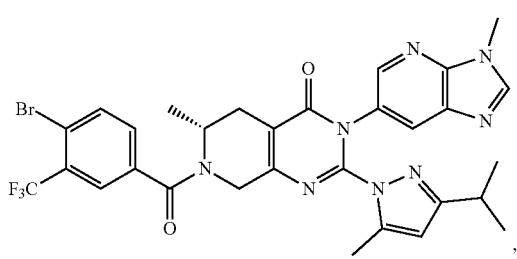
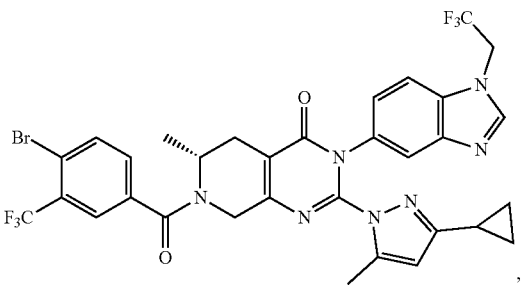
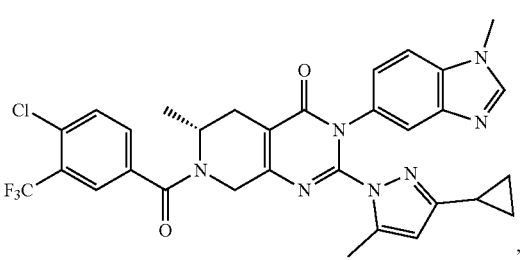
92
-continued
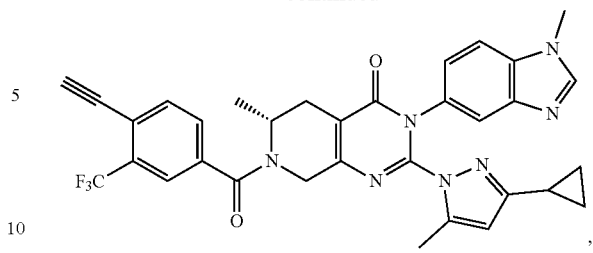
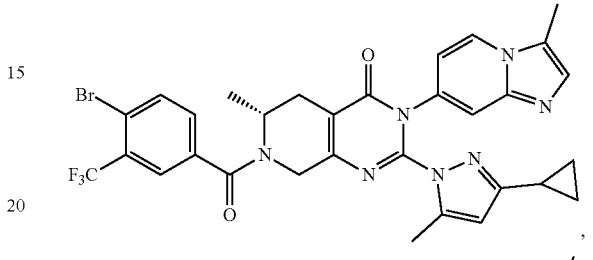
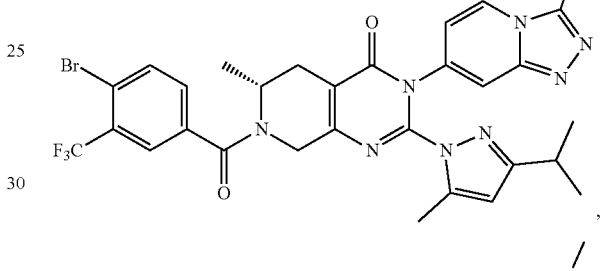
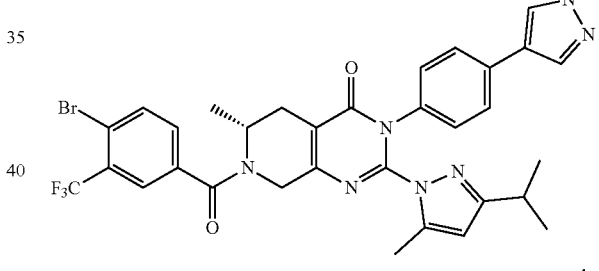
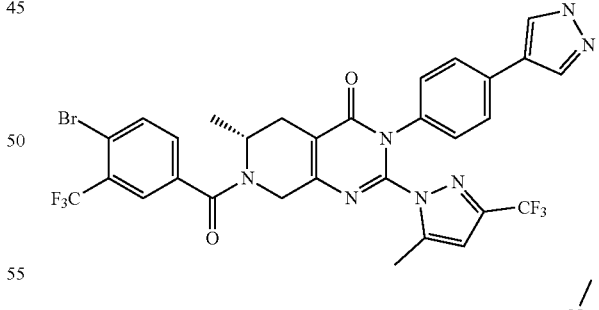
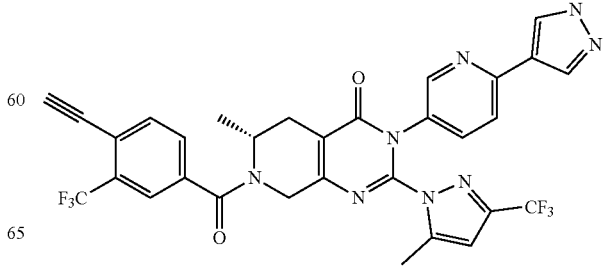

93
-continued
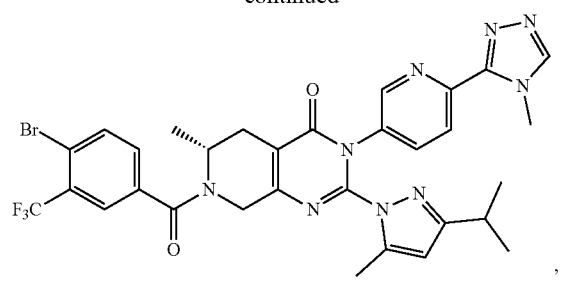
,
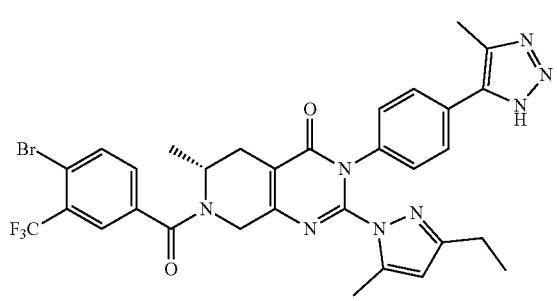
,
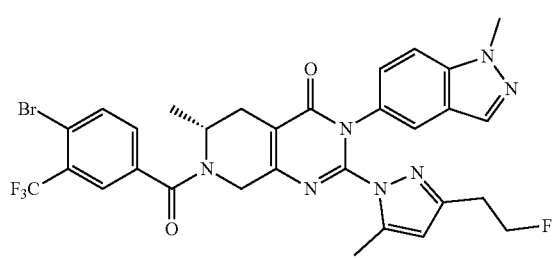
,
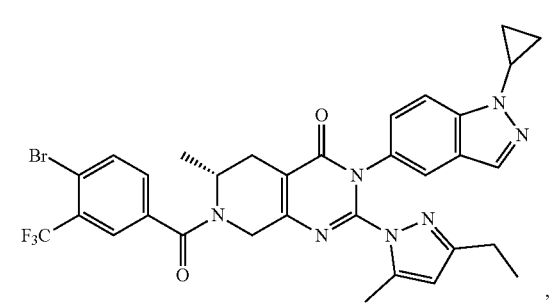
,
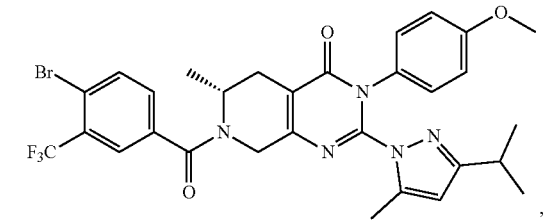
,
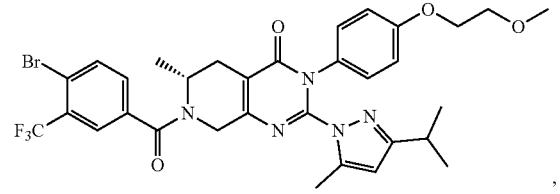
,
94
-continued
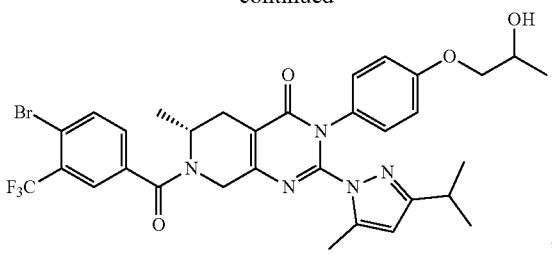
,
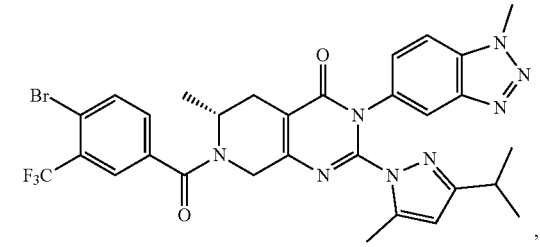
,
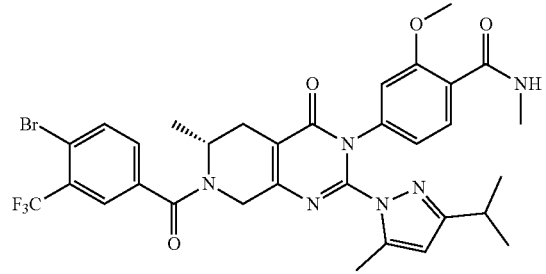
,
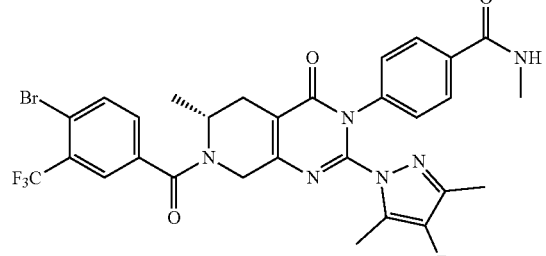
,
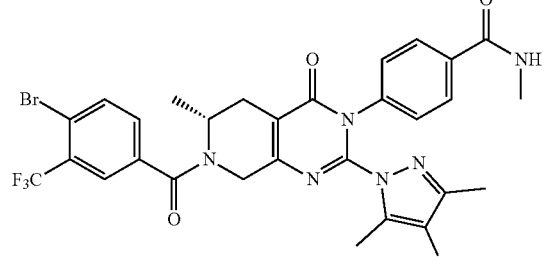
,
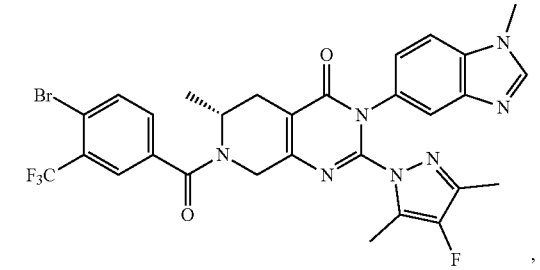
, -continued

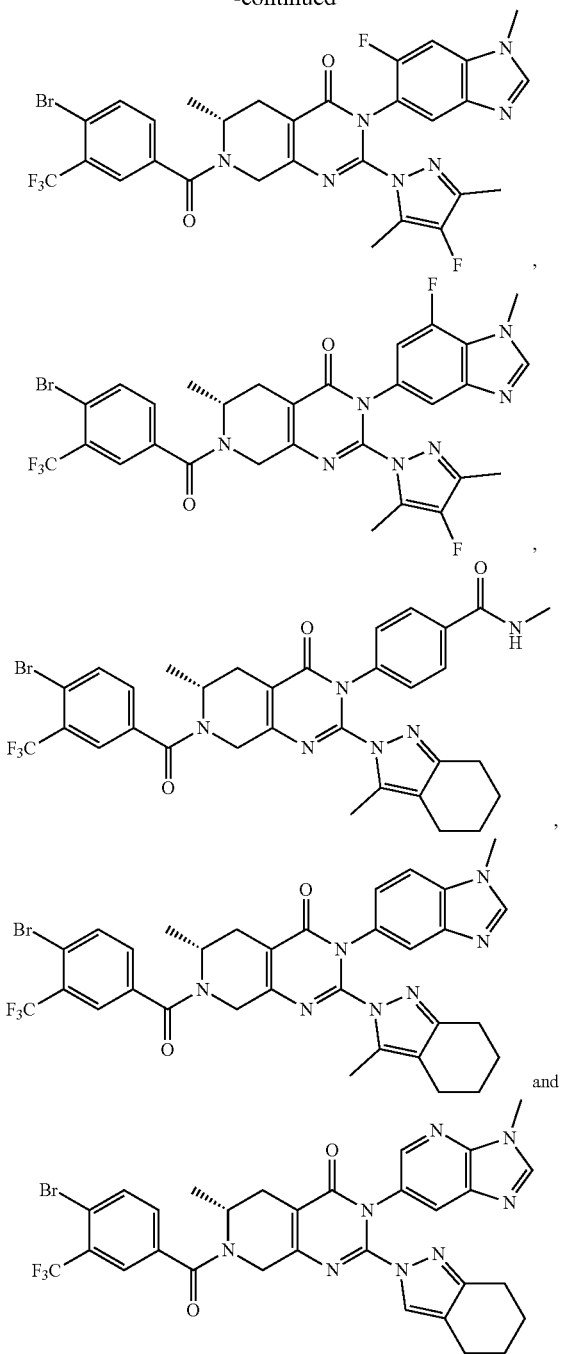

(including pharmaceutically acceptable salts of any of the foregoing).

Example A

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using CellTiter-Glo 2.0 (Promega).

On day 0, HepG2.117 cells (which are maintained in routine cell culture with doxycycline present in the medium at a final concentration of 1 μg/mL) are seeded in 96-well plates (white with clear bottom) at a density of $2.0 \times 10^4$ cells/well (0.1 mL/well) in medium without doxycycline to induce pgRNA transcription and subsequent formation of HBV particles. The cells are incubated at 37° C. and 5% $CO_2$.

On day 1, medium is removed from each well, the test articles are diluted in culture medium without doxcycyline and 100 μL was added to cell culture wells (9 concentrations, 4-fold dilution). For each plate, 6 untreated (merely DMSO) wells are included. The final concentration of DMSO in the culture medium is 2%. Each plate is prepared in duplicate (one for HBV DNA extraction, one for CellTiter-Glo 2.0 measurement). The cells are incubated at 37° C. and 5% $CO_2$ for 3 days.

On day 4, cell viability is assessed using CellTiter-Glo 2.0 and cell lysates are prepared for HBV DNA extraction and subsequent quantification by qPCR.

HBV DNA Quantification by qPCR

Medium is removed from each well and 100 μL of 0.33% NP-40 in $H_2O$ was added to each well. Plates are sealed, incubated at 4° C. for 5 mins, vortexed extensively and centrifuged briefly. Next, 35 μL of lysate is added to 65 μL QuickExtract DNA Extraction Solution (Epicentre) in a PCR plate for each well. PCR plate is incubated at 65° C. for 6 mins, 98° C. for 2 mins and finally cooled to 4° C. HBV DNA is then quantified by qPCR with HBV-specific primers and probes as specified in Table 2 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 2

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM/CCTCTKCAT/ZEN/CCTGCTGCTATGC CTCATC/3IABKFQ/ (SEQ ID NO: 3) |

A DNA standard is prepared by dilution of an IDT gBlock corresponding to the amplicon with concentrations ranging from $10^2$ to $10^8$ copies/input (i.e., per 4 μL) and used to generate a standard curve by plotting Cq values vs. HBV DNA standard concentration. The quantity of HBV DNA in each sample is determined by interpolating from the standard curve.

Cell Viability

Using the other plates, the cell viability is quantified by CellTiter-Glo 2.0 according to the manufacturer's manual. In brief, 100 μL of reagent solution is added to the culture plates and shaken for 2'. The plates are incubated at rt for 10 min and luminescence signal is subsequently measured on a VarioSkan Lux (ThermoFisher) plate reader.

Data Analysis

Cell viability is calculated as follows: % Cell viability=(luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir is required due to the excellent dynamic window of this assay. The $CC_{50}$, $EC_{50}$ and $EC_{90}$ values were determined by dose-response curves fitted using non-linear regression.

As shown in Table 3, compounds of Formula (I) are active against HBV, where 'A' indicates an $EC_{50} \leq 50$ nM, 'B' indicates an $EC_{50} > 50$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 3

| Compound | $EC_{50}$ (nM) | $CC_{50}$ (nM) |
|---|---|---|
| 1 | A | >50000 |
| 2 | A | 29222 |
| 3 | A | >50000 |
| 4 | A | >50000 |
| 5 | A | >500 |
| 6 | A | 41795 |
| 7 | A | >50000 |
| 8 | A | >50000 |
| 9 | B | >5000 |
| 10 | A | >50000 |
| 11 | B | >50000 |
| 12 | A | >50000 |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:
1. A compound of Formula (I), or a pharmaceutically acceptable salt thereof, having the structure:
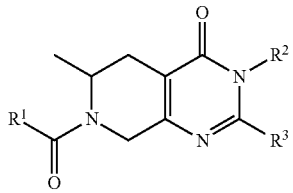
wherein:
$R^1$ is a substituted phenyl;
$R^2$ is selected: from the group consisting of
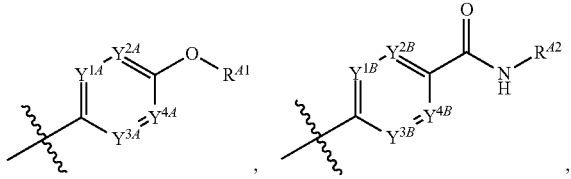
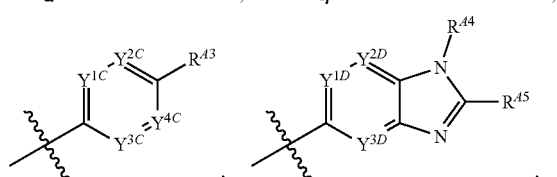
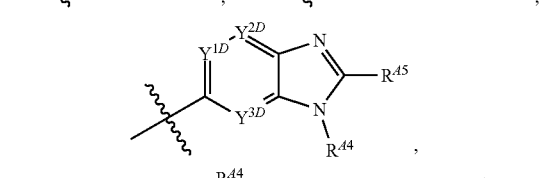
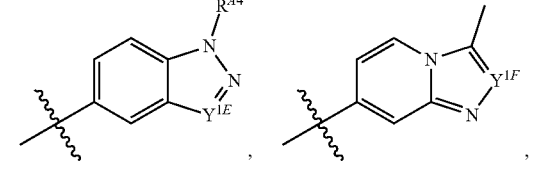
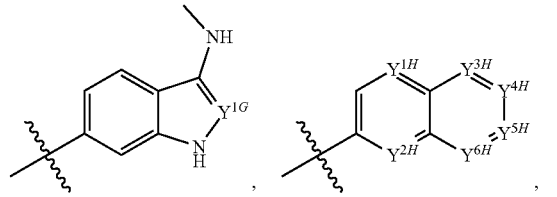
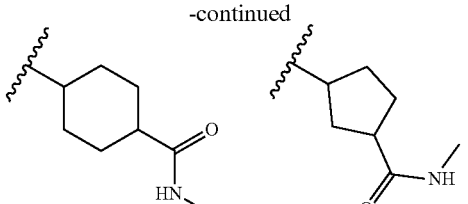
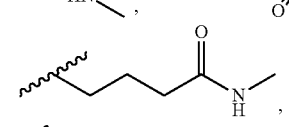
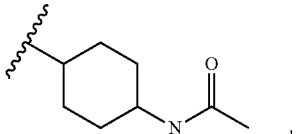
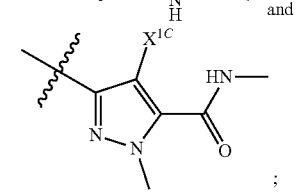
$R^3$ is selected from the group consisting of a substituted
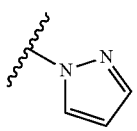 [SMILES: *n1cccn1]
and an unsubstituted or a substituted
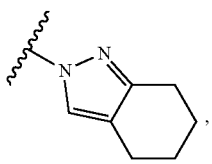 [SMILES: *n1cc2c(n1)CCCC2]
wherein when $R^3$ is a substituted
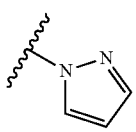 [SMILES: *n1cccn1]
or a substituted
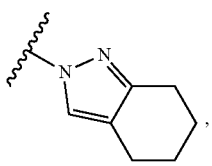 [SMILES: *n1cc2c(n1)CCCC2]
the

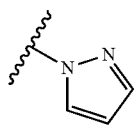

is substituted 2 or 3 times with substituents independently selected from the group consisting of deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH (an unsubstituted $C_{1-4}$ alkyl) and —C(=O)N (an unsubstituted $C_{1-4}$ alkyl)$_2$; the

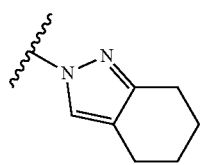 [SMILES: *n1cc2c(n1)CCCC2]

are substituted 1, 2 or 3 times with substituents independently selected from the group consisting of deuterium, halogen, cyano, an unsubstituted $C_{1-5}$ alkyl, a $C_{1-5}$ alkyl substituted with an unsubstituted $C_{1-5}$ alkoxy, an unsubstituted $C_{1-5}$ alkoxy, an unsubstituted $C_{3-4}$ cycloalkyl, an unsubstituted $C_{1-5}$ haloalkyl, —C(=O)NH$_2$, —C(=O)NH (an unsubstituted $C_{1-4}$ alkyl) and —C(=O)N (an unsubstituted $C_{1-4}$ alkyl)$_2$; and provided that $R^3$ is not

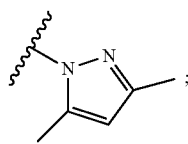 [SMILES: *n1nc(C)cc1C]

$X^{1A}$, $X^{1B}$ and $X^{1C}$ are independently selected from the group consisting of hydrogen, halogen, an unsubstituted $C_{1-5}$ alkyl and an unsubstituted $C_{1-5}$ haloalkyl;

$Y^{1A}$ is CH, C—CHF$_2$, C—F, C—Cl, C(NH$_2$), C(NH (unsubstituted $C_{1-5}$ alkyl)), C(N(unsubstituted $C_{1-5}$ alkyl)$_2$) or N;

$Y^{2A}$ is CH, C-halogen, C—OCH$_3$, C(NH$_2$), C(NH(unsubstituted $C_{1-5}$ alkyl)), C(N(unsubstituted $C_{1-5}$ alkyl)$_2$) or N;

$Y^{3A}$ is CH or N;

$Y^{4A}$ is CH or N;

$Y^{1B}$ is CH, C—CHF$_2$, C—F, C—Cl, C(NH$_2$), C(NH (unsubstituted $C_{1-5}$ alkyl)), C(N(unsubstituted $C_{1-5}$ alkyl)$_2$) or N;

$Y^{2B}$ is CH, C-halogen, C—OCH$_3$, C(NH$_2$), C(NH(unsubstituted $C_{1-5}$ alkyl)), C(N(unsubstituted $C_{1-5}$ alkyl)$_2$) or N;

$Y^{3B}$ is CH or N;

$Y^{4B}$ is CH or N;

$Y^{1C}$, $Y^{2C}$, $Y^{3C}$ and $Y^{4C}$ are each independently CH, C-(halogen) or N;

$Y^{1D}$ is CH, C—CH$_3$, C—OCH$_3$, C-(halogen), C—CHF$_2$, C—CF$_3$ or N;

$Y^{2D}$ is CH, C—CH$_3$, C—OCH$_3$, C-(halogen), C—CHF$_2$, C—CF$_3$ or N;

$Y^{3D}$ is CH, C-(halogen) or N;

$Y^{1E}$, $Y^{1F}$ and $Y^{1G}$ are each independently CH, C-(halogen) or N;

$Y^{1H}$, $Y^{2H}$, $Y^{3H}$, $Y^{4H}$, $Y^{5H}$ and $Y^{6H}$ are each independently CH, C-(halogen) or N;

$R^{41}$ is hydrogen, an unsubstituted or a substituted $C_{1-5}$ alkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl is substituted with one or more groups selected from the group consisting of hydroxy, —NH$_2$, an unsubstituted $C_{1-5}$ alkoxy, an unsubstituted-NH (an unsubstituted $C_{1-5}$ alkyl), —N(an unsubstituted $C_{1-5}$ alkyl)$_2$, —C(=O)NH$_2$, —O—P(=O)(OH)$_2$, an unsubstituted 5- or 6-membered monocyclic heterocyclyl and 5- or 6-membered monocyclic heterocyclyl substituted by one or more unsubstituted $C_{1-4}$ alkyl groups;

$R^{42}$ is —CH$_3$ or —CD$_3$, $R^{43}$ is —NH$_2$, —NH (an unsubstituted or a substituted $C_{1-5}$ alkyl), —N(an unsubstituted or a substituted $C_{1-5}$ alkyl)$_2$, —NH (an unsubstituted or a substituted $C_{3-6}$ monocyclic cycloalkyl), an unsubstituted or a substituted 5-membered-monocyclic heteroaryl, an unsubstituted or a substituted 6-membered-monocyclic heteroaryl or an unsubstituted or a substituted 4 to 6-membered-monocyclic heterocyclyl;

$R^{44}$ is an unsubstituted or a substituted $C_{1-5}$ alkyl, an unsubstituted $C_{1-5}$ haloalkyl or an unsubstituted or a substituted monocyclic $C_{3-6}$ cycloalkyl, wherein when the $C_{1-5}$ alkyl and the monocyclic $C_{3-6}$ cycloalkyl are substituted, the $C_{1-5}$ alkyl and the $C_{3-6}$ cycloalkyl are substituted with one or more groups selected from the group consisting of hydroxy, —C(=O) OH and —C(=O)NH$_2$; and $R^{45}$ is selected from the group consisting of hydrogen, halogen, —CN, —OH, —NH$_2$, —C(=O)OH, —CH=CH$_2$, an unsubstituted $C_{1-5}$ alkyl, and an unsubstituted or a substituted monocyclic $C_{3-6}$ cycloalkyl, wherein when the monocyclic $C_{3-6}$ cycloalkyl is substituted, the $C_{3-6}$ cycloalkyl is substituted with one or more hydroxy groups.

2. The compound of claim 1, wherein R is a di-substituted phenyl.

3. The compound of claim 2, wherein $R^2$ is

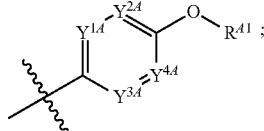

$Y^{1A}$, $Y^{2A}$, $Y^{3A}$ and $Y^{4A}$ are each CH, or one of $Y^{1A}$, $Y^{2A}$, $Y^{3A}$ and $Y^{4A}$ is N.

4. The compound of claim 2, wherein $R^2$ is

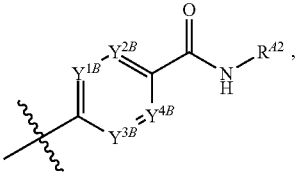

5. The compound of claim 2, wherein R² is

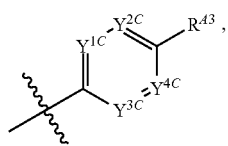

Y¹$^C$, Y²$^C$, Y³$^C$ and Y⁴$^C$ are each CH, or one of Y¹$^C$, Y²$^C$, Y³$^C$ and Y⁴$^C$ is N; and R$^{A3}$ is an unsubstituted or a substituted 5-membered-monocyclic heteroaryl.

6. The compound of claim 2, wherein R² is

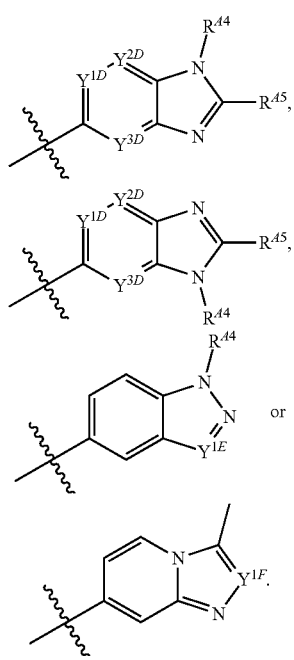

7. The compound of claim 6, wherein R$^{A4}$ is an unsubstituted C$_{1-5}$ alkyl or an unsubstituted monocyclic C$_{3-6}$ cycloalkyl.

8. The compound of claim 2, wherein R² is

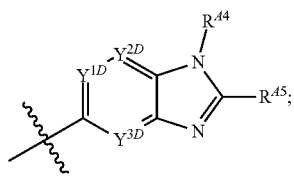

and R$^{A5}$ is hydrogen.

9. The compound of claim 8, wherein Y¹$^D$ is CH or C-(halogen); Y²$^D$ is CH, C—CH₃, C—OCH₃, C-(halogen), C—CHF₂ or C—CF₃; and Y³$^D$ is CH, C—CH₃, C—OCH₃, C-(halogen), C—CHF₂ or C—CF₃.

10. The compound of claim 8, wherein Y¹$^D$ is CH or C-(halogen); Y²$^D$ is N; and Y³$^D$ is CH, C—CH₃, C—OCH₃, C-(halogen), C—CHF₂ or C—CF₃.

11. The compound of claim 2, wherein R² is selected from the group consisting of

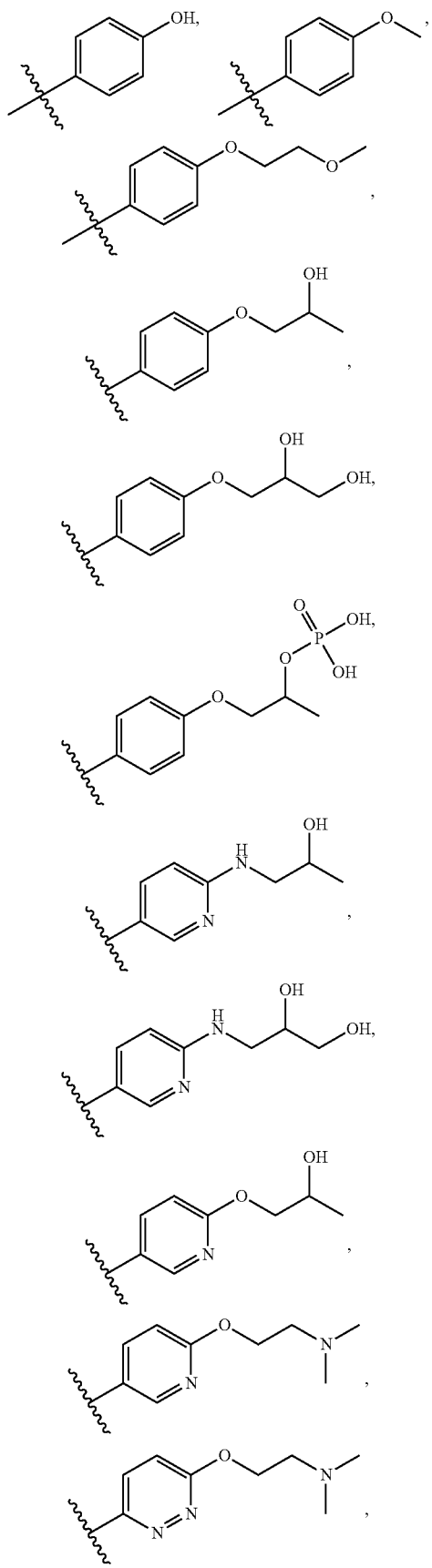

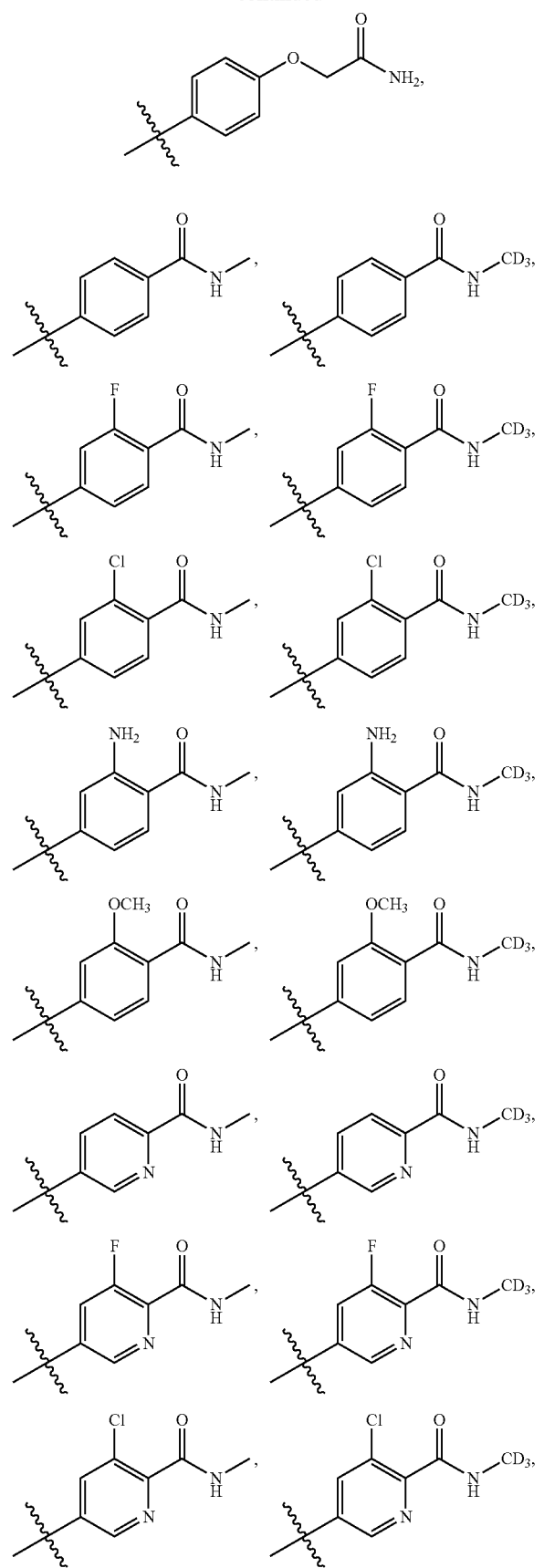
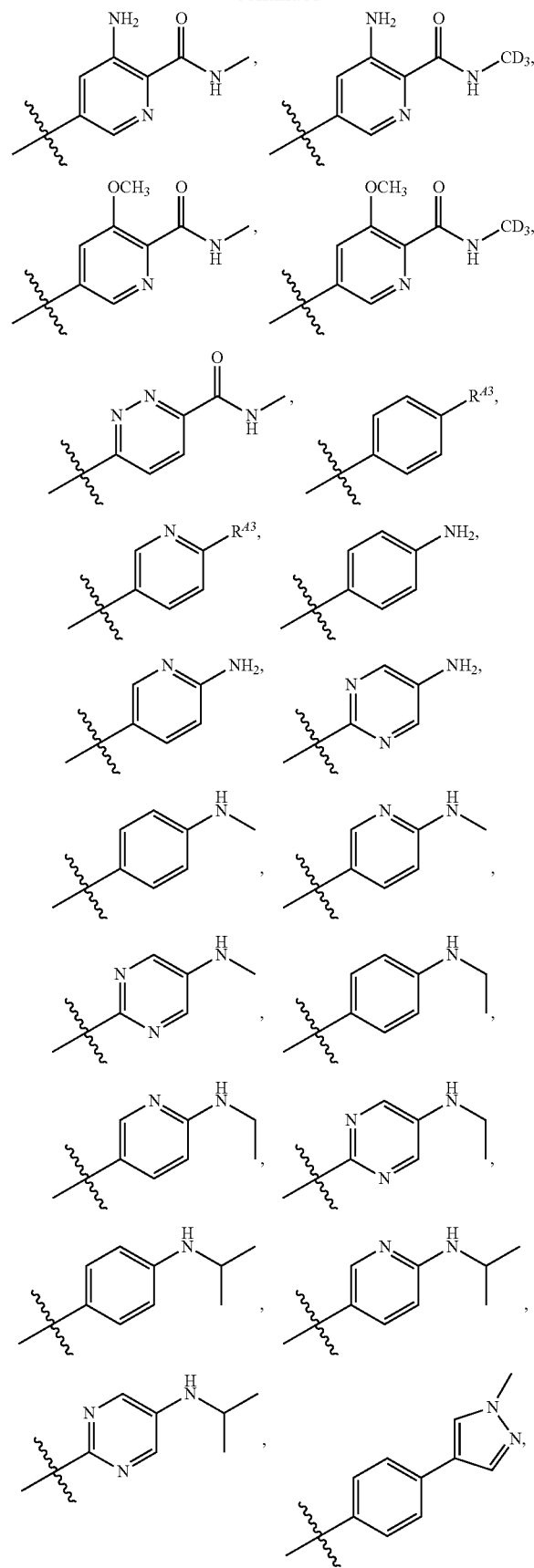

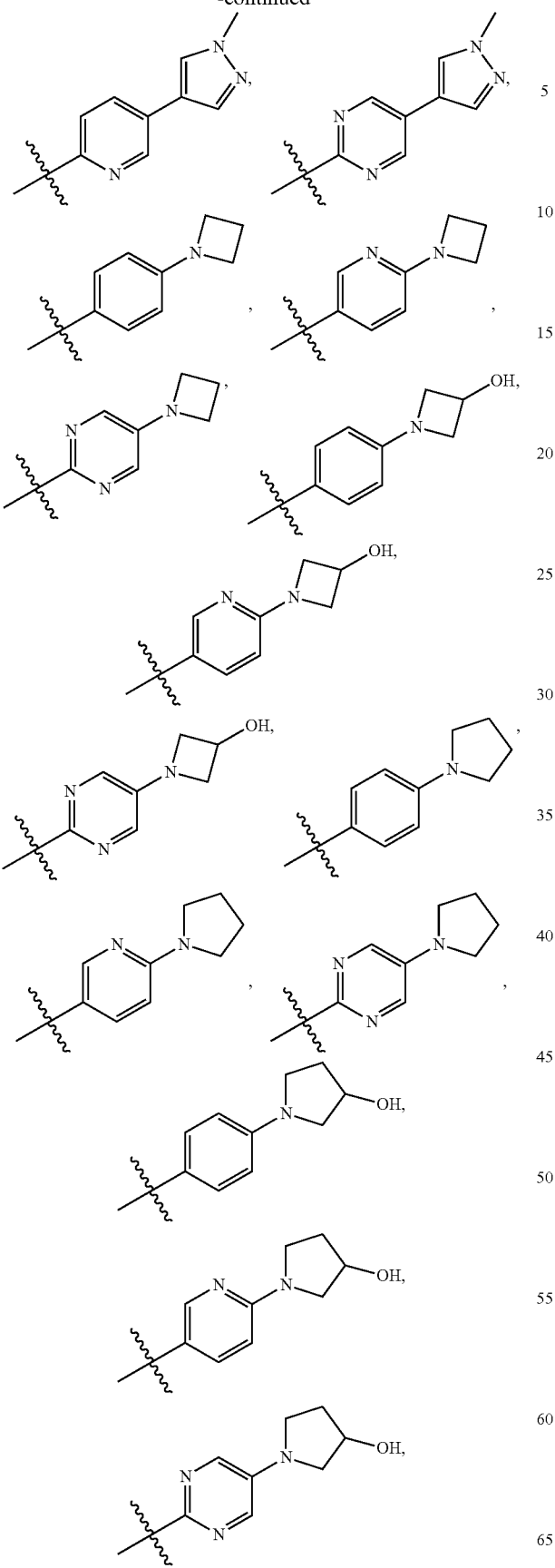
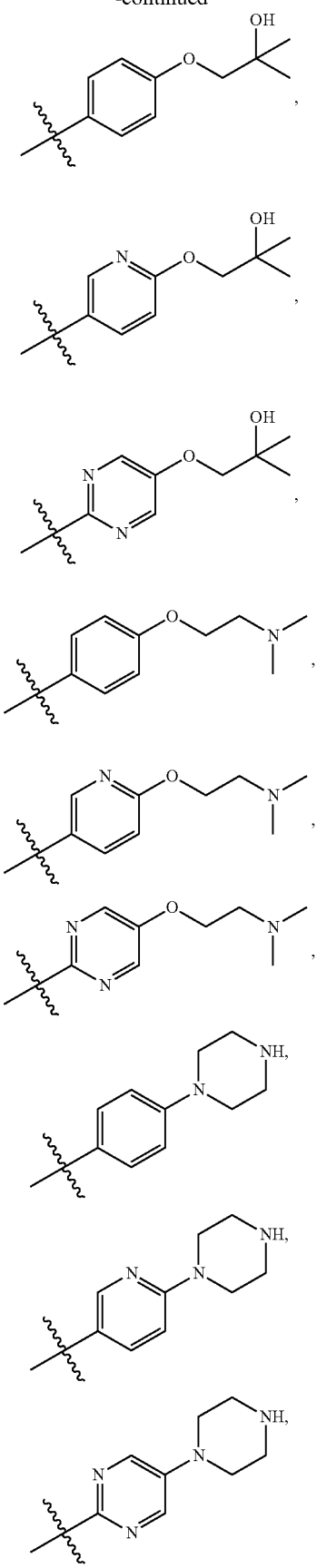

109
-continued
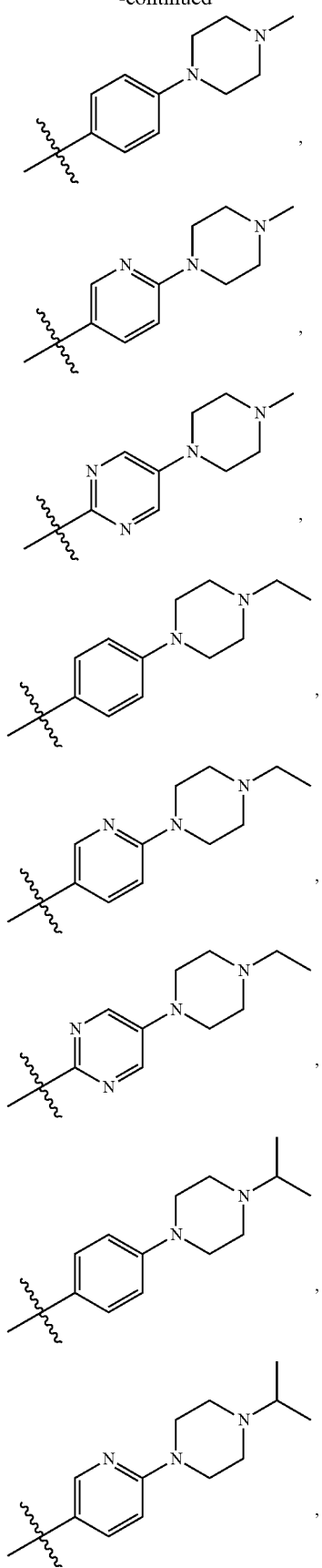
110
-continued
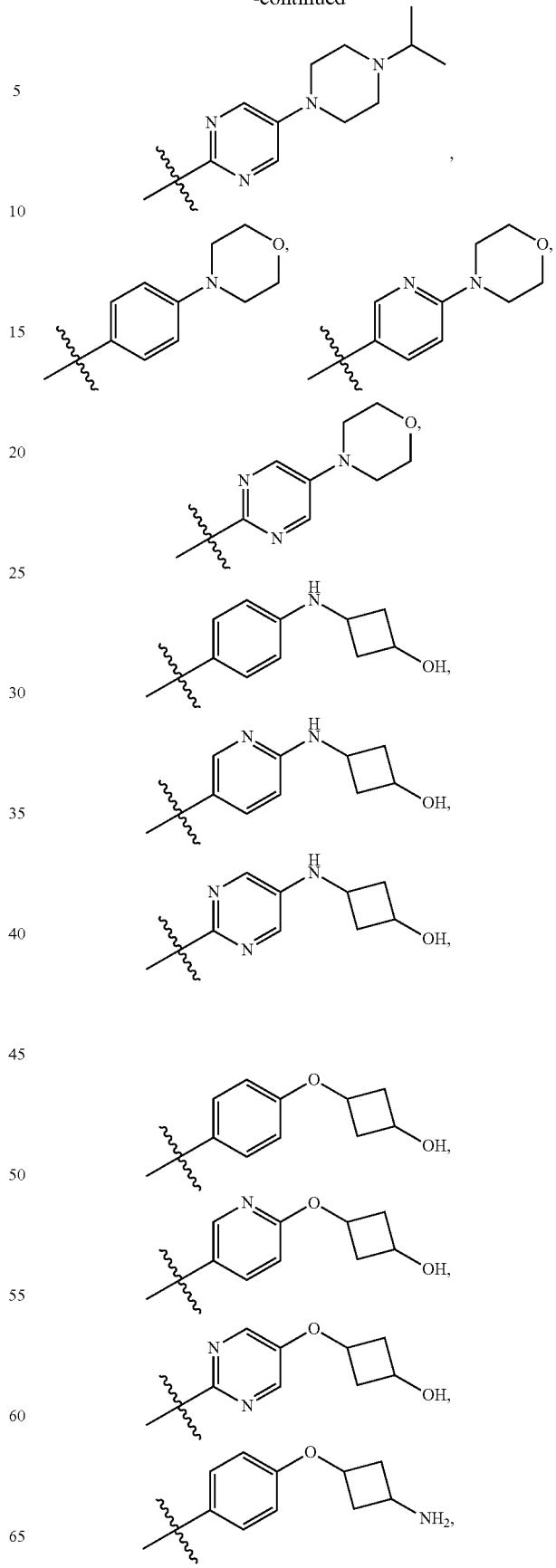

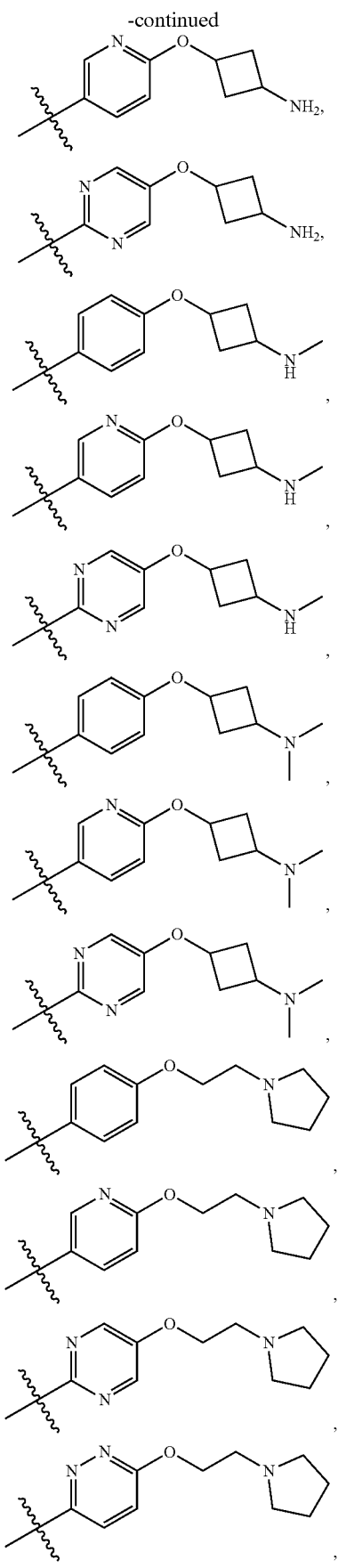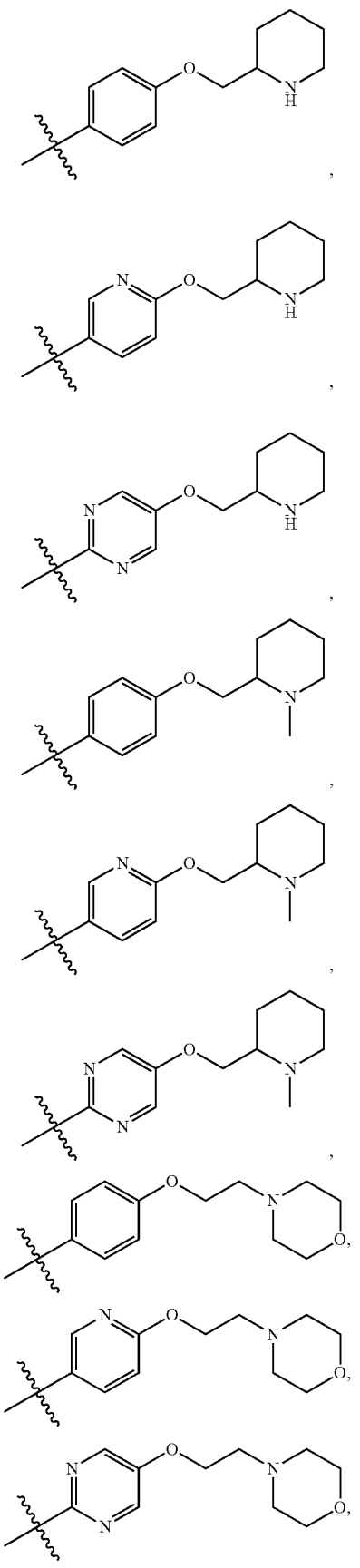

-continued
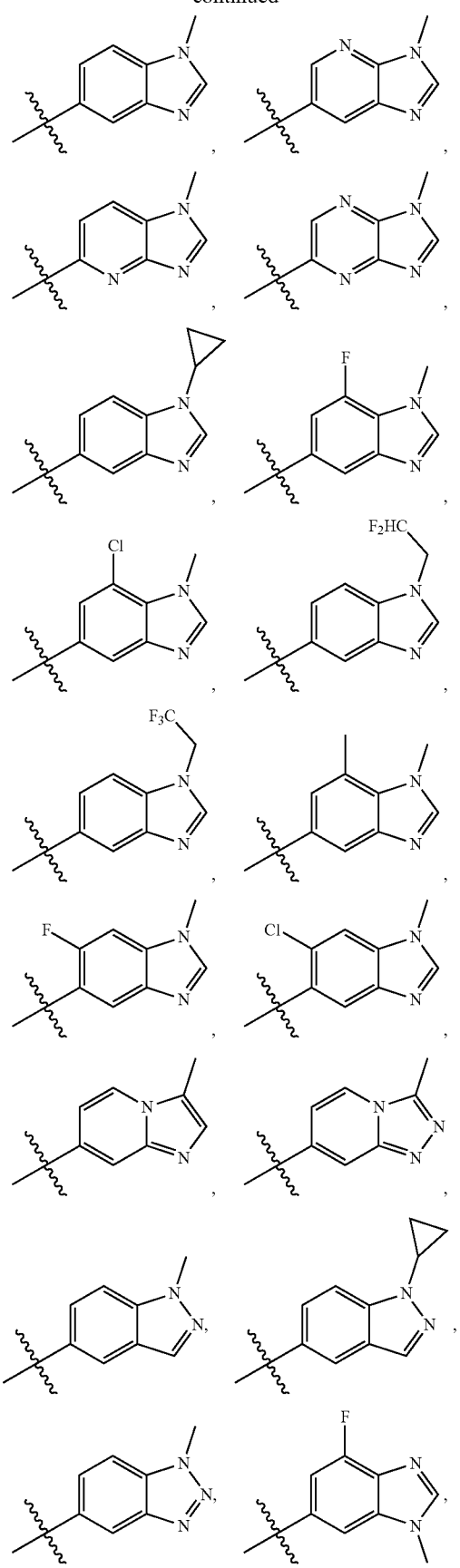
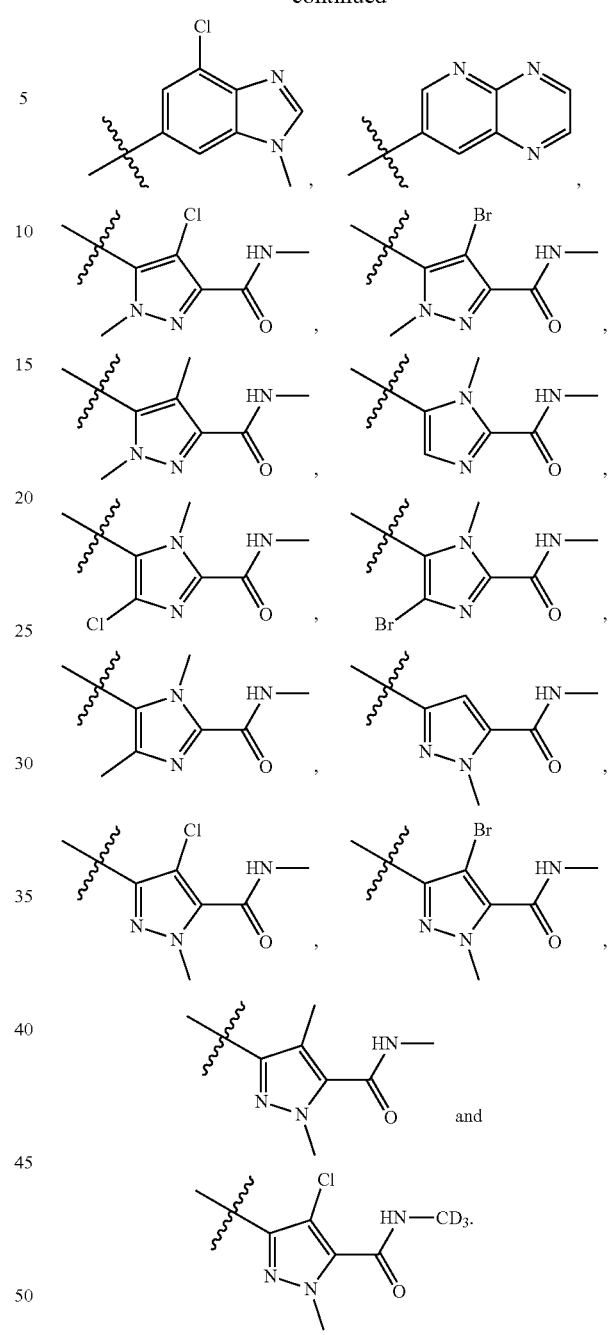
12. The compound of claim 2, wherein R³ is an unsubstituted or a substituted
13. The compound of claim 2, wherein R³ is selected from the group consisting of:

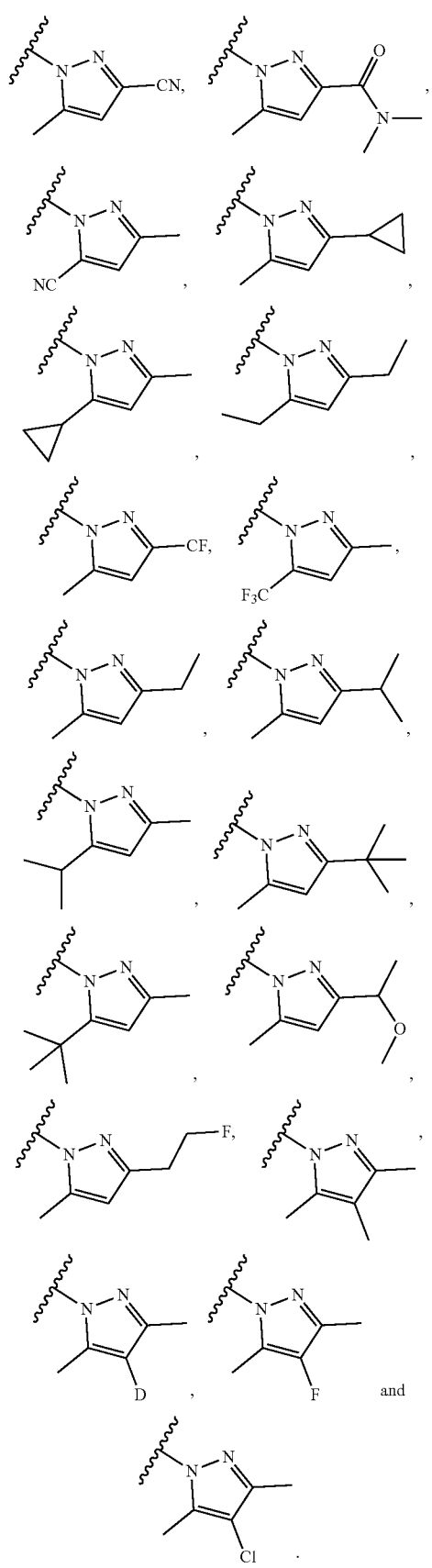
14. The compound of claim 1, wherein R¹ is selected from the group consisting of:
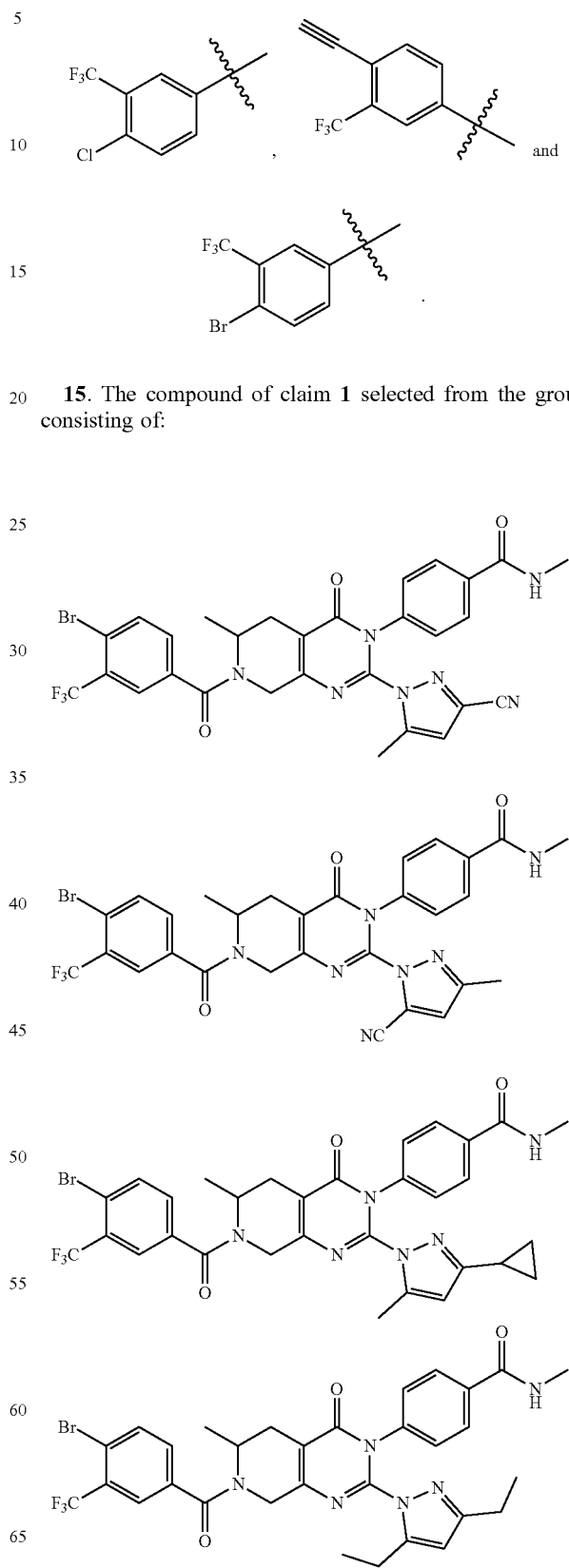
15. The compound of claim 1 selected from the group consisting of:

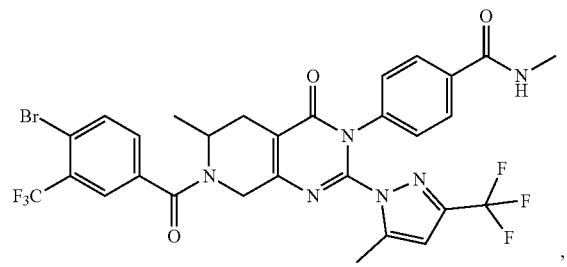,
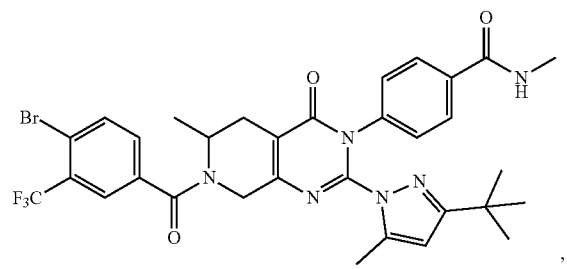,
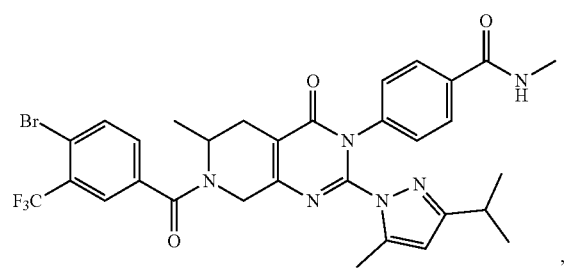,
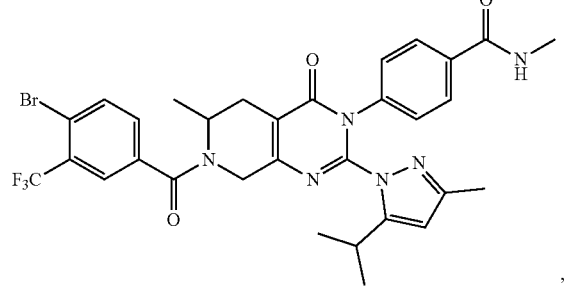,
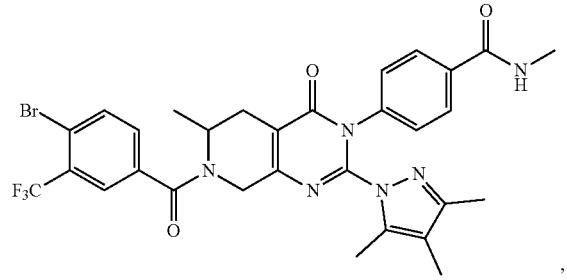,
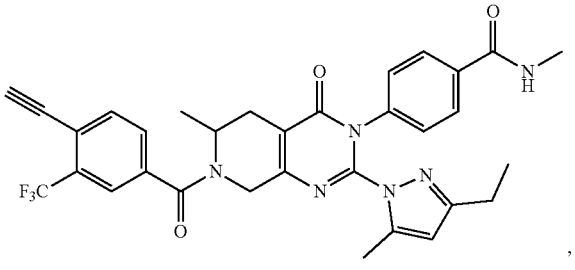,
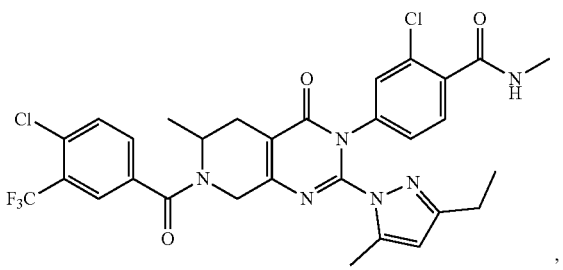,
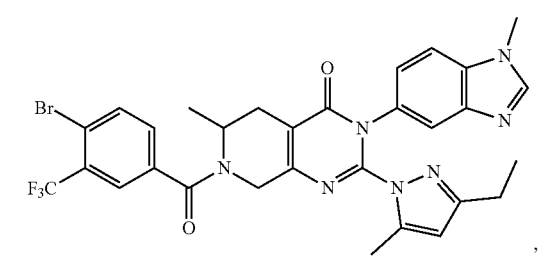,
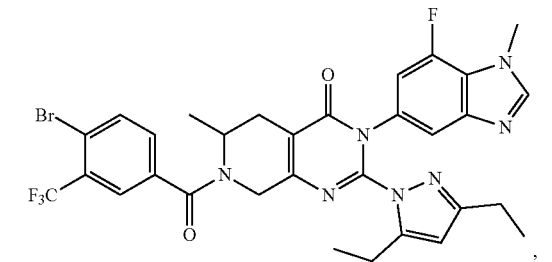,
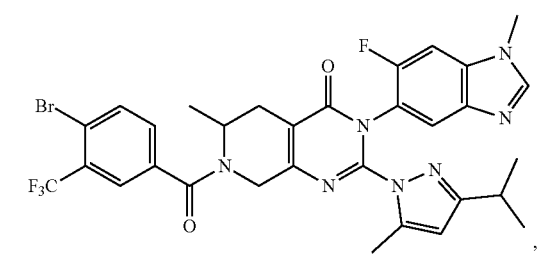,
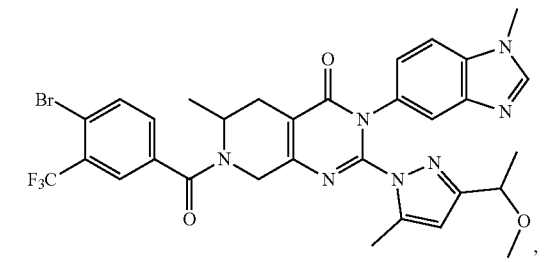,
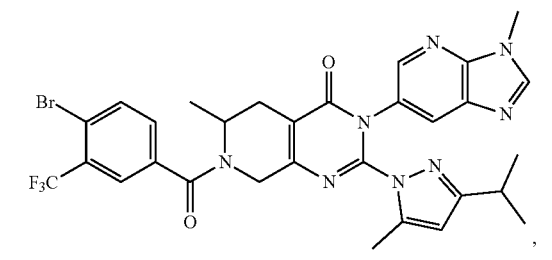,

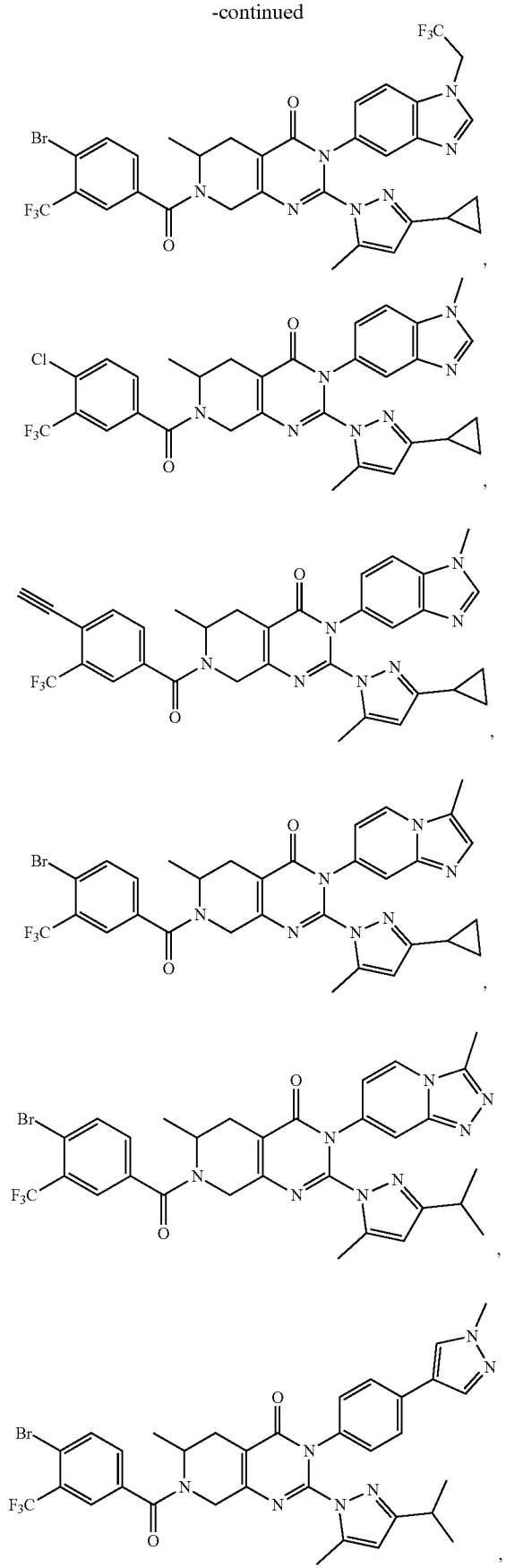
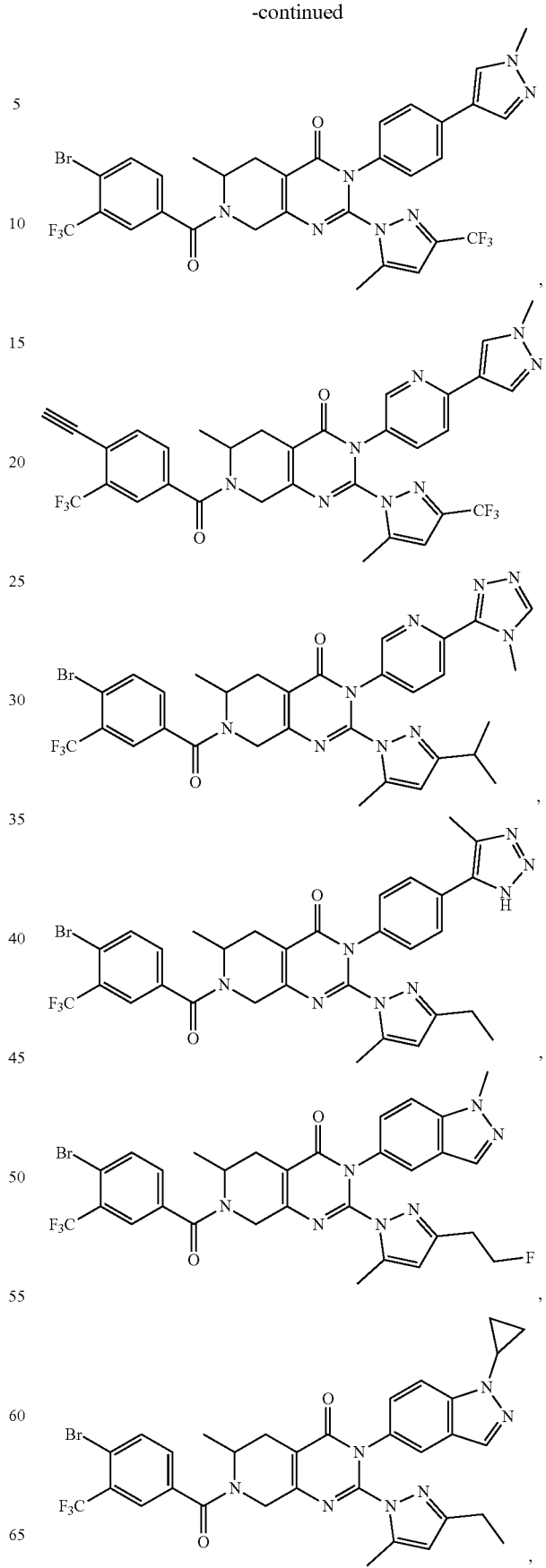

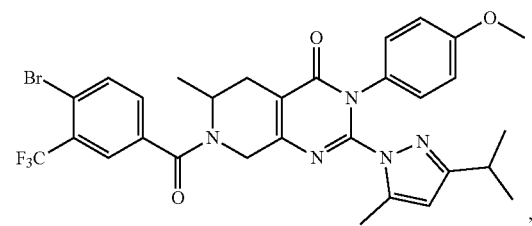
,
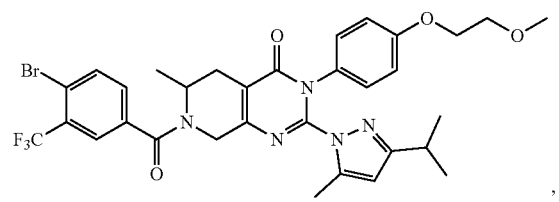
,
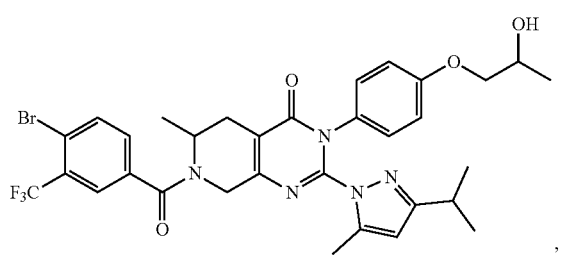
,
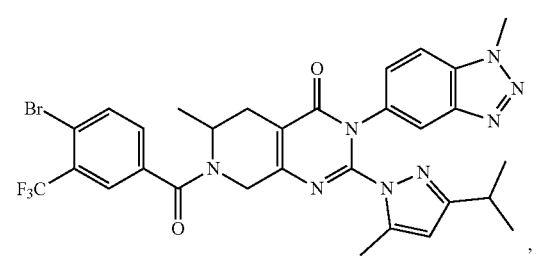
,
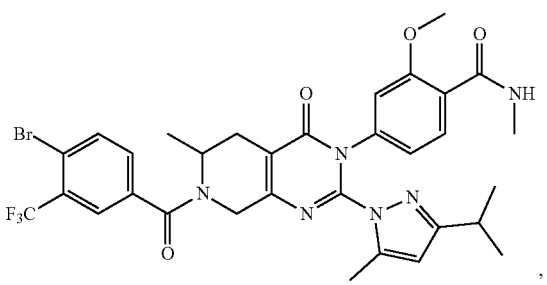
,
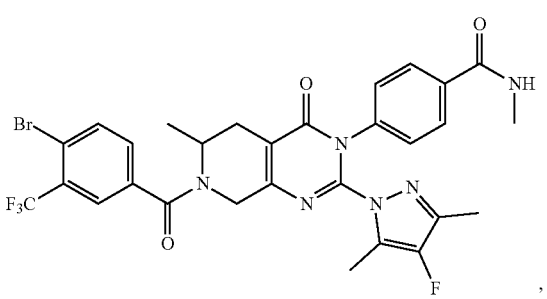
,
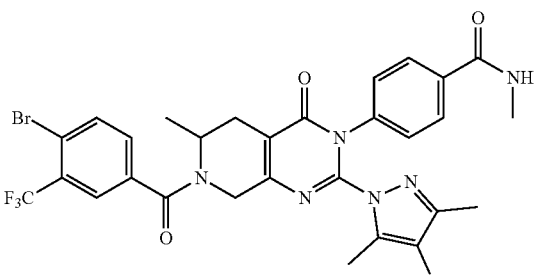
,
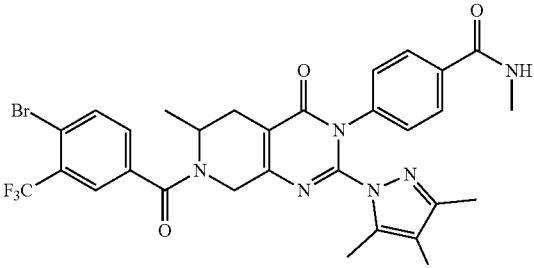
,
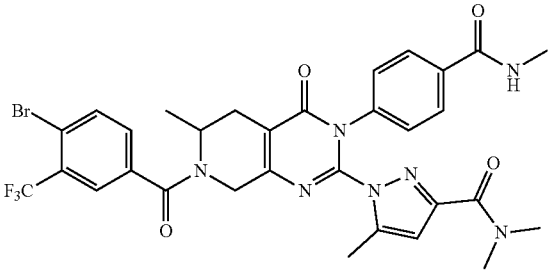
,
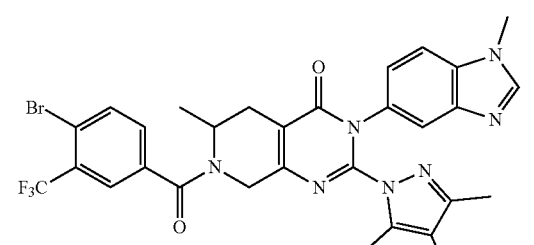
,
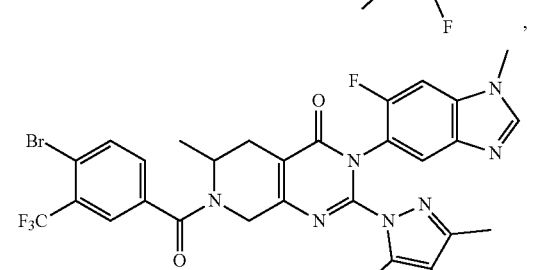
,
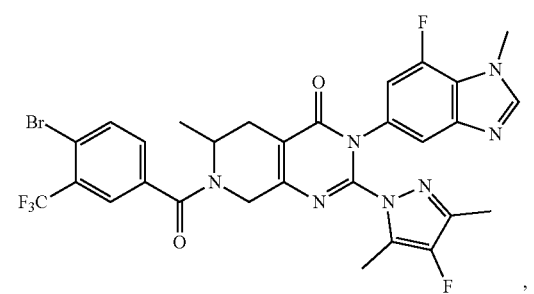
, 123
-continued
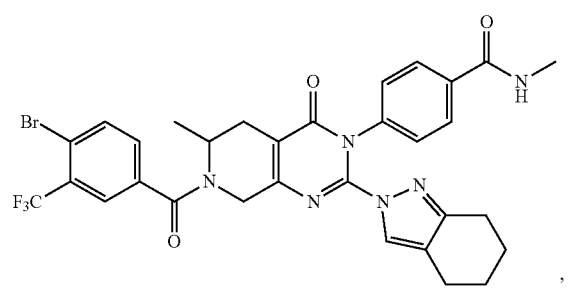
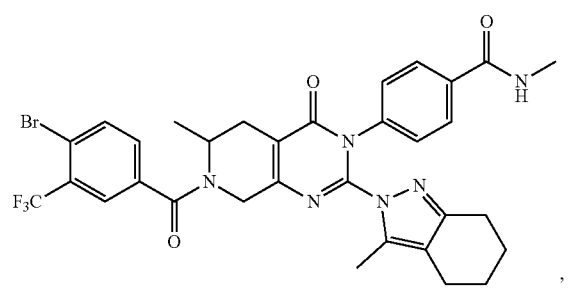
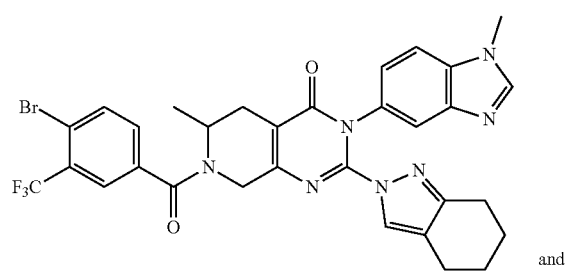
and
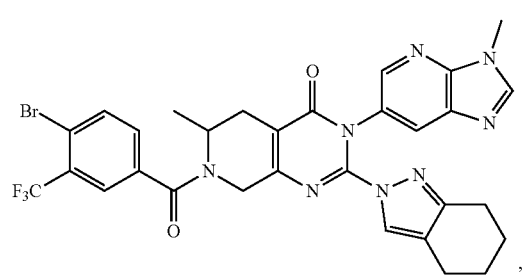
or a pharmaceutically acceptable salt of any of the foregoing.
16. The compound of claim 1 selected from the group consisting of:
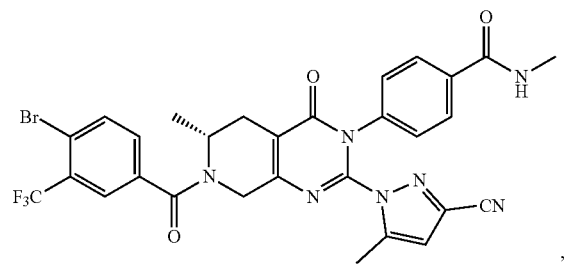
124
-continued
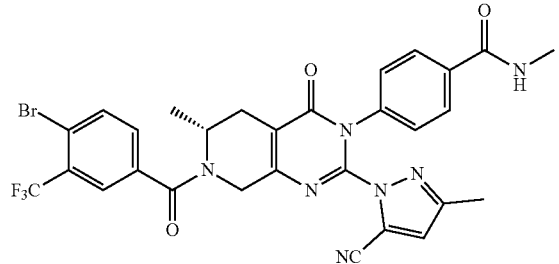
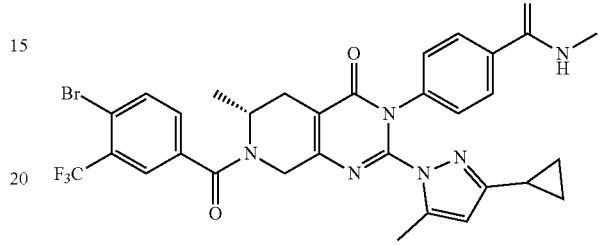
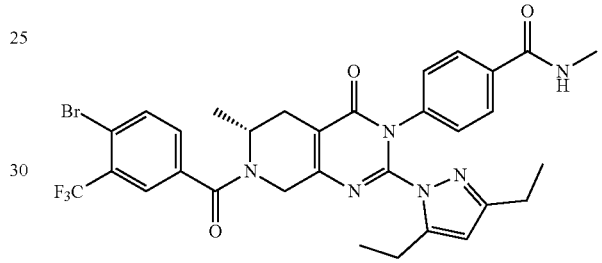
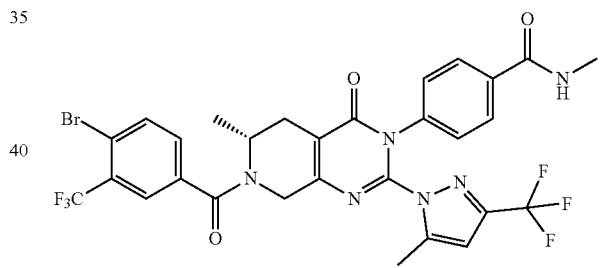
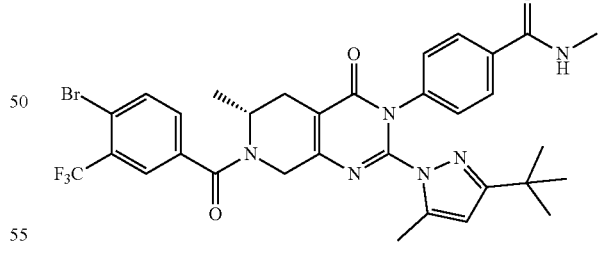
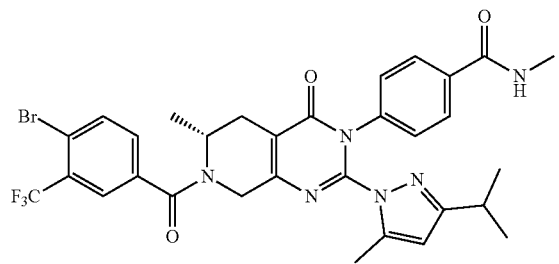

125
-continued
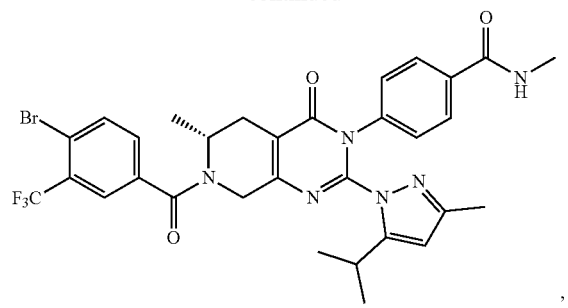
,
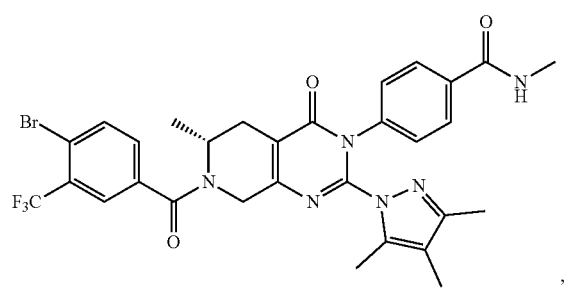
,
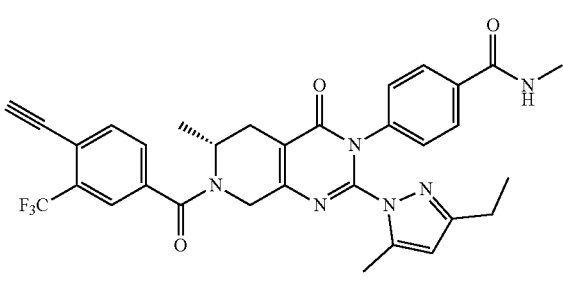
,
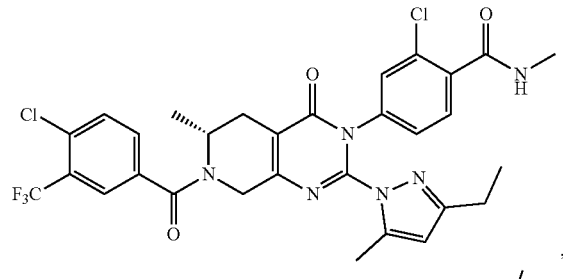
,
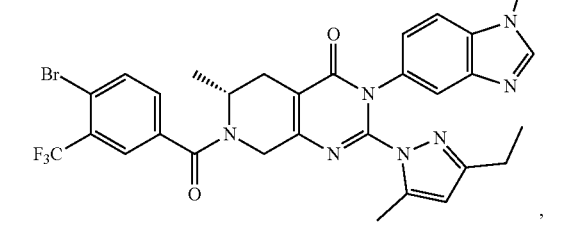
,
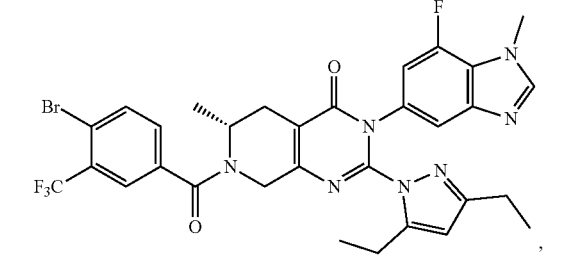
,
126
-continued
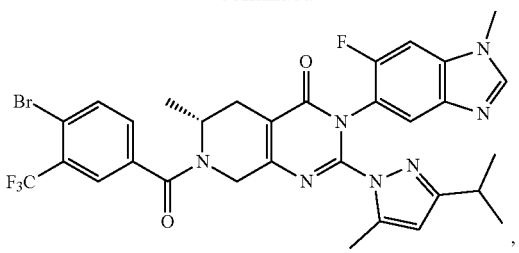
,
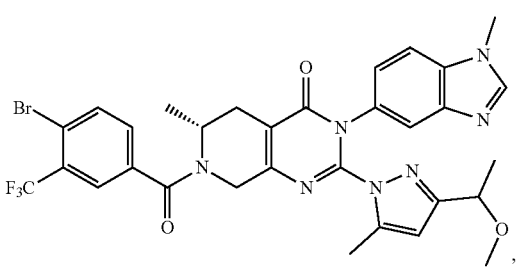
,
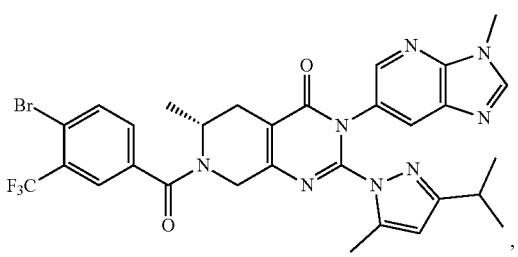
,
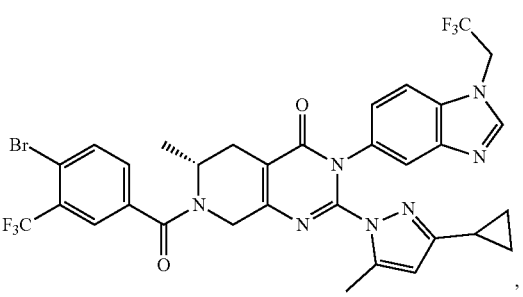
,
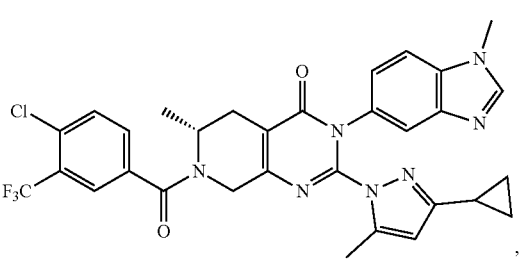
,
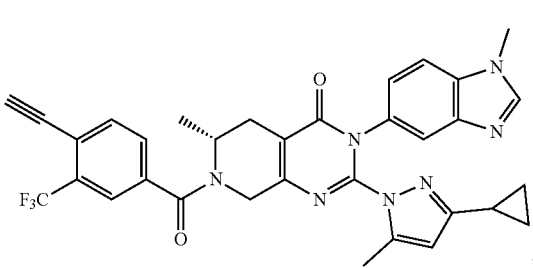
,

127
-continued
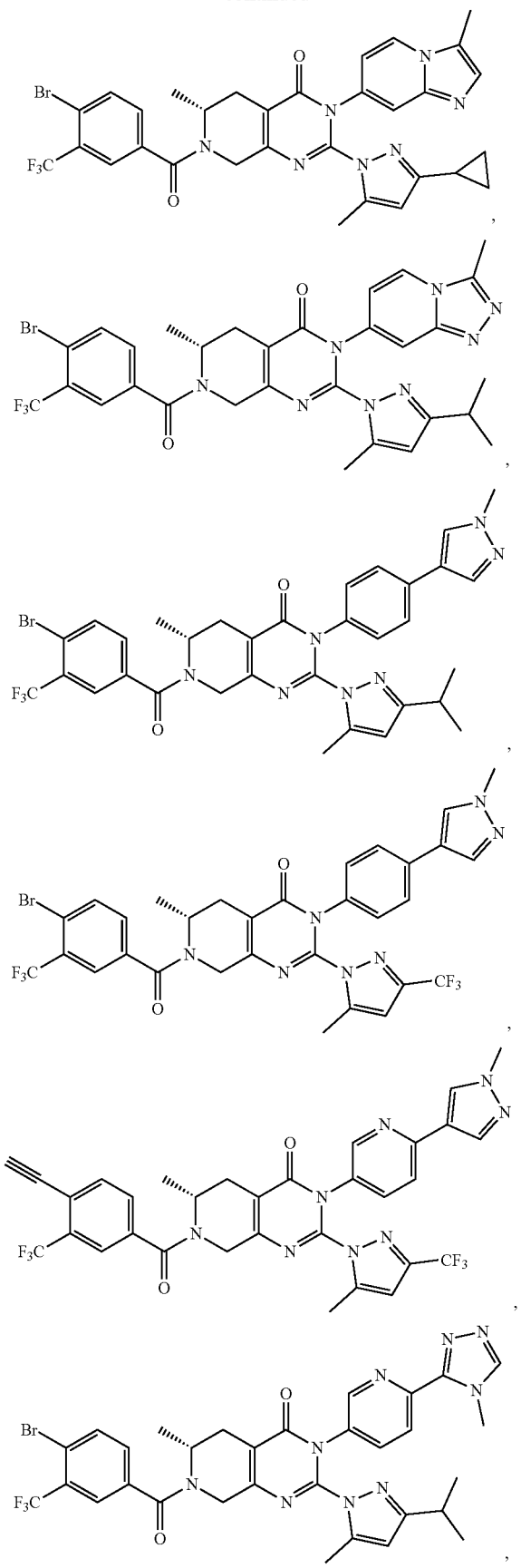
128
-continued
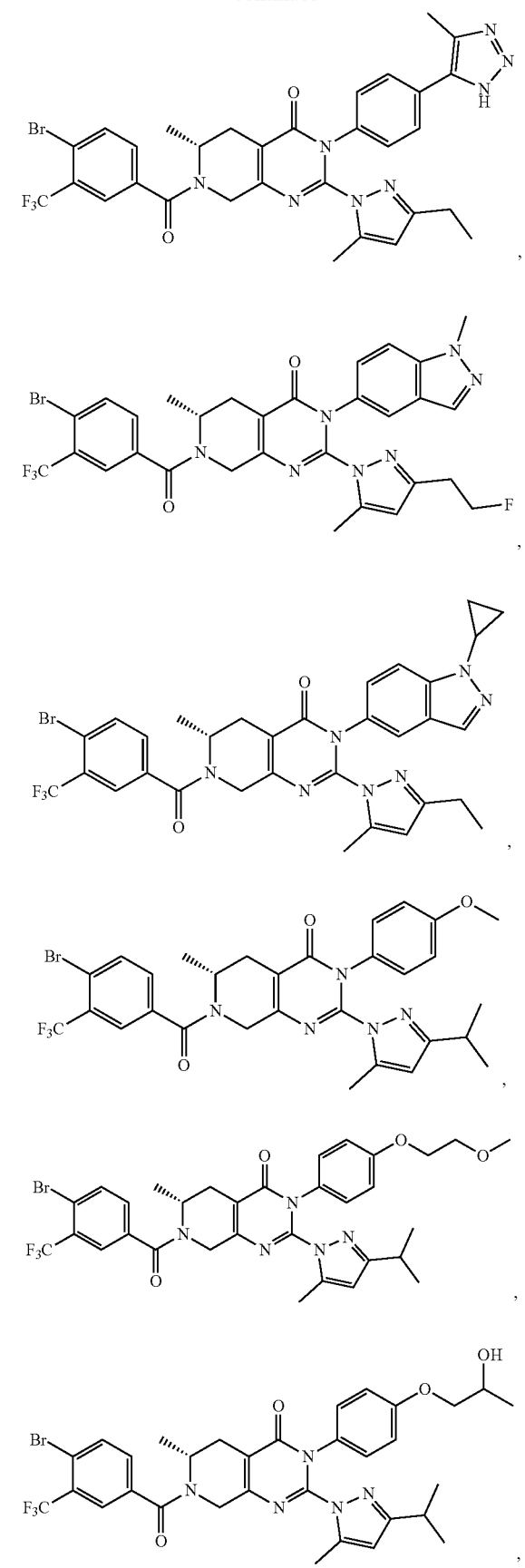

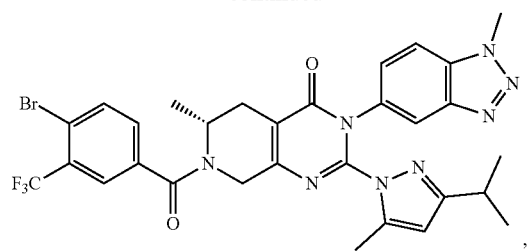
,
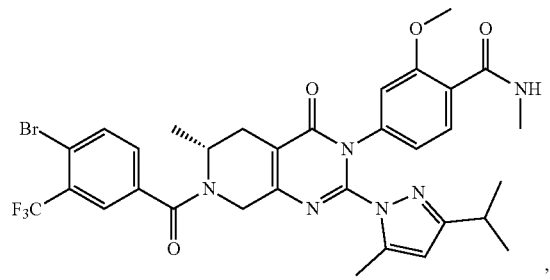
,
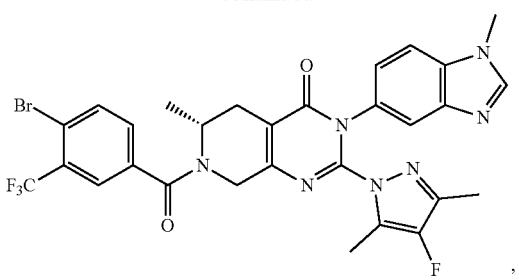
,
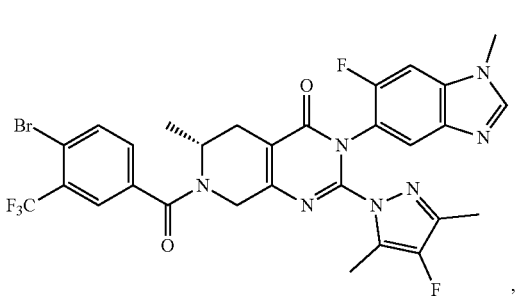
,
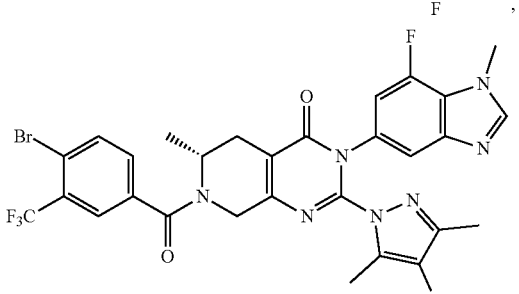
,
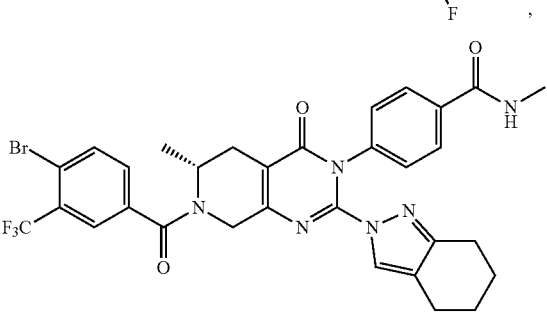
,
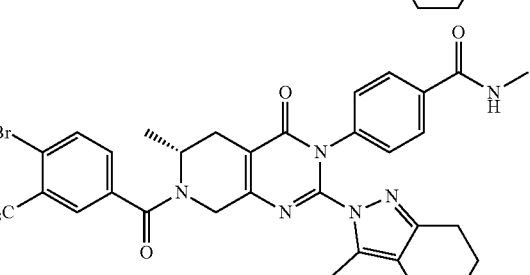
,
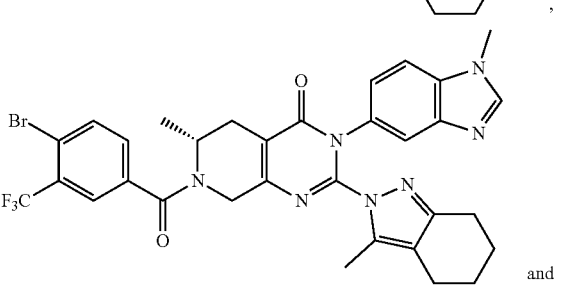
and

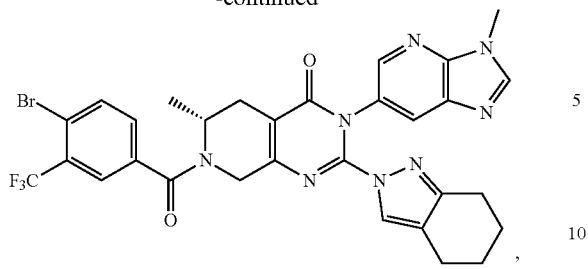

or a pharmaceutically acceptable salt of any of the foregoing.

17. A pharmaceutical composition comprising an effective amount of a compound of claim 1, or a pharmaceutically acceptable salt thereof, and excipient.

18. A method for treating hepatitis B in a subject comprising administering to the subject in need thereof an effective amount of a compound of claim 1, or a pharmaceutically acceptable salt thereof.

\* \* \* \* \*